(12) United States Patent
Eckhardt et al.

(10) Patent No.: US 7,847,074 B2
(45) Date of Patent: Dec. 7, 2010

(54) PROCESSES FOR PREPARING OF GLUCOPYRANOSYL-SUBSTITUTED (ETHYNYL-BENZYL)-BENZENE DERIVATIVES AND INTERMEDIATES THEREOF

(75) Inventors: Matthias Eckhardt, Biberach (DE); Frank Himmelsbach, Mittelbiberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 791 days.

(21) Appl. No.: 11/531,898

(22) Filed: Sep. 14, 2006

(65) Prior Publication Data

US 2007/0073046 A1 Mar. 29, 2007

(30) Foreign Application Priority Data

Sep. 15, 2005 (EP) .................. 05108487

(51) Int. Cl.
*C07H 1/00* (2006.01)
*C07H 3/00* (2006.01)

(52) U.S. Cl. ...................... 536/1.11; 536/124
(58) Field of Classification Search ........................ None
See application file for complete search history.

(56) References Cited

U.S. PATENT DOCUMENTS

| | | | |
|---|---|---|---|
| 4,786,023 A | 11/1988 | Harris et al. | |
| 4,786,755 A | 11/1988 | Kiely et al. | |
| 6,414,126 B1 | 7/2002 | Ellesworth et al. | |
| 6,515,117 B2 | 2/2003 | Ellesworth et al. | |
| 6,627,611 B2 | 9/2003 | Tomiyama et al. | |
| 6,774,112 B2 | 8/2004 | Gougoutas | |
| 6,936,590 B2 | 8/2005 | Washburn et al. | |
| 7,169,761 B2 | 1/2007 | Tomiyama et al. | |
| 7,202,350 B2 | 4/2007 | Imamura et al. | |
| 7,371,732 B2 | 5/2008 | Eickelmann et al. | |
| 7,375,090 B2 | 5/2008 | Himmelsbach et al. | |
| 7,393,836 B2 | 7/2008 | Eckhardt et al. | |
| 7,417,032 B2 | 8/2008 | Eckhardt et al. | |
| 7,419,959 B2 | 9/2008 | Eckhardt et al. | |
| 7,579,449 B2 | 8/2009 | Eckhardt et al. | |
| 2002/0137903 A1 | 9/2002 | Ellsworth et al. | |
| 2003/0064935 A1 | 4/2003 | Gougoutas | |
| 2003/0114390 A1 | 6/2003 | Washburn et al. | |
| 2004/0138148 A1 | 7/2004 | Fushimi et al. | |
| 2004/0138439 A1 | 7/2004 | Deshpande et al. | |
| 2005/0065098 A1 | 3/2005 | Fujikura et al. | |
| 2005/0124555 A1 | 6/2005 | Tomiyama et al. | |
| 2005/0209166 A1* | 9/2005 | Eckhardt et al. .............. 514/23 |
| 2006/0019948 A1 | 1/2006 | Eckhardt et al. | |
| 2006/0035841 A1 | 2/2006 | Eckhardt et al. | |
| 2006/0063722 A1 | 3/2006 | Washburn et al. | |
| 2006/0142210 A1 | 6/2006 | Eckhardt et al. | |
| 2006/0189548 A1 | 8/2006 | Himmelsbach et al. | |
| 2006/0234953 A1 | 10/2006 | Himmelsbach et al. | |
| 2006/0251728 A1 | 11/2006 | Himmelsbach et al. | |
| 2006/0258749 A1 | 11/2006 | Eckhardt et al. | |
| 2007/0004648 A1 | 1/2007 | Himmelsbach et al. | |
| 2007/0027092 A1 | 2/2007 | Himmelsbach et al. | |
| 2007/0049537 A1 | 3/2007 | Eckhardt et al. | |
| 2007/0054867 A1 | 3/2007 | Eckhardt et al. | |
| 2007/0249544 A1 | 10/2007 | Himmelsbach et al. | |
| 2007/0259821 A1 | 11/2007 | Eckhardt et al. | |
| 2008/0058379 A1 | 3/2008 | Eckhardt et al. | |
| 2009/0023913 A1 | 1/2009 | Eckhardt et al. | |

FOREIGN PATENT DOCUMENTS

| | | |
|---|---|---|
| CA | 2 388 818 A1 | 4/2001 |
| CA | 2 494 177 A1 | 2/2004 |
| CA | 2 508 024 A1 | 6/2004 |
| CA | 2 508 226 A1 | 6/2004 |
| CA | 2 557 269 A1 | 9/2005 |
| CA | 2 557 320 A1 | 9/2005 |
| CA | 2 557 801 A1 | 10/2005 |
| CA | 2 573 777 A1 | 2/2006 |
| EP | 0 206 567 A2 | 6/1986 |
| EP | 1344780 A1 | 9/2003 |
| EP | 1 385 856 A0 | 2/2004 |
| EP | 1224195 B | 5/2005 |
| EP | 1 553 094 A1 | 7/2005 |
| EP | 1 609 785 A1 | 12/2005 |
| JP | 58/164502 A | 9/1983 |
| JP | 62/030750 A | 2/1987 |
| JP | 11/124392 A | 5/1999 |

(Continued)

OTHER PUBLICATIONS

Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.

(Continued)

*Primary Examiner*—Traviss C McIntosh, III
(74) *Attorney, Agent, or Firm*—Michael P. Morris; Edouard G. Lebel; David A. Dow

(57) ABSTRACT

The present invention relates to processes for preparing the compounds of general formula I,

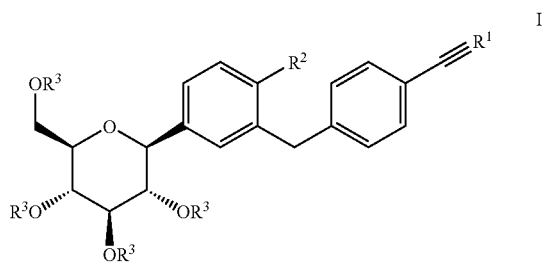

wherein the groups $R^1$, $R^2$ and $R^3$ are defined according to claim 1 and to intermediates of said processes.

16 Claims, No Drawings

FOREIGN PATENT DOCUMENTS

| | | |
|---|---|---|
| JP | 2001/288178 A | 10/2001 |
| JP | 2003/511458 A | 3/2003 |
| JP | 2004/359630 A | 12/2004 |
| WO | 98/31697 | 7/1998 |
| WO | 01/27128 A1 | 4/2001 |
| WO | 01/74834 A1 | 10/2001 |
| WO | 02/064606 A1 | 8/2002 |
| WO | 02/083066 A2 | 10/2002 |
| WO | 03/099836 A1 | 12/2003 |
| WO | 2004/013118 A1 | 2/2004 |
| WO | 2004/052902 A1 | 6/2004 |
| WO | 2004/052903 A1 | 6/2004 |
| WO | 2004/063209 A2 | 7/2004 |
| WO | 2004/076470 A2 | 9/2004 |
| WO | 2004/080990 A1 | 9/2004 |
| WO | 2005/012326 A1 | 1/2005 |
| WO | 2005/012318 A2 | 2/2005 |
| WO | 2005/085237 A1 | 9/2005 |
| WO | 2005/085265 A1 | 9/2005 |
| WO | 2005/092877 A1 | 10/2005 |
| WO | 2006/011469 A1 | 2/2006 |
| WO | 2006/034489 A2 | 3/2006 |
| WO | 2006/064033 A2 | 6/2006 |
| WO | 2006/089872 A1 | 8/2006 |
| WO | 2006/108842 A1 | 10/2006 |
| WO | 2006/117360 A1 | 11/2006 |
| WO | 2006/120208 A1 | 11/2006 |
| WO | 2007/014894 A2 | 2/2007 |
| WO | 2007/025943 A2 | 3/2007 |
| WO | 2007/028814 A1 | 3/2007 |
| WO | 2007/031548 A2 | 3/2007 |

OTHER PUBLICATIONS

Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.

Jagdmann Jr, G. Erik ; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.

Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.

Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.

Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Kuribayashi, Takeshi., et al; Bis C-Glycosylated Diphenylmethanes for Stable Glycoepitope Mimetics; Syntletters (1999) vol. 6 pp. 737-740.

Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

Mclaughlin, Mark., et al; Suzuki-Miyaura Cross-Coupling of Benzylic Phospahates with Arylboronic Acids; Organic Letters (2005) vol. 7 No. 22 pp. 4875-4878.

Neamati, Ouri., et al;, "Depsides and Depsidones as Inhibiton of HIV-1 Integrase: Dimvery of Novel Inhibitors Through 3D Database Searching", J. Med. Chem., 1997, vol. 40, pp. 942-951.

Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Oku, Akira., et al; T-1095, An Inhibitor or renal $Na^+$-Glucose Cotransporters, May Provide a Novel Approach to Treating Diabetes; Diabetes (1999) vol. 48 pp. 1794-1800.

Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.

Sommer, Michael Bech., et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.

Revesz, Lasslo., et al; Sar of Benzoylpylpyridines and Benzophenones as p38 Alpha MAP Kinase Inhibitors with Oral Activity; Bioorganic & Medicinal Chemistry Letters (2004) vol. 14 pp. 3601-3605.

Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.

Ueta, Kiichiro., et al; Long-Term Treatment with the $Na^+$- Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

Wallace, Debra J., et al; Cyclopropylboronic Acid: Synthesis and Suzuki Cross-Coupling Reactions; Tetrahedron Letters (2002) vol. 43 pp. 6987-6990; Pergamon Press.

Xue, Song., et al; Zinc-mediated Synthesis of Alpha-C-Glycosided from 1,2-Anhydroglycosides; Synletters (2003) vol. 6 pp. 870-872.

International Search Report for PCT/EP2005/002618 mailed Jun. 30, 2005.

International Search Report for PCT/EP2006/061956 mailed on Jul. 5, 2006.

International Search report for PCT/EP2006/061957 mailed on Jul. 5, 2006.

International Search Report for PCT/EP2006/061520 mailed Jul. 26, 2006.

International Search Report for PCT/EP2006/062191 mailed Aug. 8, 2006.

International Search Report for PCT/EP2005/056806 mailed Dec. 27, 2006.

International Search Report for corresponding international application PCT/EP2006/066107 mailed Jan. 11, 2007.

International Search Report for PCT/EP2006/066347 mailed Mar. 7, 2007.

International Search Report for PCT/EP2006/065710 mailed Mar. 8, 2007.

International Search Report for PCT/EP2007/051411 mailed on May 2, 2007.

International Search Report for PCT/EP2007/054248 mailed on Jun. 18, 2007.

International Search Report for PCT/EP2006/064702 mailed on Jul. 26, 2007.

Notice of Allowance and Fee(s) Due dated Jan. 13, 2009 from U.S. Appl. No. 11/304,284 filed Dec. 15, 2005.

Non-Final Office Action dated Jun. 24, 2008 from U.S. App. No. 11/406,971 filed Apr. 19, 2006.
Non-Final Office Action dated Jun. 5, 2008 from U.S. Appl. No. 11/408,899 filed on Apr. 21, 2006.
Non Final Office Action dated Apr. 2, 2008 from U.S. Appl. No. 11/674,839 filed on Feb. 14, 2007.
Response dated Sep. 25, 2008 to Non-Final Office Action dated Apr. 2, 2008 from U.S. Appl. No. 11/674,839 filed Feb. 14, 2007.
Non-Final Office Action dated May 8, 2008 from U.S. Appl.No. 11/359,846 filed Feb. 22, 2006.
Response dated Nov. 5, 2008 to Non-Final Office Action dated May 8, 2008 from U.S. Appl. No. 11/359,846 filed Feb. 22, 2006.
Notice of Allowance and Fee(s) Due dated Feb. 3, 2009 from U.S. Appl. No. 11/359,846 filed Feb. 22, 2006.
Notice of Allowance and Fee(s) Due dated Dec. 30, 2008 from U.S. Appl. No. 11/674,839 filed Feb. 14, 2007.
Non Final Office Action dated Apr. 2, 2008 from U.S. Appl. No. 11/742,612 filed on May 1, 2007.
Response dated Sep. 25, 2008 to Non-Final Office Action dated Apr. 2, 2008 from U.S. Appl. No. 11/742,612 filed May 1, 2007.
Notice of Allowance and Fee(s) Due dated Jan. 2, 2009 from U.S. Appl. No. 11/742,612 filed May 1, 2007.

* cited by examiner

PROCESSES FOR PREPARING OF GLUCOPYRANOSYL-SUBSTITUTED (ETHYNYL-BENZYL)-BENZENE DERIVATIVES AND INTERMEDIATES THEREOF

This application claims priority benefit to EP 05108487, filed Sep. 15, 2005, which is incorporated herewith in its entirety.

The present invention relates to processes for preparing of glucopyranosyl-substituted (ethynyl-benzyl)-benzene derivatives of the formula I,

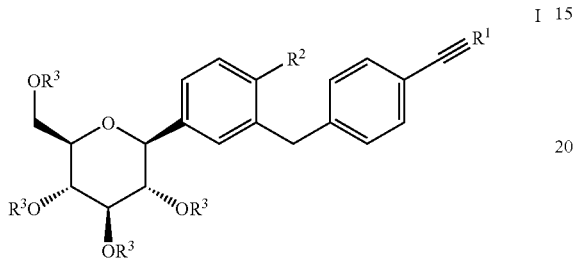

wherein the substituents $R^1$, $R^2$ and $R^3$ are defined as hereinafter. Furthermore the present invention relates to processes for preparing intermediates and starting materials of the processes according to this invention. In addition the present invention relates to such intermediates and starting materials.

BACKGROUND OF THE INVENTION

In the international patent application WO 2005/092877 glucopyranosyl-substituted benzene derivatives of the general formula

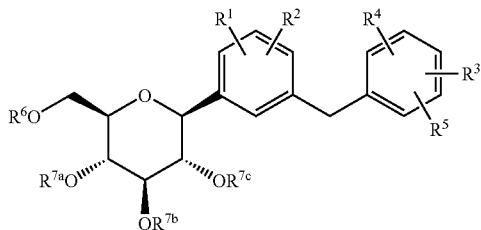

wherein the groups $R^1$ to $R^6$ and $R^{7a}$, $R^{7b}$, $R^{7c}$ are as defined therein, are described. Such compounds have a valuable inhibitory effect on the sodium-dependent glucose cotransporter SGLT, particularly SGLT2.

AIM OF THE INVENTION

The aim of the present invention is to find new processes for preparing of glucopyranosyl-substituted benzyl-benzene derivatives of the formula I; in particular processes with which the product may be obtained in high yields, high enantiomeric or diastereomeric purity and which allow the manufacture of the product in a commercial scale with a low technical expenditure and a high space/time yield.

Another aim of the present invention is to provide processes for preparing the starting materials of the beforementioned method of manufacture.

Further aims of the present invention relate to new intermediates and starting materials in the process according to the present invention.

Other aims of the present invention will become apparent to the skilled man directly from the foregoing and following description.

OBJECT OF THE INVENTION

In a first aspect the present invention relates to a process for preparing the compounds of general formula I,

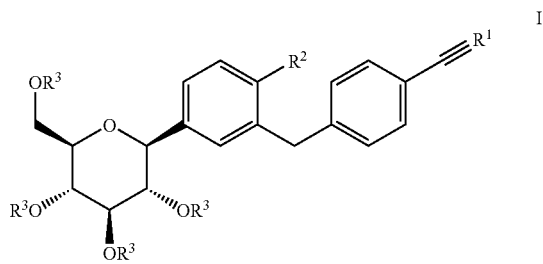

wherein $R^1$ denotes hydrogen, or $C_{1-4}$-alkyl, $C_{3-7}$-cycloalkyl, tetrahydrofuranyl, or tetrahydropyranyl, which may be substituted with one to four substituents L2, or an aryl-group or a 5- or 6-membered monocyclic heteroaryl-group or a 8-, 9- or 10-membered bicyclic heteroaryl-group wherein said heteroaryl-groups have 1 to 4 heteroatoms independently selected from the group consisting of N, O and S; and wherein said heteroaryl-group may possess 1 or 2 carbonyl groups as part of the mono- or bicyclic aromatic ring-system; and wherein an N-atom of the heteroaryl ring-system may be oxidized to form the corresponding N-oxide; and wherein one or more methine groups in said aryl- and heteroaryl-group may be substituted independently of one another with a substituent L1; and wherein one or more imino-groups in said heteroaryl-group may be substituted independently of one another with a substituent $R^N$; and $R^2$ denotes chlorine or methyl; and $R^3$ denotes hydrogen;

$R^N$ independently of one another are selected from among $C_{1-3}$-alkyl; and

L1 independently of one another are selected from among fluorine, chlorine, bromine, $C_{1-3}$-alkyl, $C_{1-4}$-alkoxy and nitro;

L2 independently of one another are selected from among fluorine, chlorine, hydroxy, hydroxyl-$C_{1-4}$-alkyl, $C_{1-4}$-alkoxy, trifluoromethoxy, $C_{1-4}$-alkoxy-$C_{1-4}$-alkyl, cyano, $C_{1-4}$-alkyl, trifluoromethyl, amino, $C_{1-4}$-alkyl-carbonylamino, $C_{1-3}$-alkyl-amino and di($C_{1-3}$-alkyl)-amino; and while by the aryl groups mentioned in the definition of the above groups are meant phenyl or naphthyl groups, preferably phenyl groups, which may be mono- or polysubstituted with L1;

characterised in that in a compound of general formula II

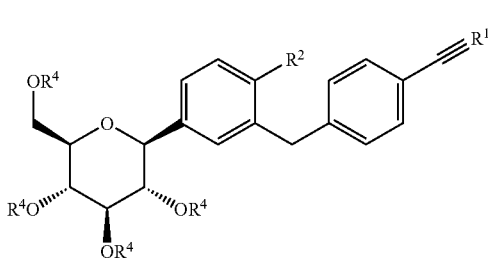

wherein $R^1$ and $R^2$ are defined as hereinbefore and
$R^4$ independently of one another denote hydrogen, $C_{3-18}$-alkenyl, $(C_{1-18}$-alkyl)carbonyl, $(C_{1-18}$-alkyl)oxycarbonyl, $(C_{3-18}$-alkenyl)carbonyl, $(C_{3-18}$-alkenyl)oxycarbonyl, di-$(C_{1-18}$-alkyl)aminocarbonyl, arylcarbonyl, aryl-$(C_{1-3}$-alkyl)-carbonyl, aryl-$C_{1-3}$-alkyl, $C_{1-6}$-alkoxymethyl, aryl-$C_{1-3}$-alkoxy, $C_{1-4}$-alkylthioethyl, arylthioethyl, $C_{1-4}$-alkylsulfonylethyl, arylsulfonylethyl, $R^aR^bR^cSi$—, —$CR^aR^bOR^c$, wherein two adjacent groups $R^4$ may be linked with each other to form a bridging group $SiR^aR^b$, C=O, $CR^aR^b$ or $CR^aOR^b$—$CR^aOR^b$ and wherein each alkyl group may be substituted with up to three substituents selected from fluorine, chlorine, $C_{1-3}$-alkyl, $R^aR^bR^cSi$, $C_{1-4}$-alkoxy, with the proviso that at least one substituent $R^4$ is not hydrogen;
$R^a$, $R^b$, $R^c$ independently of one another denote $C_{1-4}$-alkyl, aryl or aryl-$C_{1-3}$-alkyl, while the alkyl may be mono- or polysubstituted by halogen;
L1 and L2 are defined as hereinbefore; and
while by the aryl groups mentioned in the definition of the above groups are meant phenyl or naphthyl groups, preferably phenyl groups, which may be mono- or polysubstituted with L1;
the protective groups $R^4$ not being hydrogen are cleaved, in particular hydrolysed.

In a second aspect the present invention relates to a process for preparing the compounds of general formula II',

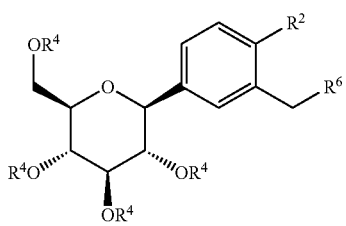

wherein
$R^1$ denotes hydrogen,
$C_{1-4}$-alkyl, $C_{3-7}$-cycloalkyl, tetrahydrofuranyl, or tetrahydropyranyl, which may be substituted with one to four substituents L2,
an aryl-group or a 5- or 6-membered monocyclic heteroaryl-group or a 8-, 9- or 10-membered bicyclic heteroaryl-group wherein said heteroaryl-groups have 1 to 4 heteroatoms independently selected from the group consisting of N, O and S; and wherein said heteroaryl-group may possess 1 or 2 carbonyl groups as part of the mono- or bicyclic aromatic ring-system; and
wherein an N-atom of the heteroaryl ring-system may be oxidized to form the corresponding N-oxide; and
wherein one or more methine groups in said aryl- and heteroaryl-group may be substituted independently of one another with a substituent L1; and
wherein one or more imino-groups in said heteroaryl-group may be substituted independently of one another with a substituent $R^N$; and
$R^2$ denotes chlorine or methyl; and
$R^3$ denotes hydrogen;
$R^4$ independently of one another denote hydrogen, $C_{3-18}$-alkenyl, $(C_{1-18}$-alkyl)carbonyl, $(C_{1-18}$-alkyl)oxycarbonyl, $(C_{3-18}$-alkenyl)carbonyl, $(C_{3-18}$-alkenyl)oxycarbonyl, di-$(C_{1-18}$-alkyl)aminocarbonyl, arylcarbonyl, aryl-$(C_{1-3}$-alkyl)-carbonyl, aryl-$C_{1-3}$-alkyl, $C_{1-6}$-alkoxymethyl, aryl-$C_{1-3}$-alkoxy, $C_{1-4}$-alkylthioethyl, arylthioethyl, $C_{1-4}$-alkylsulfonylethyl, arylsulfonylethyl, $R^aR^bR^cSi$, $CR^aR^bOR^c$, wherein two adjacent groups $R^4$ may be linked with each other to form a bridging group $SiR^aR^b$, C=O, $CR^aR^b$ or $CR^aOR^b$—$CR^aOR^b$ and wherein each alkyl group may be substituted with up to three substituents selected from fluorine, chlorine, $C_{1-3}$-alkyl, $R^aR^bR^cSi$, $C_{1-4}$-alkoxy,
$R^6$ denotes hydrogen, para-$R^7$-phenyl-, $C_{1-6}$-alkyloxy, aryloxy, —$OR^4$; and
$R^7$ denotes —C≡C—$R^1$, Cl, Br, I, —$OSO_2R$, —CHO, —$SiAlk_3$, —O—$C_{1-6}$-alkyl, —$OR^4$, —C≡C—$Si(C_{1-4}$-alkyl)$_3$, —C≡C—$Si(aryl)(C_{1-4}$-alkyl)$_2$, —C≡C—$Si(bi$-phenyl)$(C_{1-4}$-alkyl)$_2$, or —C≡C—$C(OH)(C_{1-4}$-alkyl)$_2$; and
R denotes $C_{1-4}$-alkyl, $C_{3-4}$-alkenyl, $C_{1-4}$-alkoxy, $CF_3$, aryl or aryl-$C_{1-3}$-alkyl, wherein aryl-groups may be mono- or polysubstituted with L1;
$R^a$, $R^b$, $R^c$ independently of one another denote $C_{1-4}$-alkyl, aryl or aryl-$C_{1-3}$-alkyl, while the alkyl groups may be mono- or polysubstituted by halogen;
$R^N$ independently of one another are selected from among $C_{1-3}$-alkyl; and
L1 independently of one another are selected from among fluorine, chlorine, bromine, $C_{1-3}$-alkyl, $C_{1-4}$-alkoxy and nitro;
L2 independently of one another are selected from among fluorine, chlorine, hydroxy, hydroxyl-$C_{1-4}$-alkyl, $C_{1-4}$-alkoxy, trifluoromethoxy, $C_{1-4}$-alkoxy-$C_{1-4}$-alkyl, cyano, $C_{1-4}$-alkyl, trifluoromethyl, amino, $C_{1-4}$-alkyl-carbonylamino, $C_{1-3}$-alkyl-amino and di($C_{1-3}$-alkyl)-amino; and
while by the aryl groups mentioned in the definition of the above groups are meant phenyl or naphthyl groups, preferably phenyl groups, which may be mono- or polysubstituted with L1;
characterised in that a compound of general formula III'

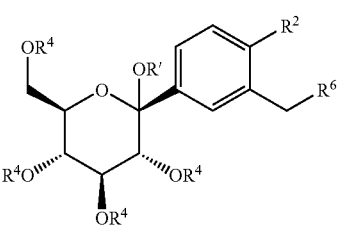

wherein $R^2$, $R^6$ and each $R^4$ are defined as hereinbefore and
R' denotes hydrogen, $C_{1-6}$-alkyl, $(C_{1-4}$-alkyl)carbonyl, $(C_{1-4}$-alkyl)oxycarbonyl, arylcarbonyl, aryl-$(C_{1-3}$-alkyl)-carbonyl;
while the term "aryl" is defined as hereinbefore;
is reacted with a reducing agent.

In a third aspect the present invention relates to a process for preparing the compounds of general formula III',

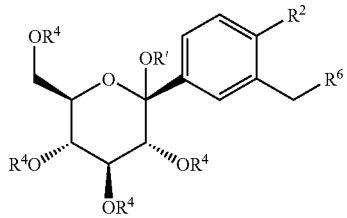

III' wherein $R^2$, R' and each $R^4$ are defined as hereinbefore; and
$R^6$ denotes hydrogen, para-$R^7$-phenyl-, $C_{1-6}$-alkyloxy, aryloxy, —$OR^4$; and
$R^7$ denotes —C≡C—$R^1$, Cl, Br, I, —$OSO_2R$, —CHO, —$SiAlk_3$, —O—$C_{1-6}$-alkyl, —$OR^4$, —C≡C—Si($C_{1-4}$-alkyl)$_3$, —C≡C—Si(aryl)($C_{1-4}$-alkyl)$_2$, —C≡C—Si(biphenyl)($C_{1-4}$-alkyl)$_2$, or —C≡C—C(OH)($C_{1-4}$-alkyl)$_2$; and
R denotes $C_{1-4}$-alkyl, $C_{3-4}$-alkenyl, $C_{1-4}$-alkoxy, $CF_3$, aryl or aryl-$C_{1-3}$-alkyl, wherein aryl-groups may be mono- or polysubstituted with L1;
wherein $R^1$, aryl and L1 are defined as hereinbefore;
characterised in that an organometallic compound of the formula VI

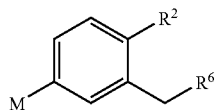

VI wherein $R^2$ and $R^6$ are defined as hereinbefore and M denotes Li or MgHal, wherein Hal denotes Cl, Br or I; and
or a derivative thereof obtained by transmetallation;
which compound of the formula VI may be obtained by halogen-metal exchange or by the insertion of a metal in the carbon-halogen bond of a halogen-benzylbenzene compound of general formula V

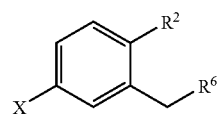

V wherein $R^2$ and $R^6$ are defined as hereinbefore and X denotes Cl, Br or I;
and optionally subsequent transmetallation,
is added to a gluconolactone of general formula IV

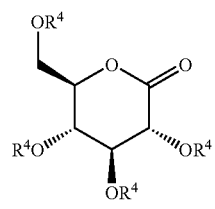

IV wherein $R^4$ is as hereinbefore defined,
then the adduct obtained is reacted with water or an alcohol R'—OH, where R' denotes $C_{1-6}$-alkyl, in the presence of an acid and optionally the product obtained in the reaction with water wherein R' denotes H is converted in a subsequent reaction with an acylating agent into the product of formula III' wherein R' denotes ($C_{1-4}$-alkyl)carbonyl, ($C_{1-4}$-alkyl)oxycarbonyl, arylcarbonyl, or aryl-($C_{1-3}$-alkyl)-carbonyl, wherein the term "aryl" is defined as hereinbefore.

In a fourth aspect the present invention relates to a process for preparing the compounds of general formula X,

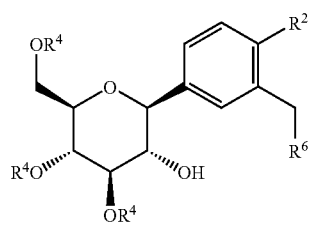

X wherein $R^2$, $R^6$ and each $R^4$ are defined as hereinbefore;
characterised in that a protected D-glucal of the formula VII

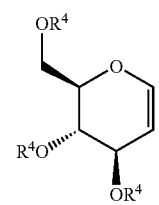

VII wherein $R^4$ is defined as hereinbefore;
is metallated to yield a metallated D-glucal of the formula VIII

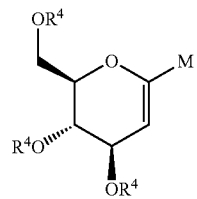

VIII wherein $R^4$ is defined as hereinbefore and M denotes lithium or a magnesium moiety;
which is optionally transmetallated to yield a metallated D-glucal of the formula VIII, wherein M denotes a magnesium, zinc, indium, boron, tin, silicon or chromium moiety; and
the metallated or trans-metallated D-glucal of the formula VIII is reacted with an aglycon of the formula V

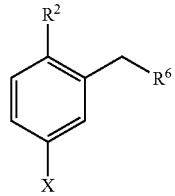

V wherein $R^2$ and $R^6$ are defined as hereinbefore and X denotes a replaceable group;

in the presence of a transition metal catalyst to yield a glucal derivative of the formula IX

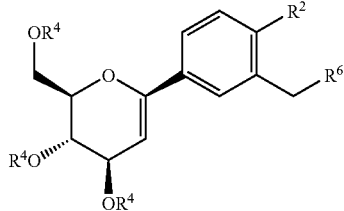

IX wherein $R^2$, $R^6$ and each $R^4$ are defined as hereinbefore; and the glucal derivative of the formula IX is converted to the product of the formula X by the (formal) addition of water to the double bond of the glucal moiety, in particular by hydroboration of the double bond and subsequent oxidative cleavage of the carbon-boron bond or by epoxidation or dihydroxylation of the double bond and subsequent reduction of the resultant anomeric carbon-oxygen bond.

In a fifth aspect the present invention relates to a process for preparing a compound of the general formula X

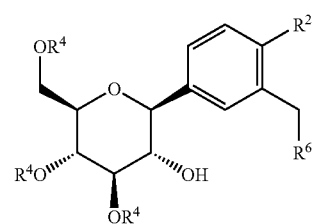

X wherein $R^2$, $R^6$ and each $R^4$ are defined as hereinbefore;

characterised in that a protected D-glucal of the formula VII

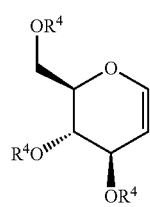

VII wherein $R^4$ is defined as hereinbefore;

is epoxidated to yield the corresponding glucaloxide of the formula XI

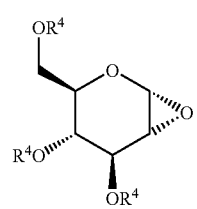

XI wherein $R^4$ is defined as hereinbefore; and the glucaloxide of the formula XI is reacted with an aglycon of the formula VI

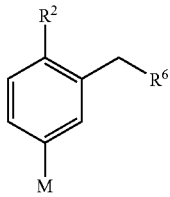

VI wherein $R^2$ and $R^6$ is defined as hereinbefore and M denotes a lithium, magnesium, zinc, indium, aluminum or boron moiety;

to yield the product of the formula X.

In a sixth aspect the present invention relates to a process for preparing a compound of compound of the general formula II',

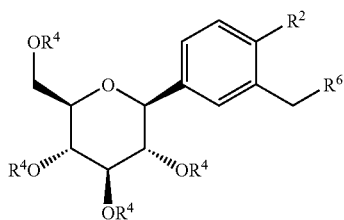

II' wherein $R^2$, $R^6$ and each $R^4$ are defined as hereinbefore;

characterised in that a glucose derivative of the formula XII

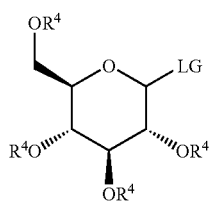

XII wherein $R^4$ is defined as hereinbefore and

LG denotes F, Cl, Br, $C_{1-3}$-alkylcarbonyloxy, $C_{1-3}$-alkyloxycarbonyloxy, $C_{1-3}$-alkyloxy or trichloroacetimidate;

is reacted with a metallated aglycon of the formula VI

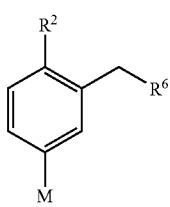

VI wherein $R^2$ is defined as hereinbefore; and $R^6$ is defined as hereinbefore; and M denotes a lithium, magnesium, zinc, indium or boron moiety;

to yield the product of the formula II'.

In a seventh aspect the present invention relates to a process for preparing a compound of the formula XXVI'

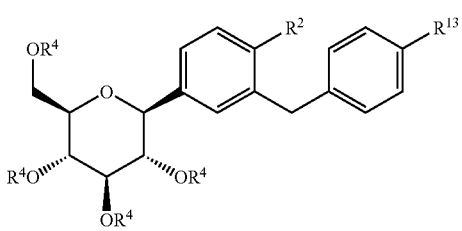

wherein $R^2$ and $R^4$ are defined as hereinbefore; and
$R^{13}$ denotes —CHO, —C≡C—$R^1$, OH, $C_{1-6}$-alkyloxy, —Si($C_{1-6}$-alkyl)$_3$, —C≡C—Si($C_{1-4}$-alkyl)$_3$, —C≡C—Si(aryl)($C_{1-4}$-alkyl)$_2$, —C≡C—Si(biphenyl)($C_{1-4}$-alkyl)$_2$, —C≡C—C(OH)($C_{1-4}$-alkyl)$_2$, iodine, bromine, chlorine, or $C_{1-6}$-alkylsulfonyloxy; wherein $R^1$ is defined as hereinbefore;
characterized in that
in a compound of the formula X

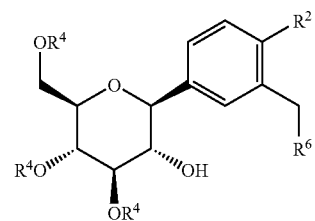

wherein $R^2$ and each $R^4$ are defined hereinbefore; and
$R^6$ denotes hydrogen, OH, $C_{1-6}$-alkyloxy or aryloxy
or in a compound of the formula II'

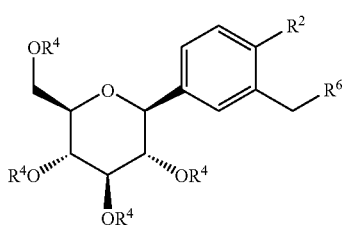

wherein $R^2$, $R^6$ and each $R^4$ are defined as hereinbefore.
the group $R^6$ is optionally transformed into a group $Z^4$ to yield a compound of the formula XXXIX

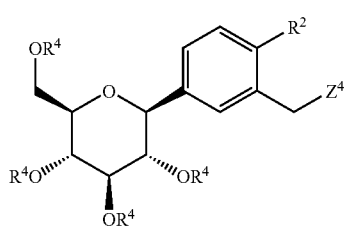

wherein $R^2$ and each $R^4$ are defined as hereinbefore; and $Z^4$ denotes chlorine, bromine, iodine, $C_{1-6}$-alkyloxy, aryloxy, $C_{1-6}$-alkylcarbonyl-oxy, $C_{1-6}$-alkyloxycarbonyloxy, $C_{1-6}$-alkylsulfonyloxy, —OPO(O—$C_{1-6}$-alkyl)$_2$, or aryloxy;
and the compound of the formula XXXIX is reacted with a metalated benzene of the formula XXIII

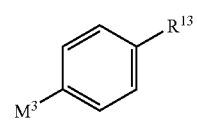

wherein $R^{13}$ is defined as hereinbefore; and
$M^3$ denotes a lithium-, boron-, magnesium-, silicon-, tin-, cerium-, indium-, zinc-, or chromium-moiety;
to yield a compound of the formula XXVI'.
Further aspects of the present invention relate to new compounds, in particular new educts and intermediates, in particular of the formulae II, II', IX and X, as described in the processes for manufacture according to the present invention.

DETAILED DESCRIPTION OF THE INVENTION

Unless otherwise stated, the groups, residues and substituents, particularly $R^1$, $R^2$, $R^3$, $R^4$, L1, L2, $R^N$, are defined as above and hereinafter.
If residues, substituents or groups, for example such as Alk, L1, L2, $R^2$ or $R^4$, occur several times in a compound, they may have the same or different meanings.
In the processes and compounds according to this invention as described hereinbefore and hereinafter the following meanings of groups and substituents are preferred:
$R^1$ preferably denotes hydrogen or
$C_{1-4}$-alkyl, cyclopropyl, cyclobutyl, cyclopentyl, cyclohexyl, tetrahydrofuranyl and tetrahydropyranyl, which may be substituted with one to four substituents L2; or
an optionally substituted aryl-group or an optionally substituted 5- or 6-membered monocyclic heteroaryl-group.
Even more preferably $R^1$ denotes hydrogen or $C_{1-4}$-alkyl, cyclopropyl, cyclobutyl, cyclopentyl, cyclohexyl, tetrahydrofuranyl or tetrahydropyranyl, which may be substituted with one or two substituents L2.
Preferred substituents L2 are independently of each other selected from hydroxy, hydroxyl-$C_{1-4}$-alkyl, $C_{1-4}$-alkyl, $C_{1-4}$-alkoxy and $C_{1-4}$-alkoxy-$C_{1-4}$-alkyl. Examples of preferred meanings of L2 are hydroxy, hydroxymethyl, methyl, methoxymethyl, methoxy and ethoxy.
$R^2$ preferably denotes chlorine or methyl.
Particularly preferred meanings of group $R^4$ are hydrogen, methoxycarbonyl, methylcarbonyl or ethylcarbonyl.
$R^a$, $R^b$, $R^c$ independently of one another preferably denote methyl, ethyl, n-propyl or i-propyl, tert-butyl or phenyl.
R' preferably denotes hydrogen, methyl or ethyl.
In the following the processes according to this invention are described in detail. The reaction conditions such as reagents, catalysts, solvents, and temperature given are meant to provide preferred ranges and examples for the respective transformation that can be principally applied but are not supposed to restrict them to the selection given. In addition, the reaction parameters are usually given independently of each other. The skilled one in the art knows or can determine by standard experimentation which combination of parameters is especially advantageous.
In the following schemes
Alk denotes $C_{1-4}$-alkyl,
Ar denotes aryl as defined hereinbefore, preferably phenyl;

R denotes $C_{1-4}$-alkyl, $C_{3-4}$-alkenyl, $C_{1-4}$-alkoxy, $CF_3$, aryl or aryl-$C_{1-3}$-alkyl, wherein aryl-groups may be mono- or polysubstituted with L1;
$R^1$ is as defined hereinbefore; and
$R^2$ is as defined hereinbefore; and
$R^3$ is as defined hereinbefore; and
$R^4$ is as defined hereinbefore; and
$R^6$ denotes hydrogen, para-$R^7$-phenyl-, $C_{1-6}$-alkyloxy, aryloxy, —$OR^4$; and
$R^7$ denotes —C≡C—$R^1$, Cl, Br, I, —$OSO_2R$, —CHO, —$SiAlk_3$, —O—$C_{1-6}$-alkyl, —$OR^4$, —C≡C—$SiAlk_3$, —C≡C—$SiArAlk_2$, —C≡C—Si(biphenyl)$Alk_2$, —C≡C—C(OH)$Alk_2$;
X denotes chlorine, bromine, iodine or $OSO_2R$,
Y denotes

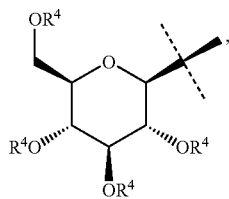

X, OAlk, $SiAlk_3$,
L1 is as defined hereinbefore.

The Scheme 1 depicts the conversion of compound II to compound I according to the first aspect of this invention via removal of the protective groups $R^4$ not being hydrogen present in compound II, wherein $R^1$, $R^2$, $R^3$ and $R^4$ are defined as hereinbefore.

Scheme 1: Synthesis of C-glucoside of formula I via removal of protective groups

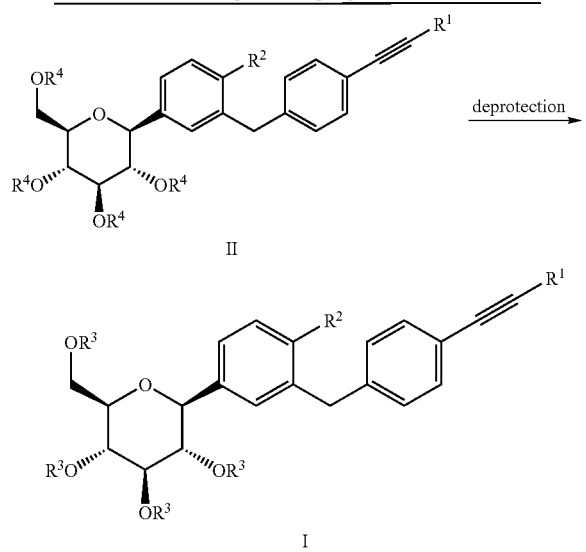

Preferred meanings of the group $R^4$ are hydrogen, ($C_{1-6}$-alkyl)carbonyl, ($C_{1-6}$-alkyl)oxycarbonyl, ($C_{3-6}$-alkenyl)oxycarbonyl, arylcarbonyl, aryl-methyl, $C_{1-6}$-alkoxymethyl, $R^aR^bR^cSi$, $CR^aR^bOR^c$, wherein two adjacent groups $R^4$ may be linked with each other to form a bridging group $SiR^aR^b$, C=O, $CR^aR^b$ or $CR^aOR^b$—$CR^aOR^b$ and wherein each alkyl group may be substituted with up to three substituents selected from fluorine, chlorine, $C_{1-3}$-alkyl, $R^aR^bR^cSi$ and $C_{1-4}$-alkoxy.

Any acyl protecting group $R^4$ can be cleaved for example hydrolytically in water or a mixture of one or more organic solvents with water, e.g. in water, isopropanol/water, acetic acid/water, tetrahydrofuran/water or dioxane/water, in the presence of an acid such as trifluoroacetic acid, hydrochloric acid or sulfuric acid or in the presence of an alkali metal base such as lithium hydroxide, sodium hydroxide or potassium hydroxide. The reaction is preferably carried out in a temperature range between −30° C. and 120° C., more preferably between 10 and 100° C.

Any acetal or ketal protecting group $R^4$ can be cleaved for example hydrolytically in solvents such as e.g. water, isopropanol, acetic acid, tetrahydrofuran, dioxane or mixtures thereof in the presence of an acid such as e.g. trifluoroacetic acid, hydrochloric acid or sulfuric acid or aprotically, e.g. in the presence of iodotrimethylsilane or bromotrimethylsilane. The reaction is preferably carried out at temperatures between 30° C. and 120° C., more preferably between 10 and 100° C.

A trimethylsilyl group $R^4$ can be cleaved for example in water, an aqueous solvent mixture or a lower alcohol such as methanol or ethanol in the presence of a base such as lithium hydroxide, sodium hydroxide, potassium carbonate or sodium methoxide. In aqueous or alcoholic solvents, acids such as e.g. hydrochloric acid, trifluoroacetic acid, methanesulfonic acid or acetic acid are also suitable. For cleaving in organic solvents, such as for example diethyl ether, tetrahydrofuran or dichloromethane, it is also suitable to use fluoride reagents, in particular tetraalkylammonium fluorides or alkaline metal fluorides, such as e.g. tetrabutylammonium or cesium fluoride.

Silyl protective groups, especially with substituents larger than methyl, such as e.g. triethylsilyl, tert-butyldimethylsilyl, methyldiphenylsilyl, triphenylsilyl, diisopropylsilyl, or triisopropylsilyl can be removed with acids such as e.g. hydrochloric acid, sulfuric acid, alkylsulfonic acids, acetic acid, trifluoroacetic acid, particularly in inert organic solvents, water or mixtures thereof, such as alcohols such as e.g. methanol or ethanol, water, tetrahydrofuran, dioxane, acetonitrile or mixtures thereof. The reaction is preferably carried out at temperatures in a range from −80° C. to 100° C., more preferably from 0° C. to 60° C. Fluoride reagents such as e.g. hydrogen fluoride, tetrabutylammonium fluoride, pyridinium fluoride, potassium or cesium fluoride may also be applied in suitable organic solvents, such as e.g. tetrahydrofuran, acetonitrile, or dioxane. Basic conditions such as the use of sodium or potassium hydroxide in tetrahydrofuran, dioxane, alcohols, water or mixtures thereof may be applied as well.

An arylmethyl or arylmethoxycarbonyl group $R^4$ is advantageously cleaved hydrogenolytically, e.g. with hydrogen in the presence of a catalyst such as palladium/charcoal in a suitable inert organic solvent such as methanol, ethanol, ethyl acetate or glacial acetic acid, optionally in the presence of an acid such as hydrochloric acid. The reaction is preferably carried out at temperatures between 0 and 100° C., more preferably at temperatures between 20 and 60° C. Usually a hydrogen pressure in a range from 1 to 7 bar is advantagous; a preferred range is between 3 to 5 bar. Electron rich arylmethyl groups such as e.g. 2,4-dimethoxybenzyl group may also be cleaved in tri-fluoroacetic acid in the presence of an arylmethyl cation scavenger such as e.g. anisole.

A tert-butyl or tert-butyloxycarbonyl group $R^4$ is preferably cleaved by treating with an acid such as trifluoroacetic acid or hydrochloric acid. The reaction is preferably carried out in an inert organic solvent, such as methylene chloride, dioxane, methanol, isopropanol, diethylether or mixture thereof.

Scheme 2a outlines a synthetic route to access compounds of the formula II' according to the $2^{nd}$ aspect of the present invention. The glucose derivative of formula II' is obtained via the isolable intermediate III' that may be produced according to the third aspect of the present invention (see Scheme 2b).

Scheme 2a: Synthesis of C-Glycosides - Approach 1

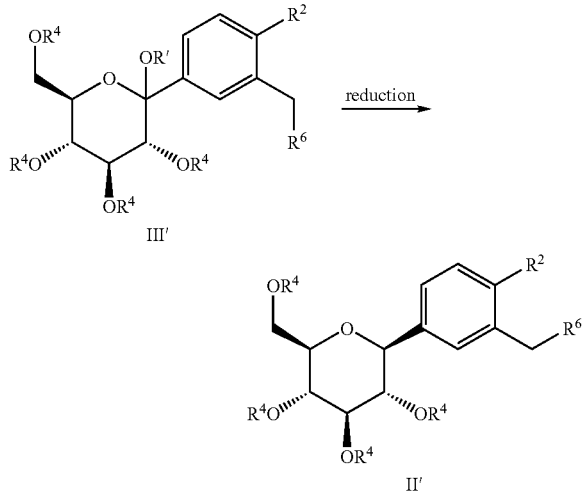

Preferred meanings of the group $R^6$ are H, O—$C_{1-6}$-alkyl, O-aryl, para-$R^7$-phenyl and $OR^4$ wherein aryl and $R^4$ are as defined hereinbefore.

$R^7$ preferably denotes —C≡C—$R^1$, Cl, —$OSO_2R$, —$SiAlk_3$, —C≡C—$SiAlk_3$, —C≡C—$SiArAlk_2$, —C≡C—Si(biphenyl)$Alk_2$ wherein $R^1$, R, Ar, Alk and $R^4$ are as defined hereinbefore.

According to a preferred embodiment $R^6$ denotes O—$C_{1-6}$-alkyl, O-aryl and para-$R^7$-phenyl- wherein aryl is as defined hereinbefore and $R^7$ preferably denotes —C≡C—$R^1$, —$SiMe_3$, —C≡C—$SiAlk_3$, —C≡C—$SiArAlk_2$, —C≡C—Si(biphenyl)$Alk_2$ wherein $R^1$, Ar and Alk are as defined hereinbefore.

According to an alternative embodiment, which is also preferred, $R^6$ denotes H, O—$C_{1-6}$-alkyl, O-aryl, $C_{1-4}$-alkyl-carbonyloxy, $C_{1-4}$-alkyloxycarbonyloxy or para-$R^7$-phenyl-, wherein aryl is as defined hereinbefore, and wherein $R^7$ preferably denotes —$OSO_2R$, —$SiAlk_3$, —C≡C—$SiAlk_3$, —C≡C—$SiArAlk_2$, or —C≡C—Si(biphenyl)$Alk_2$; wherein Ar and Alk are as defined hereinbefore and R denotes $C_{1-4}$-alkyl, $CF_3$, aryl or aryl-$C_{1-3}$-alkyl, wherein aryl-groups may be mono- or polysubstituted with L1.

Preferred definitions of the substituents $R^4$ in Scheme 2a are ($C_{1-6}$-alkyl)-carbonyl wherein the alkyl group may be substituted with $C_{1-4}$-alkoxy, ($C_{1-6}$-alkyl)-oxycarbonyl, ($C_{3-6}$-alkenyl)oxycarbonyl, di-($C_{1-6}$-alkyl)aminocarbonyl, arylcarbonyl, $R^aR^bR^cSi$—, —$CR^aR^bOR^c$, benzyl, substituted benzyl; particularly preferably trimethylsilyl, triisopropylsilyl, $C_{1-4}$-alkoxymethyl, 4-methoxybenzyl and benzyl; wherein $R^a$, $R^b$, $R^c$ are defined as above and preferably denote $C_{1-3}$-alkyl. If two adjacent substituents $R^4$ are linked together to form a bridging group $SiR^aR^b$, C=O, $CR^aR^b$ or $CR^aOR^b$—$CR^aOR^b$; and wherein each alkyl group may be substituted with up to three substituents selected from fluorine, chlorine, $C_{1-3}$-alkyl, $R^aR^bR^cSi$, $C_{1-4}$-alkoxy. In particular if two adjacent substituents $R^4$ are linked together these two substituents are preferably part of a benzylideneacetal, 4-methoxybenzylideneacetal, diisopropylsilylideneacetal, isopropylketal or constitute a dioxane with 2,3-dimethoxybutylene which is linked via the 2 and 3 positions of the butane with the adjacent oxygen atoms of the pyranose.

The group R' preferably denotes hydrogen, $C_{1-4}$-alkyl, $C_{1-4}$-alkylcarbonyl or $C_{1-4}$-alkyloxycarbonyl, particularly preferably hydrogen, methyl or ethyl.

The synthetic transformation presented in Scheme 2a shows the formation of the glucose derivative of formula II' via reduction of the anomeric carbon-oxygen bond in compound III'. The reduction may be conducted with a reducing agent in the presence of or without a Lewis acid. Suitable reducing agents include for example silanes such as e.g. triethyl, tripropyl, triisopropyl, or diphenylsilane, sodium borohydride, sodium cyanoborohydride, zinc borohydride, borane complexes, lithium aluminum hydride, diisobutylaluminum hydride, or samarium iodide. Depending on the reducing agent the reductions may be carried out without an additional Lewis acid. Suitable Lewis acids are Brønsted acids such as e.g. hydrochloric acid, toluenesulfonic acid, trifluoroacetic acid, or acetic acid, or Lewis acids such as e.g. boron trifluoride etherate, trimethylsilyl triflate, titanium tetrachloride, tin tetrachloride, scandium triflate, copper(II) triflate, or zinc iodide. Depending on the reducing agent and the Lewis acid employed the reaction may be carried out in a solvent such as for example methylene chloride, chloroform, acetonitrile, toluene, hexane, diethylether, tetrahydrofuran, dioxane, ethanol, water, or mixtures thereof. The reaction is preferably carried out at temperatures between −80° C. and 120° C., more preferably between −30 and 80° C. One particularly suitable combination of reagents consists for example of triethylsilane and boron trifluoride etherate, which is conveniently used in acetonitrile, dichloromethane, or mixtures thereof at temperatures of −60° C. to 60° C. In addition to the reducing agents mentioned above, hydrogen may be used for the reduction intended. This transformation may be accomplished in the presence of a transition metal catalyst such as e.g. palladium on charcoal, palladium oxide, platinum oxide, or Raney nickel, in solvents such as e.g. tetrahydrofuran, ethyl acetate, methanol, ethanol, water, or acetic acid. The reaction is preferably carried out at temperatures of −40° C. to 100° C. A preferred range of the hydrogen pressure is from about 1 to 10 Torr.

According to a preferred 1$^{st}$ variant of the 2$^{nd}$ aspect of the present invention the group $R^6$ denotes a group of the subformula

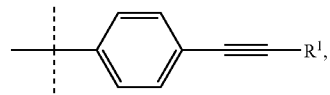

wherein $R^1$ is defined as hereinbefore. The glucose derivative of the formula II' which then corresponds to the compound II is obtained from the intermediate III' which then corresponds to the intermediate III according to the following scheme:

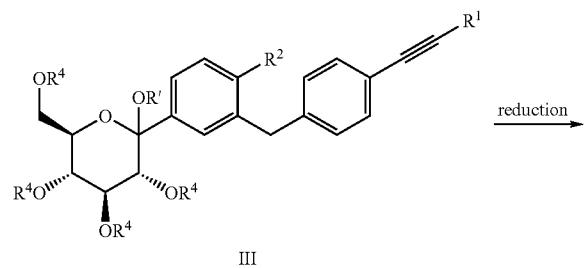

-continued

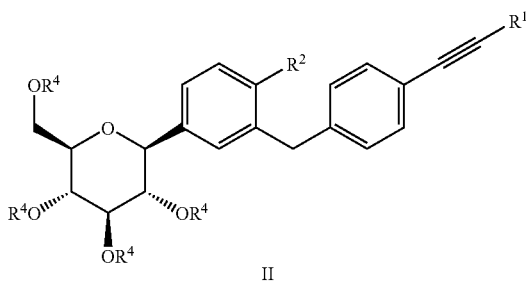

II

Starting from the glucose derivative of the formula II the protecting groups $R^4$ can be cleaved in order to obtain the product of the formula I. Suitable methods for cleaving protecting groups are well-known to the one skilled in the art and are described with respect to Scheme 1.

According to a $2^{nd}$ variant of the $2^{nd}$ aspect of the present invention the group $R^6$ denotes para-$R^7$-phenyl-, wherein $R^7$ denotes —C≡C—Si($C_{1-4}$-alkyl)$_3$, —C≡C—Si(aryl)($C_{1-4}$-alkyl)$_2$, —C≡C—Si(biphenyl)($C_{1-4}$-alkyl)$_2$, or —C≡C—C(OH)($C_{1-4}$-alkyl)$_2$. The resulting glucose derivative of the formula II' can be transformed for example by removal of the protective group at the distal end of the triple bond to yield a product of the formula II wherein $R^1$ denotes hydrogen. Those products of the formula II wherein $R^1$ is defined as above but does not denote hydrogen can be obtained by methods well known to the one skilled in the art, in particular by methods as described with respect to the scheme 13.

According to a $3^{rd}$ variant of the $2^{nd}$ aspect of the present invention the group $R^6$ denotes para-$R^7$-phenyl-, wherein $R^7$ denotes Cl, Br, I, —SiAlk$_3$, or —OSO$_2$R, wherein R denotes $C_{1-4}$-alkyl, CF$_3$ or aryl, wherein aryl-groups may be mono- or polysubstituted with L1. The resulting glucose derivative of the formula II' can be transformed to a product of the formula II for example by attaching an alkyne residue to the distal phenyl group by methods well-known to the one skilled in the art, in particular by methods as described with respect to the scheme 13.

According to a $4^{th}$ variant of the $2^{nd}$ aspect of the present invention the group $R^6$ denotes $C_{1-6}$-alkyloxy or aryloxy, wherein aryl is defined as hereinbefore. The resulting glucose derivative of the formula II' can be transformed to a product of the formula II for example by transforming $R^6$ into a leaving group such as chlorine, bromine and iodine and attaching the outer para-substituted phenyl group to the resultant compound by methods well-known to the one skilled in the art, in particular by methods with respect to the schemes 6, 12 and 15.

Preferred meanings of the protective groups $R^4$ according to this variant are selected from the group consisting of ($C_{1-6}$-alkyl)-carbonyl wherein the alkyl group is substituted with $C_{1-4}$-alkoxy, ($C_{1-6}$-alkyl)-oxycarbonyl, ($C_{3-6}$-alkenyl)carbonyl, ($C_{3-6}$-alkenyl)oxycarbonyl, di-($C_{1-6}$-alkyl)aminocarbonyl, arylcarbonyl, $R^aR^bR^cSi$— or —$CR^aR^bOR^c$; or two adjacent groups $R^4$ may be linked with each other to form a bridging group $SiR^aR^b$, C=O, $CR^aR^b$ or $CR^aOR^b$—$CR^aOR^b$; and wherein each alkyl group may be substituted with up to three substituents selected from fluorine, chlorine, $C_{1-3}$-alkyl, $R^aR^bR^cSi$, $C_{1-4}$-alkoxy.

According to a $5^{th}$ variant of the $2^{nd}$ aspect of the present invention the group $R^6$ denotes H or —$OR^4$; wherein $R^4$ is defined as hereinbefore. $R^6$ preferably denotes H, $C_{1-4}$-alkylcarbonyloxy or $C_{1-4}$-alkoxycarbonyloxy; even more preferably H. The resulting glucose derivative of the formula II' can be transformed to a product of the formula II for example by replacing $R^6$ with the distal para-substituted phenyl group via the corresponding brominated derivative ($R^6$=Br) by methods well-known to the one skilled in the art, in particular by methods with respect to the schemes 6, 12 and 15.

Scheme 2b outlines a synthetic route to access the intermediate of the formula III' that is produced by addition of a metallated aglycon VI to the gluconolactone IV according to the $3^{rd}$ aspect of the present invention Scheme 2b: Synthesis of C-Glucosides - Approach 1

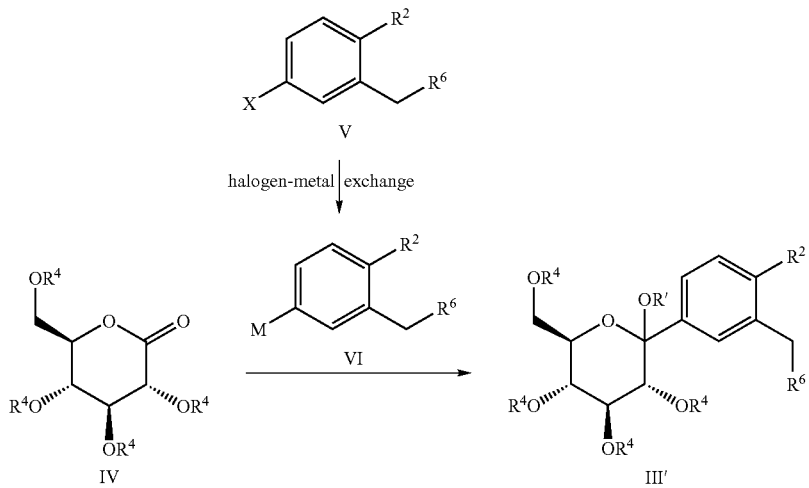

Preferred meanings of the group $R^6$ are H, O—$C_{1-6}$-alkyl, O-aryl, para-$R^7$-phenyl and $OR^4$ wherein aryl and $R^4$ are as defined hereinbefore. $R^7$ preferably denotes —C≡C—$R^1$, Cl, —$OSO_2R$, —$SiAlk_3$, —C≡C—$SiAlk_3$, —C≡C—$SiAr$-$Alk_2$, —C≡C—$Si(biphenyl)Alk_2$ wherein $R^1$, R, Ar, Alk and $R^4$ are as defined hereinbefore.

According to a preferred embodiment $R^6$ denotes O—$C_{1-6}$-alkyl, 0-aryl and para-$R^7$-phenyl- wherein aryl is as defined hereinbefore and $R^7$ preferably denotes —C≡C—$R^1$, —$SiMe_3$, —C≡C—$SiAlk_3$, —C≡C—$SiArAlk_2$, —C≡C—$Si(biphenyl)Alk_2$ wherein $R^1$, Ar and Alk are as defined hereinbefore.

According to an alternative embodiment, which is also preferred, $R^6$ denotes H, O—$C_{1-6}$-alkyl, O-aryl, $C_{1-4}$-alkylcarbonyloxy, $C_{1-4}$-alkyloxycarbonyloxy or para-$R^7$-phenyl-, wherein aryl is as defined hereinbefore, and wherein $R^7$ preferably denotes —$OSO_2R$, —$SiAlk_3$, —C≡C—$SiAlk_3$, —C≡C—$SiArAlk_2$, or —C≡C—$Si(biphenyl)Alk_2$; wherein Ar and Alk are as defined hereinbefore and R denotes $C_{1-4}$-alkyl, $CF_3$, aryl or aryl-$C_{1-3}$-alkyl, wherein aryl-groups may be mono- or polysubstituted with L1.

Preferred definitions of the substituents $R^4$ in Scheme 2 are benzyl, substituted benzyl, trialkylsilyl, $C_{1-4}$-alkoxymethyl, particularly preferably trimethylsilyl, triisopropylsilyl, $C_{1-4}$-alkoxymethyl, 4-methoxybenzyl and benzyl. If two adjacent substituents $R^4$ are linked together, these two substituents are preferably part of a benzylideneacetal, 4-methoxybenzylideneacetal, diisopropylsilylideneacetal, isopropylketal or constitute a dioxane with 2,3-dimethoxy-butylene which is linked via the 2 and 3 positions of the butane with the adjacent oxygen atoms of the pyranose. The group R' preferably denotes hydrogen, $C_{1-4}$-alkyl, $C_{1-4}$-alkylcarbonyl or $C_{1-4}$-alkyloxycarbonyl, particularly preferably hydrogen, methyl or ethyl.

The Grignard (M denotes MgBr, MgI) or lithiated (M denotes Li) reagent VI derived from the brominated or iodinated benzene derivative V (wherein X denotes Br or I) may be prepared either via a so-called halogen-metal exchange reaction or by inserting the metal into the carbon-halogen bond. The halogen-metal exchange to synthesize the corresponding lithium compound VI may be carried out for example with an organolithium compound such as e.g. n-, sec- or tert-butyllithium. The analogous magnesium compound may also be generated by a halogen-metal exchange with a suitable Grignard reagent such as e.g. isopropyl or sec-butyl magnesium bromide or chloride or diisopropyl or sec-butylmagnesium without or in the presence of an additional salt such as e.g. lithium chloride or co-solvent such as dioxane that may accelerate the metalation (see e.g. *Angew. Chem*. 2004, 116, 3396-3399 and *Angew. Chem*. 2005, 117, 165-169 and references quoted therein). The use of ate complexes of magnesium such as $Bu_3MgLi$ may also be possible (see *Tetrahedron Lett*. 2001, 42, 4841-4844 and *Angew. Chem*. 2000, 112, 2594-2596 and references quoted therein). The halogen-metal exchange reactions are preferably carried out between –100° C. and 40° C., particularly preferably between –80° C. and 10° C., in an inert solvent or mixtures thereof, such as for example diethylether, dioxane, tetrahydrofuran, toluene, and hexane. The magnesium or lithium derivatized compounds thus obtained may optionally be transmetalated with metal salts such as e.g. cerium trichloride, zinc chloride or bromide, indium chloride or bromide, to form alternative organometal compounds (VI) suitable for addition. Alternatively, the organometal compound VI may also be prepared by inserting a metal into the carbon-halogen bond of the haloaromatic compound V (X denotes Cl, Br, I). Lithium or magnesium as elemental metals are suitable for this transformation. The insertion can be achieved in inert organic solvents such as e.g. diethylether, dioxane, tetrahydrofuran, toluene, hexane, dimethylsulfoxide and mixtures thereof. The reaction is preferably carried out at temperatures ranging from –80 to 100° C., preferably at –70 to 40° C. In cases in which no spontaneous reaction takes place prior activation of the metal might be necessary such as e.g. the treatment with 1,2-dibromoethane, iodine, trimethylsilyl chloride, acetic acid, hydrochloric acid and/or sonication. The addition of the organometal compound VI to gluconolactone or derivatives thereof (IV) is preferably carried out at temperatures between –100° C. and 40° C., particularly preferably at –80 to 0° C., in an inert solvent or mixtures thereof, to obtain the compound of formula III'. All foregoing reactions may be performed in air though the execution under inert gas atmosphere such as argon and nitrogen is preferred. The metalation and/or coupling reaction may also be carried out in microreactors and/or micromixers which enable high exchange rates; for example analogously to the processes described in WO 2004/076470. Suitable solvents for the addition of the metalated phenyl group VI to the appropriately protected gluconolactone IV may be e.g. diethylether, toluene, methylene chloride, hexane, tetrahydrofuran, dioxane, N-methylpyrrolidone and mixtures thereof. The addition reactions may be carried out without any further adjuvant or in the case of sluggishly reacting coupling partners in the presence of a promoter such as e.g. $BF_3*OEt_2$ or $Me_3SiCl$ (see M. Schlosser, Organometallics in Synthesis, John Wiley & Sons, Chichester/New York/Brisbane/Toronto/Singapore, 1994). The group R' is introduced after the addition of the organometalic compound VI or a derivative thereof to the gluconolactone IV. If R' equals hydrogen or $C_{1-4}$-alkyl the reaction solution is treated with an alcohol R'—OH such as e.g. methanol or ethanol or water in the presence of an acid such as e.g. acetic acid, methanesulfonic acid, toluenesulfonic acid, sulfuric acid, trifluoroacetic acid, or hydrochloric acid. R' may also be attached after preparation of the hydrogen compound III' (R' denotes H) by reacting the compound under acidic conditions in the presence of an alcohol R'—OH such as methanol or ethanol. Alkylation or acylation of the anomeric hydroxyl group in III' with a suitable electrophile such as e.g. methyl iodide, dimethyl sulfate, ethyl iodide, diethyl sulfate, acetyl chloride, or acetic anhydride in the presence of a base such as e.g. triethylamine, ethyldiisopropylamine, sodium or potassium or cesium carbonate, sodium or potassium or cesium hydroxide may also be feasible. The hydroxyl group can also be deprotonated prior to the addition of the electrophile with e.g. sodium hydride.

Approach 2 depicted in Scheme 3 illustrates the synthesis of the C-glucosides commencing with the metallation of a protected D-glucal VII according to the $4^{th}$ aspect of the present invention. The resulting metallated D-glucal VIII may be transmetallated. The metallated or trans-metallated D-glucal of the formula VIII is coupled with an aglycon V in the presence of a transition metal catalyst to yield a glucal derivative of the formula IX which is converted to the product of the formula X by the formal addition of water to the double bond of the glucal moiety, in particular by hydroboration of the double bond and subsequent cleavage of the carbon-boron bond or by epoxidation or dihydroxylation of the double bond and subsequent reduction of the resultant anomeric carbon-oxygen bond.

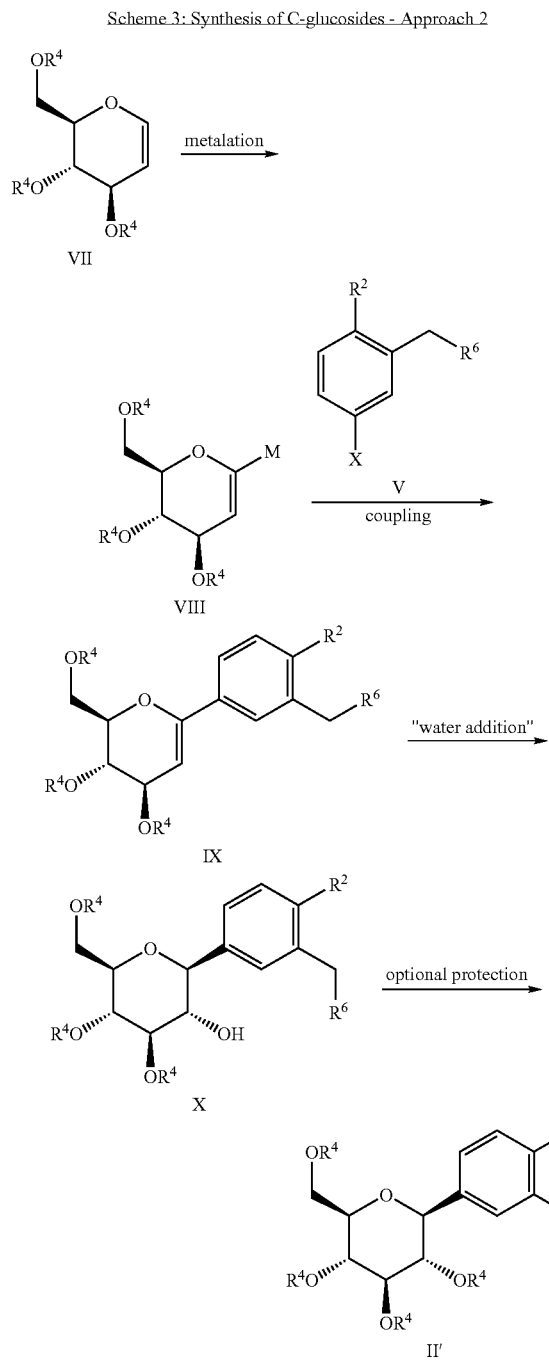

Scheme 3: Synthesis of C-glucosides - Approach 2

Preferred meanings of the group $R^6$ are H, O—$C_{1-6}$-alkyl, O-aryl, para-$R^7$-phenyl and $OR^4$ wherein aryl and $R^4$ are as defined hereinbefore. $R^7$ preferably denotes —C≡C—$R^1$, Cl, —SiAlk$_3$, —CHO, —C≡C—C(OH)Alk$_2$, —C≡C—SiAlk$_3$, —C≡C—SiArAlk$_2$, —C≡C—Si(biphenyl)Alk$_2$ wherein $R^1$, R, Ar, Alk and $R^4$ are as defined hereinbefore. Even more preferably $R^6$ denotes H, O—$C_{1-6}$-alkyl, O-aryl, OH and para-$R^7$-phenyl- wherein aryl is as defined hereinbefore and $R^7$ preferably denotes —C≡C—$R^1$, —CHO, Cl, —SiMe$_3$, —C≡C—C(OH)Alk$_2$, —C≡C—SiAlk$_3$, —C≡C—SiArAlk$_2$ and —C≡C—Si(biphenyl)Alk$_2$ wherein $R^1$, Ar and Alk are as defined hereinbefore. Suitable reaction conditions are known to the one skilled in the art and can be adapted from the literature for example Synlett 2004, pp. 1235-1238; Org. Lett. 2003, 5, pp. 405-2408 and references quoted therein for analogous approaches.

The protected D-glucal VII is metallated to yield the D-glucal derivative VIII wherein M denotes a lithium, magnesium, zinc, indium, boron, tin, silicon or chromium moiety; in particular lithium, magnesium halide, zinc halide, indium halide, boronic acid, boronic acid ester. Metalation of glucal VII at C-1 may be accomplished by deprotonation with a strong base. Strong bases capable of deprotonating the glucal may be lithium bases such as e.g. n-butyl lithium, sec-butyl lithium or tert-butyl lithium. The C-1 lithiated glucal (M=Li) thus obtained may be transmetalated with different electrophilic metal sources delivering the corresponding C-1 metalated glucal derivative. Metal species suitable for the subsequent transformation, coupling with the aglycon moiety, are derived from e.g. lithium, magnesium, zinc, indium, boron, tin, silicon, and chromium. The transmetalation of the glucal compound from lithium to one of the metals mentioned may be conducted with the corresponding e.g. halides such as chloride, bromide and iodide, sulfonates such as e.g. trifluoromethanesulfonate, and alcoxides such as e.g. methoxide, ethoxide, propoxide and isopropoxide of the metal species to be introduced. Depending on the number of vacant sides of the metal transmetalated to the metal may bear more than one glucal residue such as in the corresponding triglucal indium or diglucal zinc. The corresponding monoglucal substituted metal derivatives are employable as well. The metalation of glucal with a strong base, in particular a lithium base, is preferably performed in inert solvents such as e.g. tetrahydrofuran, ether, dioxane, dimethoxyethane, hexane, and toluene. Preferred temperatures are in the range between −80° C. and 50° C. The transmetalation may be conducted in the same solvents depending on the electrophilic metal species in the same temperature range. Among the electrophilic metal species usable in the transmetalation the following are among the most appropriate: trialkylchlorostannane, tetrachlorostannane, trialkylchlorosilane, trialkoxychlorosilyl chloride or bromide, boron trichloride, trialkyl borates, dialkylchloroborane, indium trichloride, zinc chloride, triflate or bromide, magnesium chloride or bromide. This compilation is by no means meant to restrict the employable metal electrophiles to the ones mentioned but is supposed to give an idea of electrophiles that can be used.

The metalated glucal derivative of the formula VIII thus obtained may be coupled with the aglycon V wherein the group X denotes a replaceable group, preferably selected from the group consisting of chlorine, bromine, iodine, sulfonate such as e.g. trifluoromethanesulfonate, tosylate, benezenesulfonate, and mesylate, chlorosulfonate, sulfonic acid or salts thereof, hydroxycarbonyl or salts thereof, nitrile, and diazonium salts. The coupling reactions are preferably carried out in the presence of a transition metal catalyst such as e.g. salts, complexes or elemental modifications of palladium, copper, iron, and nickel. Complexes can be formed in situ or prior to the addition of the transition metal to the reaction mixture. The ligands in the complexes of the transition metal may be e.g. triarylphosphine, aryldialkylphosphine, trialkylphosphine, phosphite, 1,3-disubstituted dihydroimidazolium carbene, 1,3-disubstituted imidazolium carbene, and alkenes. The reaction is preferably carried out in an inert organic solvent or mixtures thereof. Suitable solvents may be e.g. tetrahydrofuran, dioxane, dimethoxyethane, hexane, toluene, benzene, dimethylformamide, dimethylacetamide, N-methylpyrrolidinone, acetone, ethyl acetate, water, methanol, ethanol, propanol, isopropanol, ethylene glycol, polyethylene glycol. The coupling reactions are preferably carried out between −80° C. and 180° C., more preferably at −20° C. to 120° C.

The concluding synthetic step in Scheme 3 is the formal addition of water to the double bond in the glucal moiety of compound IX. This process may be done by e.g. hydroboration that results in the formation of the 2-boron-2-desoxy glucose derivative that can be converted to the corresponding glucose compound by oxidation of the carbon-boron bond. Suitable boranes for the hydroboration are e.g. borane or ether, thioether or amine adducts thereof, alkylboranes or dialkylboranes such as e.g. hexylborane, thexylborane, diethylborane and 9-BBN, pinacolborane, catecholborane, halo or dihaloborane such as e.g. dichloroborane. The hydroboration may be conducted in e.g. tetrahydrofuran, hexane, cyclohexane, ether, toluene, benzene, dichloromethane. A preferred temperature range is between −50° C. and 150° C., preferably between −20° C. and 50° C. The oxidative cleavage of the carbon-boron bond may be performed with an oxidizing reagent such as e.g. hydrogen peroxide, tert-butyl hydrogen peroxide, sodium perborate, and trialkylamine N-oxide. Depending on the oxidizing reagent the reaction is advantageously carried out in the presence of a base such as e.g. sodium hydroxide. The reaction is preferably carried out in an inert organic solvent or mixtures thereof. Preferred solvents are selected from among tetrahydrofuran, water, alcohols, dioxane, dimethoxyethane, cyclohexane, hexane, toluene, dichloromethane and mixtures thereof. A preferred temperature range is between −30 to 150° C., preferably between 0 to 110° C.

An alternative to the hydroboration in order to add water to the double bond of the glucal moiety in IX is the combination of epoxidation or dihydroxylation of the double bond and reduction of the resultant anomeric carbon-oxygen bond. Suitable oxidizing reagents for the epoxidation are e.g. dimethyldioxirane, trifluorodimethyldioxirane, 3-chloroperoxybenzoic acid, hydrogen peroxide and oxygen in the presence of a transition metal catalyst. Another suitable oxidizing agent is peroxomonosulfuric acid, peroxodisulfuric acid and salts thereof, in the presence of at least one ketone, in particular triple salts of the formula 2 $KHSO_5 \times KHSO_4 \times K_2SO_4$ which are commercially available, for example under the brand names OXONE® (trademark E.I. du Pont de Nemours) and CAROAT® (trademark Degussa, Peroxid-Chemie GmbH & Co. KG, Dr. -Gustav-Adolph-Str. 3, D-82049 Pullach, Germany) in combination with a ketone, preferably acetone. Dihydroxylation can be accomplished with e.g. osmium tetroxide and dipotassium osmium tetroxide preferably in the presence of a co-oxidant such as e.g. potassium hexacyano-ferrate, hydrogenperoxide, and N-methylmorpholine N-oxide; hydrolytic opening of the oxirane resulting from the epoxidation gives also access to the dihydroxylation product. The oxidations may be conducted in inert organic solvents or mixtures thereof such as e.g. dichloromethane, tetrahydrofuran, ether, hexane, cyclohexane, dioxane, acetone, ethyl acetate, acetonitrile, water, alcohols and mixtures thereof. A preferred temperature range is between −80° C. and 100° C., preferably between −50° C. and 50° C. Reduction of the anomeric carbon-oxygen bond of the oxirane or dihydroxylation product may be accomplished with reducing agents such as e.g. trialkylsilanes such as e.g. triethylsilane, borohydrides such as e.g. sodium borohydride and aluminum hydrides such as e.g. diisobutylaluminum hydride. Depending on the reducing agent the presence of a Lewis acid such as e.g. boron trifluoride etherate, zinc chlorides, trimethylsilyl chloride or triflate, alkyl-, dialkyl- or aluminum halide, copper triflate, and Brønsted acids such as e.g. hydrochloric acid, acetic acid, alkyl- or arylsulfonic acids, trifluoroacetic acid is necessary or at least advantageous. Dichloromethane, acetonitrile, tetrahydrofuran, ether, hexane are among the preferred solvents. A preferred temperature range is between −80° C. and 120° C. Hydrogen in combination with a transition metal catalyst such as e.g. palladium on carbon, Raney-nickel, and palladium hydroxide may be used as well.

In the above and below described reactions of Scheme 3 the protecting groups $R^4$ are preferably chosen in view of their stability under basic or strongly basic conditions, in particular the groups $R^4$ independently of each other denote $—SiR^aR^b R^c$, wherein two adjacent groups $R^4$ may be linked with each other to form a bridging group $SiR^aR^b$, wherein $R^a$, $R^b$, $R^c$ are defined as hereinbefore, preferably denote isopropyl.

In the product of the formula X the hydroxyl group in 2-position of the pyranose-ring and optionally one or more further hydroxyl groups may be protected to yield a compound of the formula II' wherein $R^4$ is defined as hereinbefore, particularly not being hydrogen. This additional step of protection is preferably performed before further transformation of the compound of the formula X or II' is done, in particular in cases where $R^6$ does not denote

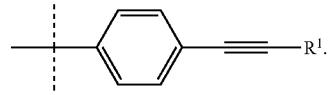

Subsequently the product of the formula X or II' wherein the group $R^6$ denotes a group of the subformula

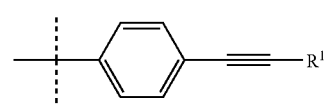

with $R^1$ being defined as hereinbefore, may be transferred into the product of the formula I by cleaving, in particular hydrolysing, the protective groups $R^4$ not being hydrogen, advantageously employing methods as described hereinbefore; in particular as described with respect to Scheme 1.

The reaction scheme 4 depicts the synthesis route according to the 5$^{th}$ aspect of the present invention. A protected D-glucal of the formula VII is epoxidized to yield the corresponding glucaloxide of the formula XI which is coupled with a metallated aglycon of the formula VI to yield the product of the formula X.

Scheme 4: Synthesis of C-glucosides - Approach 3

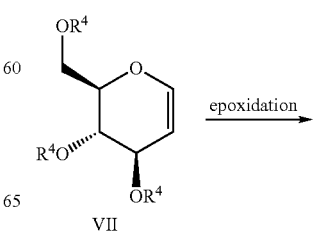

VII

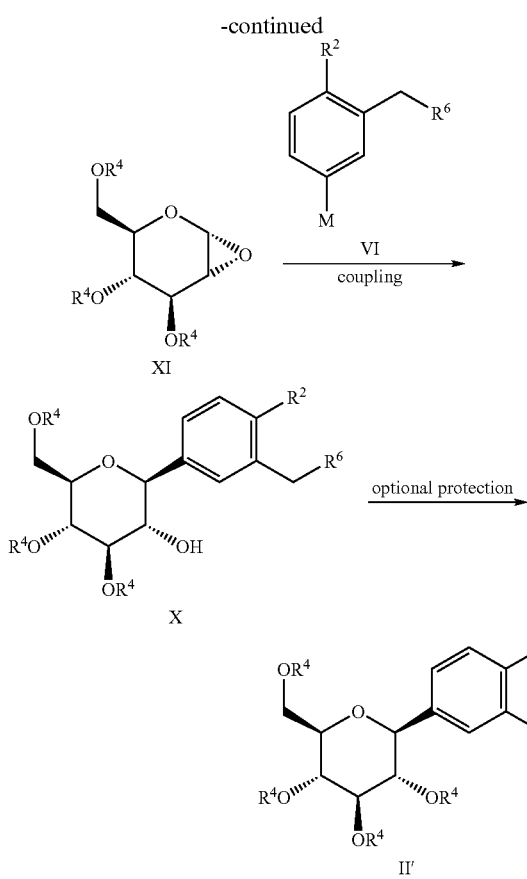

The group $R^6$ preferably denotes H, O—$C_{1-6}$-alkyl, O-aryl, para-$R^7$-phenyl and O$R^4$ wherein aryl and $R^4$ are as defined hereinbefore. $R^7$ preferably denotes —C≡C—$R^1$, Cl, —SiAlk$_3$, —C≡C—SiAlk$_3$, —C≡C—SiArAlk$_2$, —C≡C—Si(biphenyl)Alk$_2$ wherein $R^1$, R, Ar, Alk and $R^4$ are as defined hereinbefore. Even more preferably $R^6$ denotes O—$C_{1-6}$-alkyl, O-aryl and para-$R^7$-phenyl- wherein aryl is as defined hereinbefore and $R^7$ preferably denotes —C≡C—$R^1$, Cl, —SiMe$_3$, —C≡C—SiAlk$_3$, —C≡C—SiArAlk$_2$ and —C≡C—Si(biphenyl)Alk$_2$ wherein $R^1$, Ar and Alk are as defined hereinbefore.

Scheme 4 illustrates an alternative access to C-glucosides starting from the glucal VII. Suitable reaction conditions are known to the one skilled in the art and can be adapted from the literature for example *Synlett* 2003, pp. 870-872; *Tetrahedron* 2002, 58, pp. 1997-2009 and references quoted therein for analogous approaches. Epoxidation with an appropriate oxidizing reagent transforms the glucal VII into the corresponding glucaloxide XI. Suitable reaction conditions for this transformation have already been described for the analogous conversion of glucal IX shown in Scheme 3. Among the oxidizing agents described there dimethyldioxirane and trifluorodimethyldioxirane generated separately or in situ are preferred. Said oxidizing agents may be obtained with e.g. peroxomonosulfuric acid, peroxodisulfuric acid and salts thereof, in the presence of at least one ketone, in particular with triple salts of the formula 2 KHSO$_5$×KHSO$_4$×K$_2$SO$_4$ which are commercially available, for example under the brand names OXONE® (trademark E.I. du Pont de Nemours) and CAROAT® (trademark Degussa, Peroxid-Chemie GmbH & Co. KG, Dr. -Gustav-Adolph-Str. 3, D-82049 Pullach, Germany) in combination with a ketone, preferably acetone or trifluoroacetone. The reaction is preferably carried out at temperatures in the range between −80 and 0° C. in an inert organic solvent or mixtures thereof. Preferred solvents are selected from the group consisting of dioxane, 1,2-dimethoxyethane, toluene, hexane, tetrahydrofuran, diethylether, dichloromethane and mixtures thereof. In the above and below described reactions the protecting groups $R^4$ are preferably independently of each other selected from the group consisting of $C_{1-4}$-alkylcarbonyl, $C_{1-4}$-alkyloxycarbonyl, arylmethyl, $C_{1-6}$-alkoxymethyl, and $R^aR^bR^cSi$—, wherein aryl, $R^a$, $R^b$ and $R^c$ are defined as hereinbefore. If two adjacent groups $R^4$ linked with each other to form a bridging group it preferably consists of Si$R^aR^b$, C=O, C$R^aR^b$ or C$R^a$O$R^b$—C$R^a$O$R^b$, wherein $R^a$, $R^b$ and $R^c$ are defined as hereinbefore.

The ensuing reaction, epoxide opening with a metalated aglycon of the formula VI in which M denotes a lithium, magnesium, zinc, indium, aluminum or boron moiety, affords the desired C-glucoside. For this transformation the preferred meaning of M is lithium, magnesium halide, zinc halide, indium halide, aluminum halide, dialkylaluminum halide, B(OAlk)$_2$ or B(OH)$_2$. The synthesis of the lithium or magnesium derivative of compound VI has been detailed in Scheme 2, whereas the transmetalation of these compounds to one of the alternative metal species may be done in analogy to the transmetalation of the lithiated glucal to the same metal derivatives presented in Scheme 3. The epoxide opening reaction may take place without an adjuvant or in the presence of a transition metal salt or complex such as e.g. copper cyanide or halide or in the presence of a Lewis acid such as e.g. borontrifluoride etherate or trimethylsilyl-chloride or triflate. Suitable inert solvents may be e.g. acetone, ether, tetrahydrofuran, acetonitrile, dichloromethane, toluene, hexane and mixtures thereof. A preferred temperature range is between −80° C. to 60° C.

In the product of the formula X the hydroxyl group in 2-position of the pyranose-ring and optionally one or more further hydroxyl groups may be protected to yield a compound of the formula II' wherein $R^4$ is defined as hereinbefore, particularly not being hydrogen. This additional step of protection is preferably performed before further transformation of the compound of the formula X or II' is done, in particular in cases where $R^6$ does not denote

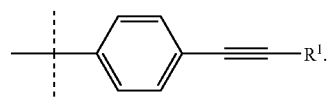

Subsequently the product of the formula X or II' wherein the group $R^6$ denotes a group of the subformula

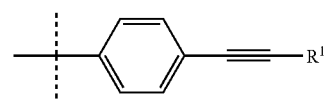

with $R^1$ being defined as hereinbefore, may be transferred into the product of the formula I by cleaving, in particular hydrolysing, the protective groups $R^4$ not being hydrogen, advantageously employing methods as described hereinbefore; in particular as described with respect to Scheme 1.

The reaction scheme 5 depicts the synthesis route according to the 6th aspect of the present invention. A glucose derivative of the formula XII is reacted with a metallated aglycon of the formula VI to yield the product of the formula II'.

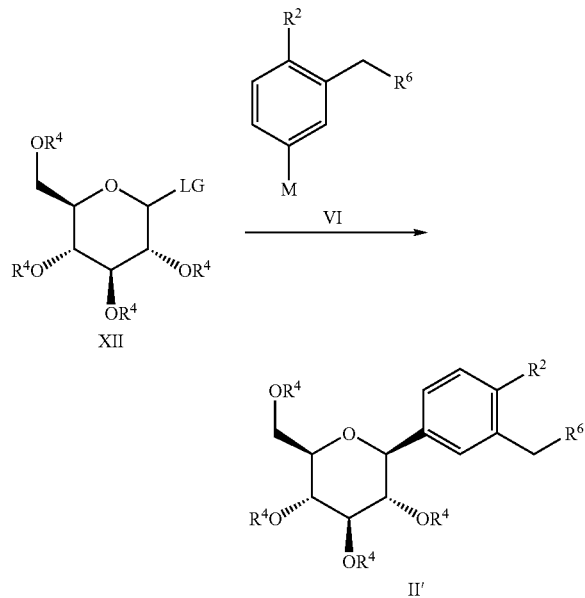

Preferred meanings of the group $R^6$ are H, O—$C_{1-6}$-alkyl, O-aryl, para-$R^7$-phenyl and $OR^4$ wherein aryl and $R^4$ are as defined hereinbefore. $R^7$ preferably denotes —C≡C—$R^1$, Cl, —$OSO_2R$, —$SiAlk_3$, —C≡C—$SiAlk_3$, —C≡C—$SiAr$-$Alk_2$, —C≡C—Si(biphenyl)$Alk_2$ wherein $R^1$, R, Ar, Alk and $R^4$ are as defined hereinbefore. Even more preferably $R^6$ denotes O—$C_{1-6}$-alkyl, O-aryl and para-$R^7$-phenyl- wherein aryl is as defined hereinbefore and $R^7$ preferably denotes —C≡C—$R^1$, —$SiMe_3$, —C≡C—$SiAlk_3$, —C≡C—$SiAr$-$Alk_2$, —C≡C—Si(biphenyl)$Alk_2$ wherein $R^1$, Ar and Alk are as defined hereinbefore.

A glucose derivative XII bearing a potential leaving group (LG) at the anomeric carbon may be utilized as starting material for the coupling with an metalated aryl aglycon as well. Suitable reaction conditions are known to the one skilled in the art and can be adapted from the literature for example *J. Carbohydr. Chem.* 1994, 13, pp. 303-321 and references quoted therein for analogous approaches. Suitable leaving groups LG may be halides, alcoxides, acyl groups such as carboxylates and carbonates; in particular F, Cl, Br, $C_{1-3}$-alkylcarbonyloxy, $C_{1-3}$-alkyloxycarbonyloxy or $C_{1-3}$-alkyloxy, such as e.g. Cl, Br, methoxide, ethoxide, acetate and methylcarbonate or trichloroacetimidate. Suitable metals M attached to the aryl part are e.g. lithium, magnesium as e.g. magnesium halide, zinc as e.g. zinc halide, indium as e.g. indium dihalide, boron as e.g. boronic acid or boronic acid ester. The preparation of these metalated aryl compounds from the corresponding halogenated aromats has been described in Scheme 4. The substitution reactions can be run without or in the presence of an additional Lewis acid such as e.g. boron trifluoride etherate, trimethylsilyl chloride or triflate depending on the metal species and glucosyl donor employed. The reaction is preferably carried out in an inert organic solvents or mixtures thereof. The preferred solvent is preferably chosen in view of the metalated aglycon, glucosyl donor and adjuvants needed; the following solvents may be advantageous: tetrahydrofuran, dioxane, toluene, hexane, ether, N-methylpyrrolidinone, dimethylacetamide, dimethylformamide, acetonitrile, dichloromethane and mixtures thereof. The coupling reaction is usually conducted between −80° C. and 120° C., preferably at −60° C. to 60° C. In the above and below described reactions the protecting groups $R^4$ are preferably independently of each other selected from the group consisting of $C_{1-4}$-alkylcarbonyl, $C_{1-4}$-alkyloxycarbonyl, $C_{1-4}$-alkyloxymethyl, arylmethyl and $R^aR^bR^cSi$, wherein aryl, $R^a$, $R^b$ and $R^c$ are defined as hereinbefore. If two adjacent groups $R^4$ linked with each other to form a bridging group it preferably consists of $SiR^aR^b$, C=O, $CR^aR^b$ or $CR^aOR^b$—$CR^aOR^b$ wherein $R^a$, $R^b$ and $R^c$ are defined as hereinbefore.

Subsequently the product of the formula II' wherein the group $R^6$ denotes a group of the subformula

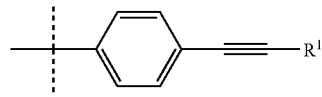

with $R^1$ being defined as hereinbefore, may be transferred into the product of the formula I by cleaving, in particular hydrolysing, the protective groups $R^4$ not being hydrogen, advantageously employing methods as described hereinbefore; in particular as described with respect to Scheme 1.

According to the 7th aspect of the present invention a compound of the formula II', wherein $R^6$ does not denote a group of the subformula

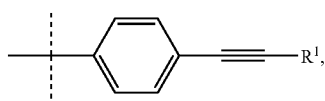

is transferred into a compound of the formula XXVI' (Scheme 6). Optionally the compound of the formula XXVI' is transferred into the compound of the formula II which may be converted to the product of the formula I.

Scheme 6:

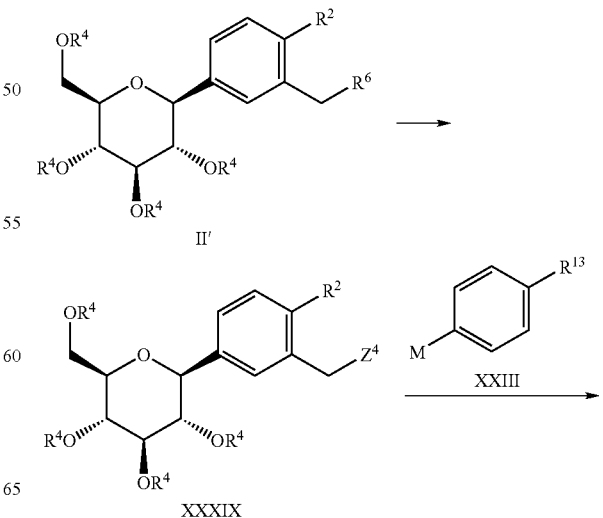

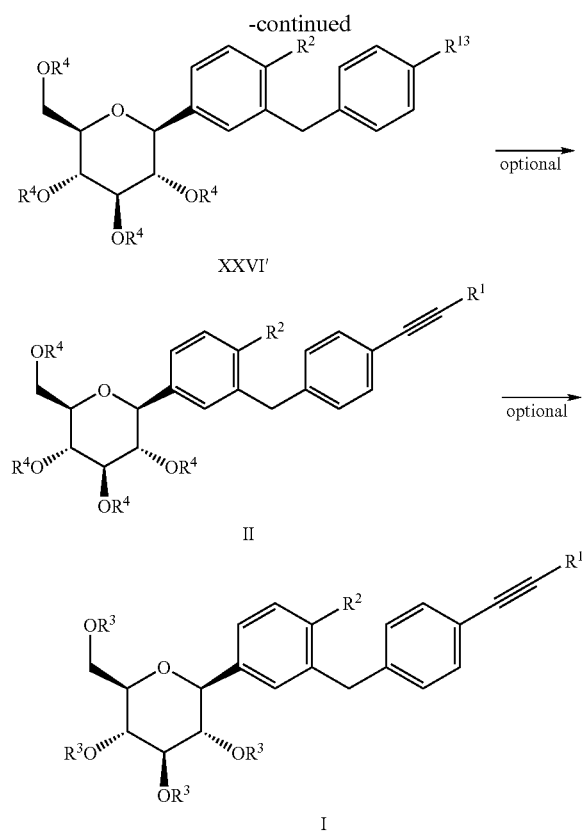

In the synthesis according to Scheme 6 the groups $R^4$ independently of each other preferably denote hydrogen, ($C_{1-8}$-alkyl)carbonyl which may be substituted with $C_{1-4}$-alkoxy, ($C_{1-8}$-alkyl)oxycarbonyl, ($C_{3-8}$-alkenyl)carbonyl, ($C_{3-8}$-alkenyl)oxycarbonyl, arylcarbonyl, arylmethyl, $C_{1-6}$-alkoxymethyl, $R^aR^bR^cSi$, $CR^aR^bOR^c$. If two adjacent groups $R^4$ are linked with each other to form a bridging group it consists of $SiR^aR^b$, C=O, $CR^aR^b$ or $CR^aOR^b$—$CR^aOR^b$, wherein $R^aR^bR^c$ are defined as hereinbefore and each alkyl group may be substituted with up to three substituents selected from fluorine, chlorine, $C_{1-3}$-alkyl, $R^aR^bR^cSi$ and $C_{1-4}$-alkoxy. The group $R^6$ preferably denotes hydrogen, $OR^4$ $C_{1-6}$-alkyloxy or aryloxy, more preferably $C_{1-6}$-alkyloxy or aryloxy.

According to the first reaction step the group $R^6$ of the compound II' is optionally transformed into a group $Z^4$ to yield a compound of the formula XXXIX. The group $Z^4$ denotes chlorine, bromine, iodine, $C_{1-6}$-alkylcarbonyloxy, $C_{1-6}$-alkyloxycarbonyloxy, $C_{1-6}$-alkylsulfonyloxy or —OPO(O—$C_{1-6}$-alkyl)$_2$. Preferred meanings of the group $Z^4$ are chlorine, bromine and iodine, particularly bromine. The compound of the formula II' can be obtained by methods as described with respect to the reaction schemes 2a, 3, 4 and 5. Alternatively a compound of the formula X can be employed as starting material as well. Compounds of the formula X can be obtained by methods as described with respect to the reaction Schemes 3 and 4. In case the group $R^6$ denotes $OR^4$ such a transformation may be not necessary if $R^4$ stands for ($C_{1-18}$-alkyl)carbonyl, ($C_{1-18}$-alkyl)oxycarbonyl, ($C_{3-18}$-alkenyl)oxycarbonyl, arylcarbonyl, aryl-($C_{1-3}$-alkyl)-carbonyl. In this case the second reaction step yielding compound of the formula XXVI' according to Scheme 6 may principally also be performed with a compound of the formula II'.

The first reaction step transforms the group $R^6$ into a group $Z^4$ preferably being a chlorine, bromine or iodine atom; even more preferably a bromine atom. Starting from $R^6$ equals H, only applicable to the compounds bearing chlorine (as substituent $R^2$) on the phenyl ring, the bromine atom may be introduced via a radical substitution reaction. N-bromosuccinimide or bromine in combination with a radical starter such as e.g. azobisisobutyronitrile or dibenzoylperoxide in a halogenated hydrocarbon such as e.g. tetrachloromethane, chloroform, dichloromethane or 1,2-dichloroethane at 0° C. to 120° C. may be suitable reaction conditions for this transformation. More preferably the replacement of an alkoxy or aryloxy group $R^6$ at the benzylic positon by chloride, bromide or iodide is employed. In this case $R^6$ denotes a leaving group that may be replaced under the action of e.g. boron trichloride, tin tetrachloride, aluminum chloride, zinc chloride, phosphorous pentachloride, iodine monochloride, hydrochloric acid, boron tribromide, trimethylsilyl bromide, hydrobromic acid, sodium iodide in conjunction with borontrifluoride etherate or aluminum chloride or trifluoromethanesulfonic acid or trichloromethylsilane or boron tribromide, trimethylsilyl iodide, or hydriodic acid with the corresponding halide. Suitable solvents are for example dichloromethane, toluene, hexane, cyclohexane, dioxane, ether, acetonitrile, water, alcohol, dimethylsulfoxide, dimethylformamide or acetic acid. The preferred product XXXIX is the corresponding bromide ($Z^4$=Br) that is preferably prepared from the corresponding benzyl aryl or alkyl ether II' ($R^6$ denotes alkyloxy or aryloxy) under the action of hydrobromic acid in acetic acid at 0° C. to 100° C.

In the second synthesis step the compound of the formula XXXIX (or alternatively of the formula II' or X) is reacted with a metalated benzene of the formula XXIII wherein $R^{13}$ denotes —CHO, —C≡C—$R^1$, —C≡C—C(OH)Alk$_2$, —C≡C—SiAlk$_3$, —C≡C—SiArAlk$_2$, —C≡C—Si(biphenyl)Alk$_2$, —Si($C_{1-6}$-alkyl)$_3$, iodine, bromine, chlorine, trifluoromethylsulfonyloxy or arylsulfonyloxy; and $M^3$ denotes a lithium-, boron-, magnesium-, silicon-, tin-, cerium-, indium-, zinc-, or chromium-moiety. Preferred meanings of $R^{13}$ are —CHO, —C≡C—$R^1$, —C≡C—C(OH)Me$_2$, —C≡C—SiMe$_3$, —C≡C—Si/Pr$_3$, —C≡C—SiArMe$_2$, —C≡C—Si(biphenyl)Me$_2$, —SiMe$_3$, bromine, chlorine and trifluoromethylsulfonyloxy. Preferred meanings of $M^3$ are boronic acid, boronic acid ester, magnesium halide, zinc halide and indium halide. The synthesis of metalated benzenes of the formula XIII are known to the one skilled in the art; advantageous methods of synthesis are described with respect to the reaction scheme 10. The coupling reaction between the pyranoside XXXIX and the nucleophile XXIII and preferred reaction conditions are described with respect to the Scheme 11. The resulting product of the formula XXVI' corresponds to the compound of the formula II in case $R^{13}$ denotes $R^1$—C≡C—. In cases where $R^{13}$ has different meanings the compound of the formula XXVI' is preferably transformed into a compound of the formula II. Such transformations are known to the one skilled in the art and are for example described with respect to Scheme 13. The protected compound of the formula II may be deprotected to yield the product of the formula I by methods well-known to the one skilled in the art; protective groups $R^4$ not being hydrogen are cleaved, particularly by methods as described with respect to Scheme 1.

The synthesis of aglycon moieties, in particular of the aglycons of the formulae V and VI, or the functionalizations after the attachment of the sugar moiety to the aglycon may be carried out using standard transformations in organic chemistry or at least methods known from the specialist literature in organic synthesis (see inter alia J. March, Advanced Organic Reactions, Reactions, Mechanisms, and Structure, 4th Edition, John Wiley & Sons, Chichester/New York/Brisbane/Toronto/Singapore, 1992 and literature cited therein). The synthesis strategies described in the following provide a demonstration of this, by way of example.

Scheme 7 displays the synthesis of aglycon part XVI starting from benzophenone derivative XIII that can be prepared from a benzoic acid derivative and a phenylalkylether or a metalated phenylalkylether (see Schemes 8 and 11).

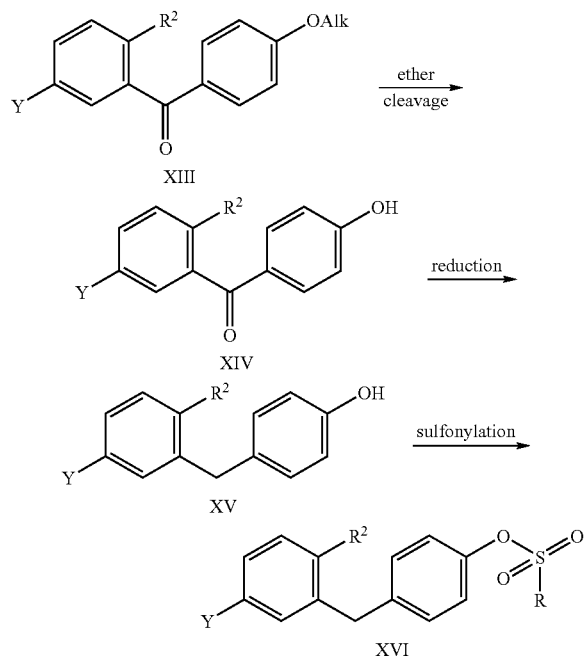

The first step comprises the cleavage of the ether moiety in compound XIII that can be accomplished under neutral, acidic and basic conditions. Suitable acidic reagents for this transformation are e.g. boron trichloride or tribromide or triiodide, trimethylsilyl iodide, aluminum chloride or bromide, hydrobromic acid, hydrochloric acid, cerium chloride, trifluoroacetic acid, and trifluoromethylsulfonic acid that may be used in concert with a nucleophile such as e.g. metal halides such as e.g. sodium iodide, water, alkylthiols, thioanisole, and dialkylsulfides, that may scavenge the departing alkyl group. Depending on the acid used solvents selected from the group consisting of halogenated hydrocarbons, such as e.g. dichloromethane, chloroform or 1,2-dichloroethane, acetonitrile, toluene, hexane, acetic acid and combinations thereof are preferred. Reactions without additional solvent are also feasible. The reactions are generally carried out at −90 to 150° C., preferably at −50 to 50° C. Cleavage under neutral or basic conditions can be done e.g. with metal thiolates such as e.g. sodium sulfide, sodium ethanethiolate, sodium trimethylsilylthiolate, potassium thiophenolate, sodium cyanide, and lithium iodide in solvents such as e.g. dimethylformamide, dimethylacetamide, 1,3-dimethyl-2-oxohexahydropyrimidine, N-methylpyrrolidone, tetrahydrofuran, collidine, and quinoline at temperatures between 0 and 250° C., preferably at 50 to 180° C. The second synthetic step in Scheme 7 reduces benzophenone XIV to furnish phenol XV. Advantageous reducing agents for this conversion are e.g. silane such as e.g. $Et_3SiH$ and triisopropylsilane, borohydride such as e.g. $NaBH_4$, and aluminum hydride such as e.g. $LiAlH_4$ in the presence of a Lewis acid such as for example $BF_3*OEt_2$, tris(pentafluorophenyl)borane, trifluoroacetic acid, hydrochloric acid, aluminum chloride, or $InCl_3$. The reactions are preferably carried out in inert organic solvents such as e.g. halogenated hydrocarbons such as dichloromethane and 1,2-dichloroethane, toluene, benzene, hexane, acetonitrile and mixtures thereof at temperatures of −30 to 150° C., preferably at 20 to 100° C. Reductions with hydrogen in the presence of a transition metal catalyst such as e.g. Pd on charcoal are another possible method of synthesis but might be less suited if $R^2$ denotes Cl due to the vulnerability of this residue under hydrogenolytic conditions. Reductions according to Wolff-Kishner or variants thereof are also conceivable. Hence, the ketone XIV is converted with hydrazine or a derivative thereof such as e.g. 1,2-bis(tert-butyldimethylsilyl)hydrazine into the hydrazone which breaks down under strongly basic reaction conditions and heating to liberate the diphenylmethane XV and nitrogen. The reaction may be carried out in one pot or after isolation of the hydrazone or a derivative thereof in two separate reaction steps. Suitable bases include e.g. KOH, NaOH or KOtBu in solvents such as e.g. ethyleneglycol, toluene, DMSO, 2-(2-butoxyethoxy)ethanol or tert-butanol; solvent-free reactions are also possible. The reactions may be performed at temperatures between 20 and 250° C., preferably between 80 and 200° C. An alternative to the basic conditions of the Wolff-Kishner reduction is the Clemmensen reduction which takes place under acidic conditions, which may also be used here. Scheme 7 concludes with sulfonylation of the phenolic oxygen of compound XV. This transformation is preferably carried out under basic conditions. Suitable bases to generate the phenolate are e.g. group I or II metal salts, in particular carbonates, hydroxides, alkoholates such as e.g. methoxide, ethoxide or tertbutoxide, and metal hydrides such as e.g. sodium hydride. Organic bases such as e.g. trialkylamines or pyridines are among the preferred bases as well. The reaction is preferentially conducted in solvents such as e.g. tetrahydrofuran, ether, hexane, ethyl acetate, acetonitrile, dichloromethane, dichloroethane, toluene, acetone, dimethylformamide, dimethylacetamide, N-methylpyrollidone and mixtures thereof. Suitable sulfonyl electrophiles are derived from e.g. halides such as chlorides and bromides and anhydrides. The reactions are usually performed at −60 to 100° C., preferably at −30 to 50° C. The order of reaction steps is not restricted to as outlined in Scheme 7 but may be rearranged as well.

Scheme 8 describes the assembly of the aglycon part XX starting from the known benzoyl chloride XVII and benzene derivative XVIII.

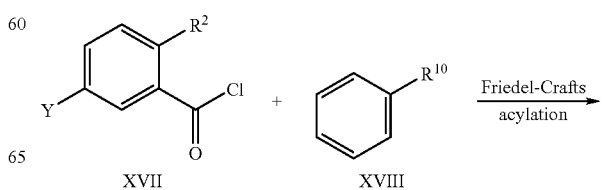

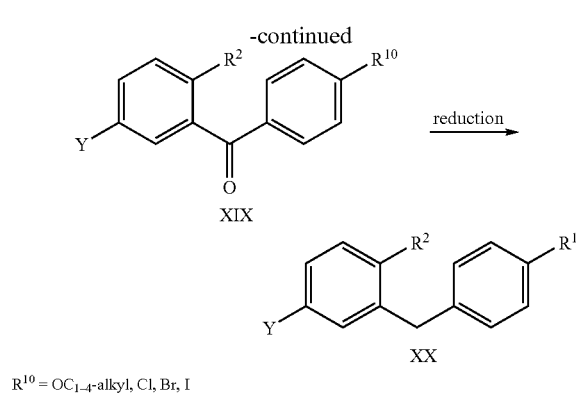

R[10] = OC[1-4]-alkyl, Cl, Br, I

The first step, the preparation of benzophenone XIX, can be characterized as Friedel-Crafts or Friedel-Crafts-type acylation, a well-known and widely used method in organic synthesis. In principal, the benzoyl chloride XVII may be replaced by other benzoic acid derivatives such as e.g. benzoic acids, benzoyl anhydrides, esters, or benzonitriles. This classic reaction has a wide substrate scope and is commonly carried out in the presence of a catalyst such as e.g. AlCl$_3$, FeCl$_3$, iodine, iron, ZnCl$_2$, sulfuric acid, or trifluoromethanesulfonic acid which is used in catalytic or stoichiometric amounts. The reactions are preferentially performed in chlorinated hydrocarbons such as e.g. dichloromethane or 1,2-dichloroethane, in hydrocarbons such as e.g. hexane at temperatures ranging from –30 to 140° C., preferably at 30 to 100° C. However, other solvents and solvent mixtures and also solvent-free reactions or reactions in a microwave oven are also possible. The second reaction step in Scheme 8 is analogous to the final reaction in Scheme 9 described hereinbefore.

Scheme 9 illustrates an alternative synthesis of the aglycon part via a Friedel-Crafts-type alkylation of benzene derivative XVIII with benzyl electrophile XXI.

Scheme 8: Synthesis of Aglycon Part-Approach 2

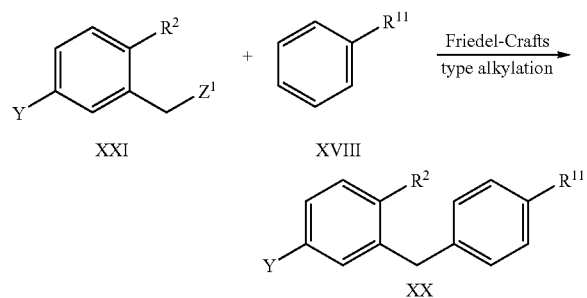

Z$^1$ = OH, OR, OCOR, Cl, Br, I, OCOOR, OSO$_2$R, OPO(OR)$_2$
R$^{11}$ = OH, OC$_{1-4}$-alkyl, Cl, Br, I Suitable reaction conditions are known to the one skilled in the art and can be adapted from the literature for example see *Angew. Chem.* 2005, 117, pp. 242-246 and *Syn. Commun.* 2004, 34, pp. 3161-3165 and references quoted therein. The reaction is commonly conducted in the presence of a catalyst, in particular of a Lewis acid such as e.g. scandium chloride, zinc chloride, iron chloride, aluminum chloride or boron trifluoride, a Brønsted acid such as e.g. sulfuric acid, hydrochloric acid or hydrogenfluoride, a lanthanide salt such as e.g. cerium sulfate or ytterbium chloride, of an actinide salt, a transition metal salt or a complex such as e.g. IrCl$_3$*nH$_2$O, RhCl$_3$*nH$_2$O, H$_2$[PtCl$_6$]*6H$_2$O or H$_2$[PdCl$_6$]*6H$_2$O. The catalysts can be applied in stoichiometric or excess quantities though in many cases 10 substoichiometric or even catalytic amounts are sufficient. The reactions are usually carried out with an excess of aromatic compound XVIII relating to the benzyl electrophile without solvent; though inert solvents such as e.g. halogenated hydrocarbons or hydrocarbons can be employed as well. The reaction is generally conducted at temperatures between 0 and 200° C., preferably at 20 to 140° C.

The approach presented in Scheme 10 starts with the metalation of compound XXII. Lithium or magnesium substituted aromatic compounds XXIII may be prepared from chlorinated, brominated, or iodinated aromatic compounds XXII in the same manner as used for the metalated aglycon VI described in Scheme 2.

Scheme 10: Synthesis oc Aglycon Part-Approach 4

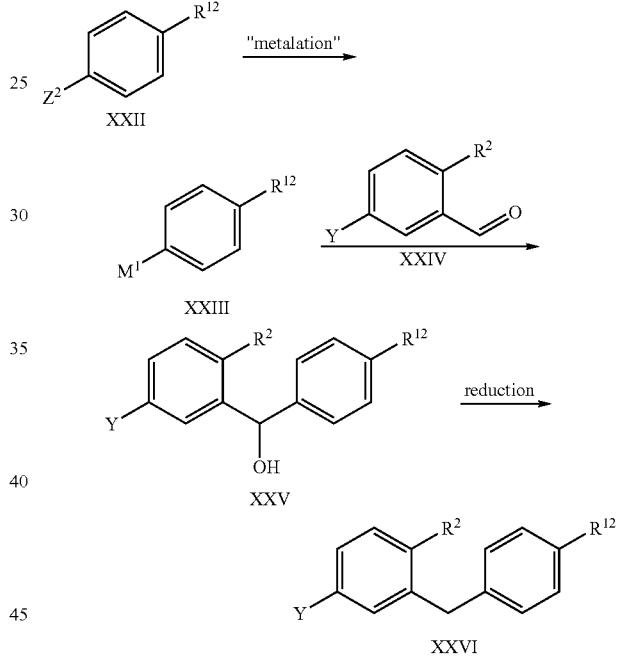

M$^1$ = e.g. Li, MgHal, ZnHal, InHal$_2$, CrHal$_2$, B(OH)$_2$, BR$_2$, CeHal$_2$
Z$^2$ = Hal, OSO$_2$R, OSO$_2$CF$_3$
Hal = Cl, Br, I
R$^{12}$ = OH, OAlk, SiAlk$_3$, I, Br, Cl, OSO$_2$R, C≡C—R$^1$

The corresponding boron substituted compound such as e.g. boronic acid, boronic acid ester, or dialkylarylborane is accessible from these metalated phenyl groups XXIII by the reaction with an appropriate boron electrophile such as e.g. boronic acid ester, haloboronic acid ester, alkylboronic acid ester, dialkylboronic acid ester, trihaloborane, and derivatives thereof. In addition, the boronylated aromatic compound XXIII may also be prepared from the corresponding chlorinated, brominated, iodinated, or pseudohalogenated such as e.g. trifluoromethane-sulfonated and tosylated precursor and a diboron compound such e.g. bis(pinacolato)diboron and bis(neopentyl-glycolato)diboron, or a borane such as e.g. pinacolborane through a transition metal catalyzed reaction (see e.g. *Tetrahedron Lett.* 2003, p. 4895-4898 and references quoted therein). The transition metal, e.g. palladium, is employed as element, salt, or complex; common Pd sources are e.g. palladium on charcoal, palladium acetate, palladium chloride, palladium bromide, palladium dibenzylideneacetone that are used as such or in combination with a ligand such as e.g. phosphines such as e.g. tricyclohexylphosphine, triphenylphosphine, 1,1'-bis(diphenylphosphino)ferrocene, and tritolylphosphine, or phosphites or imidazolium salts such as 1,3-diaryl or dialkyl imidazolium halides or pseudohalides or dihydroimidazolium salts. The resulting complex of the transition metal and the ligand may be prepared in situ or in a separate step. The reactions are preferably conducted in the presence of a base such as e.g. triethylamine, potassium acetate, potassium carbonate, potassium phosphate, sodium hydroxide, triethylamine or ethyldiisopropylamine, in solvents such as e.g. acetonitrile, tetrahydrofuran, dimethylsulfoxide, dimethylformamide, dimethylacetamide, N-methylpyrrolidone, dioxane, toluene and mixtures thereof at 0 to 180° C., preferably at 60 to 140° C. The lithium or magnesium substituted phenyl compounds XXIII add spontaneously to benzaldehyde XXIV furnishing diarylmethanol XXV. This reaction can be performed in solvents such as diethylether, tetrahydrofuran, toluene, dichloromethane, dioxane, hydrocarbons such as e.g. hexane and mixtures thereof at temperatures ranging from −100 to 20° C., preferably at −80 at 0° C. Aryl boronic acids XXIII can be added to the benzaldehyde derivative XXIV by means of a rhodium catalyzed reaction furnishing the respective diarylmethanol XXV (see e.g. *Adv. Synth. Catal.* 2001, p. 343-350 and references quoted therein). The concluding step in Scheme 10 is the reduction of the diarylmethanol XXV to the diarylmethane XXVI. Suitable reducing agents for this transformation are e.g. $NaBH_4$, $LiAlH_4$, $iBu_2AlH$, $Et_3SiH$, $iPr_3SiH$ or $Ph_2SiClH$. The reaction is usually carried out in the presence of a Lewis acid such as for example $BF_3*OEt_2$, trifluoroacetic acid, hydrochloric acid, $InCl_3$, or $AlCl_3$ in a solvent such as halogenated hydrocarbons such as e.g. dichloromethane or 1,2-dichloroethane, toluene, hydrocarbons such as e.g. hexane, acetonitrile or mixtures thereof at temperatures of −80 to 150° C., preferably at −20 to 100° C. Reductions with hydrogen in the presence of a transition metal catalyst such as e.g. Pd on charcoal are also possible.

The synthesis sketched in Scheme 11 begins with the addition of the metalated benzene derivative XXIII to benzoic acid or a derivative thereof (XXVII) such as benzoic acid esters, benzoic acid anhydrides, benzamides such as e.g. of the Weinreb type, benzonitriles, or benzoyl chlorides to deliver the benzophenone XXVIII.

Scheme 11: Synthesis of Aglycon Part-Approach 5

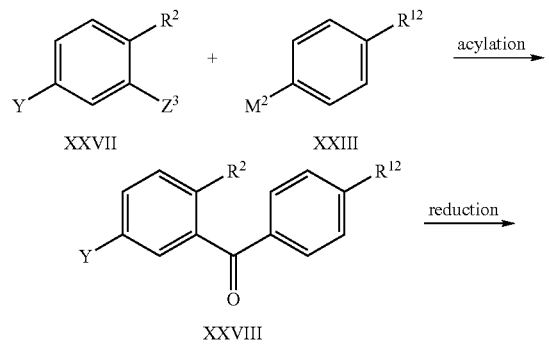

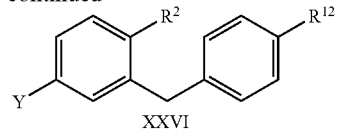

$Z^3$ = e.g. COOH, COOR, $CONR_2$, CONROR, CN, COCl
$M^2$ = e.g. Li, MgHal, $B(OH)_2$, $BR_2$, $SiR_3$, $SnR_3$, $CeHal_2$, $InHal_2$, ZnHal
Hal = I, Br, Cl
$R^{12}$ see Scheme 10

Lithium or magnesium derivatized benzenes XXIII can principally be added to benzamides, benzoic acid esters, benzoyl chlorides, benzoic acid anhydrides, and benzonitriles to give the desired benzophenone XXVIII while usually only lithiated benzenes react with benzoic acids to produce the same compound. The latter reaction can be carried out in e.g. tetrahydrofuran, dioxane, diethylether, benzene, toluene, hexane and mixtures thereof at −80 to 100° C., preferably at −30 to 40° C. Benzonitriles and benzamides such as e.g. the corresponding Weinreb-type amide or a close derivative thereof are preferentially reacted in tetrahydrofuran, dioxane, toluene, hexane, ether and mixtures thereof at temperatures ranging from −90 to 50° C., preferably at −80 to 20° C. Benzoyl chlorides or anhydrides and benzoic acid esters are commonly employed in inert solvents such as tetrahydrofuran, diethylether, toluene, dichloromethane, dioxane, hydrocarbons such as e.g. hexane or mixtures of them at low temperatures, preferably at −80 to 0° C. To prevent double addition of the organometal compound to benzoyl chlorides, benzoyl anhydrides or benzoic acid esters to produce the corresponding alcohol the addition may superiorly carried out in the presence of a trapping reagent such as e.g. trimethylsilyl chloride. An alternative choice to prevent double addition in the cases mentioned may be transmetalation to a less reactive nucleophile XXIII. Suitable metals are e.g. zinc, cerium, chromium, or indium that are introduced as e.g. chloride, bromide, iodide or pseudo halide salt such as e.g. trifluoromethanesulfonate to transmetalate the lithium or magnesium compound to give the corresponding less reactive, more selective metal compound XXIII. The transmetalation is preferentially conducted in the solvent wherein the initial organometal compound is generated (see above) at temperatures of −90 to 0° C. Transmetalation is not restricted to the metals mentioned and the boron derivatized compounds already described in Scheme 10 but can also furnish e.g. stannanes and silanes. Some of the transmetalated compounds react spontaneously with the corresponding benzoyl electrophile, particularly benzoyl chloride and anhydride, but the addition of a transition metal catalyst may be advantageous. In particular arylboronic acids, esters thereof, dialkylarylboranes, aryltrifluoroborates, stannanes, silanes, indium, chromium, and zinc derivatized compounds XXIII couple with benzoyl chloride derivatives XXVII mediated by a transition metal such as e.g. palladium, copper, iron, nickel, that may be used as element or salt such as e.g. acetate, chloride, bromide, iodides, acetylacetonate, trifluoromethanesulfonate, and cyanide in combination with ligands such as e.g. phosphites, phosphines such as e.g. triphenylphosphine, tricyclohexylphoshine, tritolylphosphine, 1,3-substituted imidazolium or dihydroimidazolium compounds delivering diarylketones XXVIII. The active transition metal species can be prepared prior to the addition of the coupling partners but also in the presence of the reaction partners in situ. Suitable solvents are e.g. dimethylformamide, dimethylacetamide, N-methylpyrrolidone, dimethylsulfoxide, dioxane, ether, hexane, toluene, tetrahydrofuran, dichloromethane or mixtures thereof that are preferably used at −50 to 150° C., particularly preferably at 0 to 120° C. The subsequent conversion, reduction of the ketone to the diarylmethane has already been detailed above and can be applied analogously here.

According to the Scheme 12 the metalated aryl groups XXIII that can be synthesized as described above can also be reacted with benzyl electrophiles XXIX such as e.g. benzyl chlorides, bromides, iodides, sulfonates, phosphonates, carbonates, or carboxylates affording diarylmethanes XXVI.

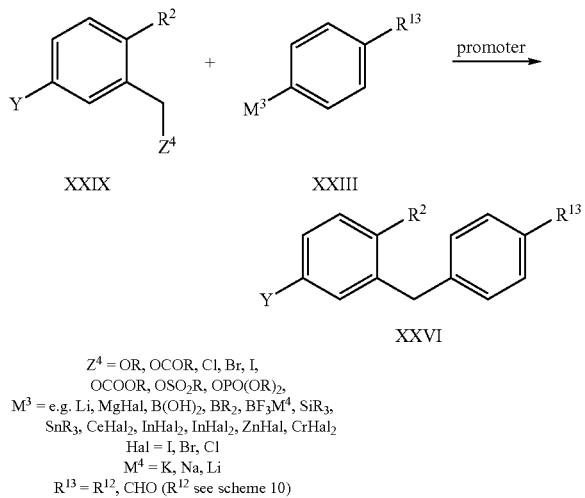

Scheme 12: Synthesis of Aglycon Part - Approach 6

$Z^4$ = OR, OCOR, Cl, Br, I,
OCOOR, OSO$_2$R, OPO(OR)$_2$,
$M^3$ = e.g. Li, MgHal, B(OH)$_2$, BR$_2$, BF$_3$M$^4$, SiR$_3$,
SnR$_3$, CeHal$_2$, InHal$_2$, InHal$_2$, ZnHal, CrHal$_2$
Hal = I, Br, Cl
$M^4$ = K, Na, Li
$R^{13}$ = $R^{12}$, CHO ($R^{12}$ see scheme 10)

Lithium or magnesium derivatized phenyl compounds XXIII are reacted favorably (but not always necessarily) in the presence of a transition metal such as e.g. copper, iron, nickel, or palladium (see e.g. *Org. Lett.* 2001, 3, 2871-2874 and *Tetrahedron Lett.* 2004, p. 8225-8228 and references cited therein). Usable solvents are e.g. tetrahydrofuran, dioxane, toluene, dichloromethane, hexane, ether or mixtures thereof. The range of reaction temperature is from −90 to 20° C., preferably from −80 to −20° C. The transition metal can be employed as element such as e.g. on charcoal, as salt such as e.g. acetate, acetylacetonate, cyanide, chloride, bromide, iodide, trifluoromethanesulfonate, or as complex such as e.g. with dibenzylideneacetones, phosphites, phosphines such as e.g. triphenylphosphine, tricyclohexylphoshine, and tritolylphosphine, or with carbenes derived from e.g. 1,3-disubstituted imidazolium or dihydroimidazolium compounds. The active transition metal species can be prepared in situ in the presence of the reaction partners or prior to the addition of the coupling partners. Arylmetal compounds XXIII bearing a e.g. boron, tin, silicon, zinc, indium or chromium residue are preferably used in combination with a transition metal catalyst. Suitable metal compounds of these types are e.g. boronic acids, boronic acid esters, dialkylboranes, trifluoroborates, trialkylstannanes, trichlorostannanes, trialkoxysilanes, dihaloindium substituted or halozinc substituted compounds. The metal substituted compounds XXIII may be synthesized as described before by transmetalation from the corresponding lithium or magnesium derivatized compounds or as in the case of zinc, chromium and indium also directly from the corresponding arylchloride, bromide or iodide by insertion of the elemental metal. The coupling reaction with the benzyl electrophile may be conducted in tetrahydrofuran, dimethylformamid, dimethylacetamid, N-methylpyrrolidone, dimethylsulfoxide, toluene, ether, dioxane, dichloromethane, acetonitrile, hexane, water, alcohols such as e.g. ethanol, isopropanol, or mixtures thereof at reaction temperatures of −30 to 180° C., preferably at 0° C. to 150° C. Depending on the metal an additional base such as e.g. triethylamine, ethyldiisopropylamine, cesium or potassium or sodium or lithium carbonate, potassium or sodium or lithium tert-butoxide, potassium phosphate, potassium or cesium or tetrabutylammonium fluoride, sodium hydroxide, thallium hydroxide, sodium methoxide and/or other additives such as e.g. lithium chloride, silver salts such as e.g. carbonate or oxide, tetrabutylammonium bromide, and sodium bromide may be advantageous or even essential (see e.g. M. Schlosser, Organometallics in Synthesis, John Wiley & Sons, Chichester/New York/Brisbane/Toronto/Singapore, 1994 and references cited therein). A particularly suitable combination constitute a benzyl bromide or iodide XXIX, a boronic acid XXIII and palladium chloride as catalyst in a water/acetone mixture at 0 to 80° C.

The following schemes outline preferred approaches to the attachment of the alkyne residue to the aglycon part.

Scheme 13 illustrates the attachment of the alkyne residue to the distal phenyl group via a transition metal catalyzed coupling of a terminal alkyne with an appropriately activated phenyl group.

Scheme 13: Attachment of Alkyne Residue - Approach 1

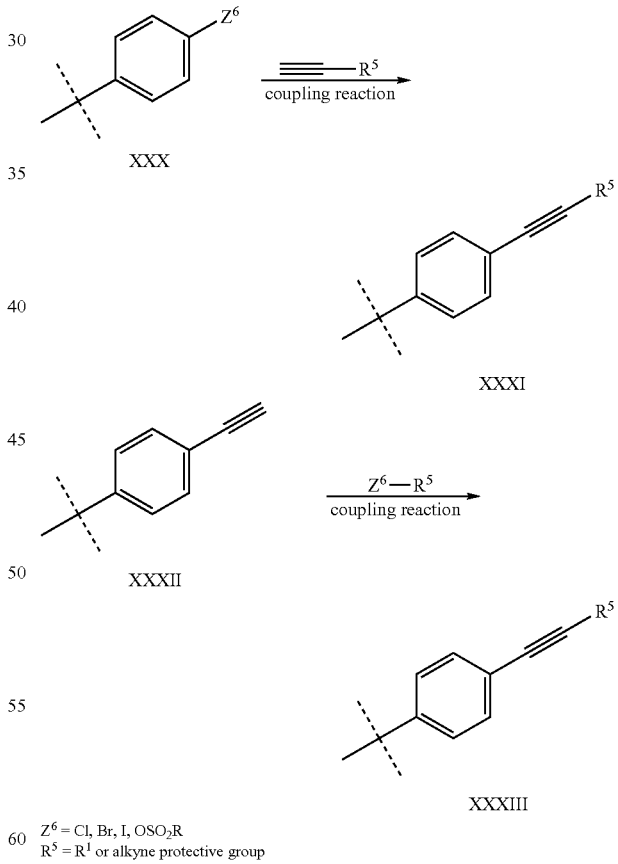

$Z^6$ = Cl, Br, I, OSO$_2$R
$R^5$ = $R^1$ or alkyne protective group

Suitable reaction conditions are known to the one skilled in the art and can be adapted from the literature for example see e.g. *Chem. Rev.* 2003, 103, pp. 1979-2017 and references quoted therein. Preferred leaving groups $Z^6$ on the phenyl group may be e.g. chloride, bromide, iodide, sulfonates such as trifluoromethanesulfonate, mesylate, tosylate and benzenesulfonate. In addition to the terminal alkyne metal acetylides derived from magnesium, zinc, copper, boron, aluminum, silicon, indium and tin may be used as well. Free sides on the metal left after the addition of one acetylene may be occupied with e.g. halide, sulfonate such as trifluormethansulfonate, alkyl, hydroxyl, alcoxy, or another acetylene molecule. Depending on the metal the acetylide may be generated in the presence of the coupling partner or has to be formed prior to the submission to the coupling conditions. The preferred transition metal to execute the coupling is palladium that may be employed as element such as e.g. palladium on carbon or finely dispersed palladium, salt such as e.g. halide, sulfonate such as e.g. trifluoromethanesulfonate, and acylates such as e.g. acetate, or complex with phosphines, phosphites, alkenes, dibenzylideneacetone, aryl or alkylnitriles, 1,3-dialkyl or diaryl imidiazoliumcarbenes, 1,3-dialkyl or diaryl dihydroimidazoliumcarbenes, or palladium combined with ligands of the two latter classes. Depending on the acetylide used additives such as e.g. bases such as e.g. triethylamin, ethyldiisopropylamine, diethylamine, butylamine, pyrrolidine, piperidine, potassium or cesium or silver carbonate, potassium or sodium acetate, alcoxides such as e.g. sodium methoxide, thallium hydroxide, silver oxide, fluoride sources such as e.g. potassium or cesium or tetrabutylammonium fluoride, salt additives such as e.g. tetraethylammonium chloride, lithium bromide or chloride, may be advantageous. As co-catalysts copper salts such as e.g. copper chloride, bromide or iodide or silver salts may be employed. Suitable solvents are dimethylformamide, dimethylacetamide, N-methylpyrrolidinone, dimethylsulfoxide, acetonitrile, tetrahydrofuran, dioxane, benzene, toluene, water, methanol, ethanol, propanol, isopropanol, 1,2-dichloroethane, chloroform, hexane or mixtures thereof. Reactions without additional solvents are also possible. The reactions are preferably carried out at −30° C. to 180° C., more preferably at 0° C. to 130° C. The coupling reaction with a terminal alkyne can also be used to attach an alkyne unit with a protective group on the opposite end of the triple bond. After removal of the protective group another aryl group may be linked to the opposite end under analogous reaction conditions. In cases in which the alkyne bears another functional group that can be employed for the coupling reaction such as e.g. trimethylsilyl both coupling reactions can be run in the same reaction pot in succession by varying the reaction conditions.

A terminal alkyne can also be formed on the distal phenyl group by one carbon elongation starting from the corresponding aldehyde XXXIV (Scheme 14).

Scheme 14: Attachment of Alkyne Residue - Approach 2

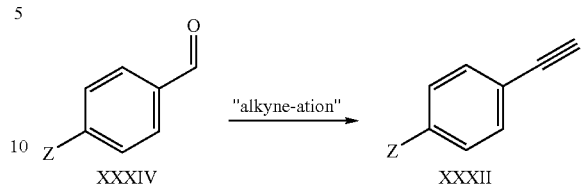

The reaction is a combination of an olefination reaction of the aldehyde XXXIV followed by a so-called Fritsch-Buttenberg-Wiechel rearrangement of an intermediately formed vinyl carbene or carbenoid. The reaction may be carried out with only one reagent or two reagents that execute the overall transformation in two separate steps. The one reagent procedure may be conducted with an situ generated anion of a diazotized reagent such as e.g. dialkyldiazomethylphosphonate and trimethylsilyldiazomethane. The anion of the latter reagent is usually generated with strong bases such as e.g. lithium diisopropylamide, butyl lithium, lithium hexamethyldisilazide, and potassium tert-butoxide in inert solvents such as e.g. tetrahydrofuran, ether, 1,2-dimethoxyethane, hexane or mixtures thereof at temperatures below 0° C. The anion thus obtained is reacted with the aldehyde at temperatures between −80 and 120° C., preferably at −60° C. and 60° C. to furnish the desired alkyne. Dialkyl-1-diazo-2-oxopropylphosphonates are suitable precursors for the anions of dialkyldiazomethylphosphonates that transform into the reactive alkyne-ating species in the presence of a base such as e.g. potassium or cesium carbonate, alcoxides such as e.g. sodium isopropoxide or methoxide, in solvents such as e.g. alcohols such as e.g. methanol, ethanol, isopropanol, water, acetonitrile, tetrahydrofutran, toluene, dichloromethane, or mixtures thereof. The precursor, dialkyl-1-diazo-2-oxopropylphosphonate, itself can be generated in situ by employing dialkyl-2-oxopropylphosphonate in conjunction with a diazotizing reagent such as e.g. p-toluenesulfonylazide. The reactive agent or its immediate precursor, dialkyl-1-diazo-2-oxopropylphosphonate, are combined in the presence of the adjuvants and in the solvents mentioned at temperatures of −30° C. to 120° C. to afford the alkyne product in one reaction pot. Among the two reagent combinations that may be applied here the Corey-Fuchs reaction and a process developed by researchers of DuPont (see *J. Org. Chem.* 2000, 65, pp. 1889-1891 and references quoted therein) are particularly worth mentioning.

The following scheme 15 presents a particularly preferred approach to access the desired compounds.

Scheme 15: Preferred Synthetic Route to Target Molecules

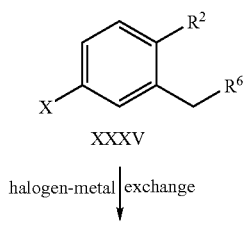

halogen-metal exchange

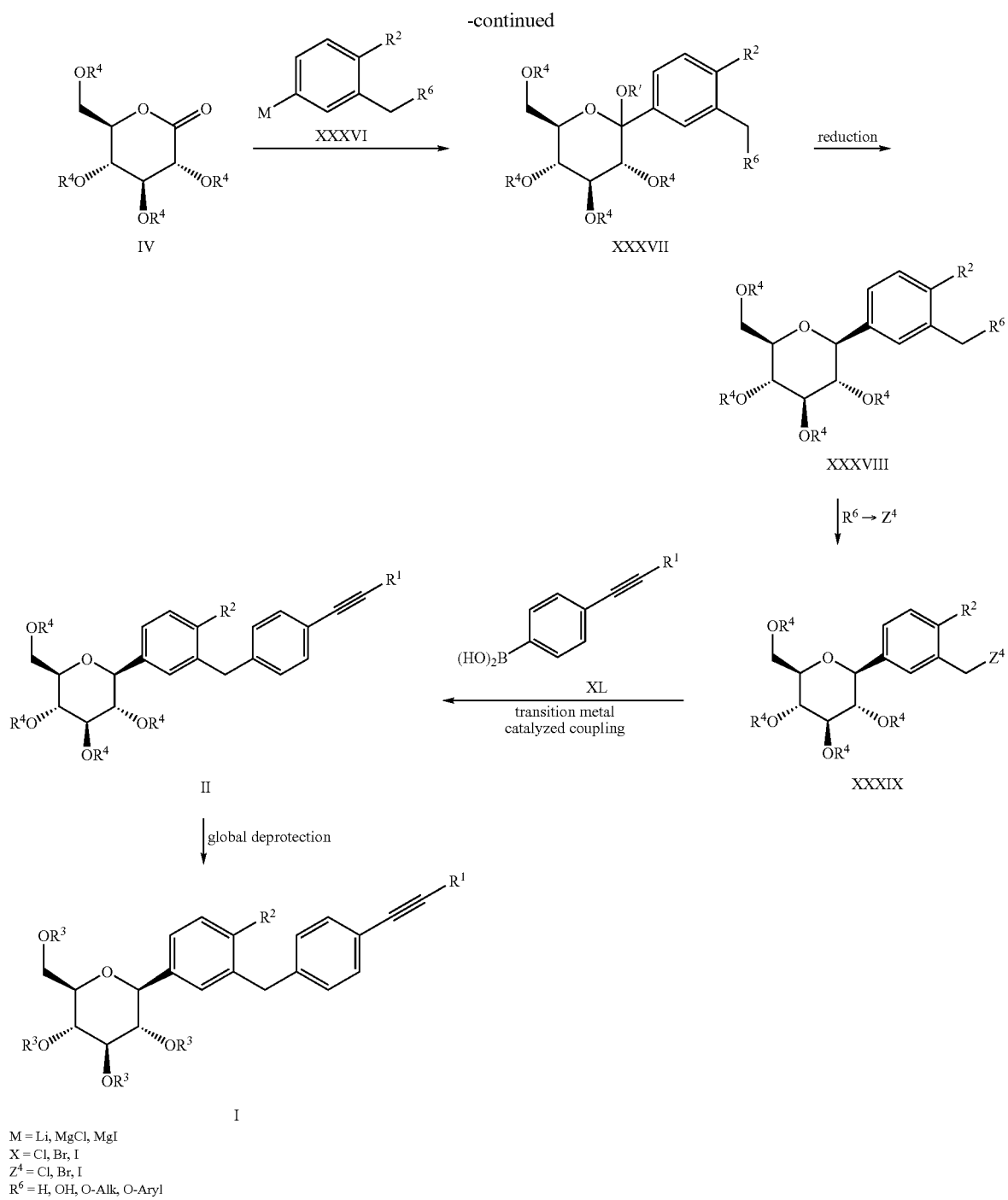

M = Li, MgCl, MgI
X = Cl, Br, I
$Z^4$ = Cl, Br, I
$R^6$ = H, OH, O-Alk, O-Aryl

In the above reaction scheme preferred meanings of the individual groups are:

$R^1$ and $R^2$ are defined as hereinbefore.

$R^4$ preferably denotes hydrogen, ($C_{1-8}$-alkyl)carbonyl which may be substituted with $C_{1-4}$-alkoxy, ($C_{1-8}$-alkyl)oxycarbonyl, ($C_{3-6}$-alkenyl)carbonyl, arylcarbonyl, $C_{1-6}$-alkoxymethyl, $R^aR^bR^cSi$—, —$CR^aR^bOR^c$. If two adjacent groups $R^4$ are linked with each other to form a bridging group it consists of $SiR^aR^b$, C=O, $CR^aR^b$ or $CR^aOR^b$—$CR^aOR^b$, wherein $R^aR^bR^c$ are defined as hereinbefore and each alkyl group may be substituted with up to three substituents selected from fluorine, chlorine, $C_{1-3}$-alkyl, $R^aR^bR^cSi$— and $C_{1-4}$-alkoxy.

$R^6$ preferably denotes hydrogen, hydroxy, $C_{1-6}$-alkyloxy or aryloxy, more preferably $C_{1-6}$-alkyloxy or aryloxy.

The synthetic sequence starts off with the metalation of the aglycon part XXXV that bears the residue $R^2$ and a bromine or iodine atom and in addition thereto a group —$CH_2$—$R^6$ wherein the potential leaving group $R^6$ denotes H, $C_{1-4}$-alkoxy or aryloxy. The addition of the metalated aglycon to the protected gluconolactone IV may be carried out as described before, in particular with respect to Scheme 2. After quenching of the adduct with an acid such as acetic acid, hydrochloric acid, sulfuric acid or methanesulfonic acid in an alcohol such as methanol or ethanol the corresponding alkoxy adduct XXXVII may be obtained. The ensuing reduction to access the C-glucoside XXXVIII is achieved with one of the possible methods described before, in particular with respect to Scheme 2. The use of a silane such as triethylsilane in conjunction with a Lewis acid such as borontrifluoride etherate is one quite general possibility for this type of reduction.

The next step transforms the group $R^6$ into a group $Z^4$ being chlorine, bromine or iodine atom, preferably bromine atom. Starting from $R^6$ equals H, only applicable to the compounds bearing chlorine (as substituent $R^2$) on the phenyl ring, the bromide may be introduced via a radical substitution reaction. N-bromosuccinimide or bromine in combination with a radical starter such as e.g. azobisisobutyronitrile or dibenzoylperoxide in a halogenated hydrocarbon such as e.g. tetrachloromethane, chloroform, dichloromethane or 1,2-dichloroethane at 0° C. to 120° C. may be suitable reaction conditions for this transformation. More preferably the replacement of an alkoxy or aryloxy group $R^6$ at the benzylic positon by chloride, bromide or iodide is employed. In this case $R^6$ denotes a leaving group that may be replaced under the action of e.g. boron trichloride, tin tetrachloride, aluminum chloride, zinc chloride, phosphorous pentachloride, iodine monochloride, hydrochloric acid, boron tribromide, trimethylsilyl bromide, hydrobromic acid, sodium iodide in conjunction with borontrifluoride etherate or aluminum chloride or trifluoromethanesulfonic acid or trichloromethylsilane or boron tribromide, trimethylsilyl iodide, or hydriodic acid with the corresponding halide. Suitable solvents are for example dichloromethane, toluene, hexane, cyclohexane, dioxane, ether, acetonitrile, water, alcohol, dimethylsulfoxide, dimethylformamide or acetic acid. The preferred product XXXIX is the corresponding bromide ($Z^4$=Br) that is preferably prepared from the corresponding benzyl aryl or alkyl ether XXXVIII ($R^6$ denotes alkyloxy or aryloxy) under the action of hydrobromic acid in acetic acid at 0° C. to 100° C.

The following coupling of the halide XXXIX with the boronic acid XL is a Suzuki-type reaction that has been described before, in particular with respect to Schme 11. Particularly preferred reaction conditions for this transformation comprise a palladium source such as palladium chloride or bromide or acetate as catalyst precursor, sodium hydroxide, potassium or sodium carbonate or potassium phosphate as base and dioxane, water, acetone, methanol, ethanol, tetrahydrofuran, xylenes or toluene as solvent. The addition of a phosphine ligand or a preformed palladium complex with the ligand may be advantageous. The reactions are preferably carried out between 0° C. and 130° C. Conditions to remove the protective groups in II to furnish the end product I have been described before, in particular with respect to Scheme 1.

The following description generally refers to all reactions and synthetic routes as described hereinbefore and hereinafter.

Any reactive group present such as ethynyl, hydroxy, amino, alkylamino or imino groups may be protected during the reaction by conventional protecting groups which are cleaved again after the reaction.

For example, a protecting group for a hydroxy group may be a trimethylsilyl, acetyl, trityl, benzyl or tetrahydropyranyl group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

Protecting groups for a terminal alkyne are e.g. silyl groups such as trimethylsilyl, biphenyldimethylsilyl or triisopropylsilyl, and 2-hydroxy-isopropyl.

Moreover, the compounds and intermediates obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds and intermediates obtained which occur as racemates may be separated by methods known per se (cf. Allinger N. L. and Eliel E. L. in "Topics in Stereochemistry", Vol. 6, Wiley Interscience, 1971) into their optical antipodes and compounds or intermediates with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds and intermediates of the present invention may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

The compounds according to the invention are advantageously also obtainable using the methods described in the examples that follow, which may also be combined for this purpose with methods known to the skilled man from the literature, for example, particularly the methods described in WO 98/31697, WO 01/27128, WO 02/083066, WO 03/099836, WO 2004/063209 and WO 2005/092877.

Some terms used above and hereinafter to describe the compounds according to the invention will now be defined more closely.

The term halogen denotes an atom selected from the group consisting of F, Cl, Br and I, particularly F, Cl and Br.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc. . If not specified otherwise the term alkyl preferably denotes a $C_{1-6}$-alkyl-group, more preferably a $C_{1-4}$-alkyl-group, most preferably a $C_{1-3}$-alkyl-group.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc. Preferably the term $C_{3-7}$-cycloalkyl denotes saturated monocyclic groups.

The term $C_{5-n}$-cycloalkenyl denotes a $C_{5-n}$-cycloalkyl group which is as hereinbefore defined and additionally has at least one unsaturated C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term tri-($C_{1-4}$-alkyl)silyl comprises silyl groups which have identical or two or three different alkyl groups.

The term di-($C_{1-3}$-alkyl)amino comprises amino groups which have identical or two different alkyl groups.

The term aryl preferably denotes naphthyl or phenyl, more preferably phenyl.

The nomenclature in structural formulas used above and hereinafter, in which a bond of a substituent of a cyclic group, as e.g. a phenyl ring, is shown towards the centre of the cyclic group, denotes, unless otherwise stated, that this substituent may be bound to any free position of the cyclic group bearing an H atom.

In the foregoing and following text, H atoms of hydroxyl groups are not explicitly shown in every case in structural formulae. The Examples that follow are intended to illustrate the present invention without restricting it. In case the pressure is indicated in the unit "Torr", the corresponding values can be converted into SI units by using 1 torr=133.322 Pa. In view of their ability to inhibit the SGLT activity, compounds of the formula I according to the invention are suitable for the preparation of pharmaceutical compositions for the treatment and/or preventative treatment of all those conditions or diseases which may be affected by the inhibition of the SGLT activity, particularly the SGLT-2 activity. Therefore, the compounds of the formula I are particularly suitable for the preparation of pharmaceutical compositions for prevention or treatment of diseases, particularly metabolic disorders, or conditions such as diabetes mellitus.

The following examples of synthesis serves to illustrate method of preparing a compound of the formula I and intermediates thereof. It is to be regarded only as a possible method described by way of example, without restricting the invention to its contents.

Experimental Procedures

EXAMPLE I

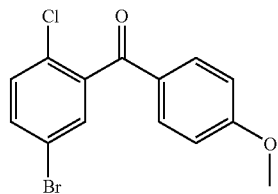

(5-bromo-2-chloro-phenyl)-(4-methoxy-phenyl)-methanone 38.3 ml oxalyl chloride and 0.8 ml of dimethylformamide are added to a mixture of 100 g of 5-bromo-2-chloro-benzoic acid in 500 mL dichloromethane. The reaction mixture is stirred for 14 h, then filtered and separated from all volatile constituents in a rotary evaporator. The residue is dissolved in 150 ml dichloromethane, the resulting solution is cooled to −5° C., and 46.5 g of anisole are added. Then 51.5 g of aluminum trichloride are added batchwise so that the temperature does not exceed 5° C. The solution is stirred for another 1 h at 1 to 5° C. and then poured onto crushed ice. The organic phase is separated, and the aqueous phase is extracted three times with dichloromethane. The combined organic phases are washed with aqueous 1 M hydrochloric acid, twice with 1 M sodium hydroxide solution, and with brine. The organic phase is dried, the solvent is removed in vacuo, and the residue is recrystallized from ethanol.

Yield: 86.3 g (64% of theory)

Mass spectrum (ESI$^+$): m/z=325/327/329 (Br+Cl) [M+H]$^+$

The following compound may be obtained analogously to Example I:

(1)  (5-bromo-2-methyl-phenyl)-(4-methoxy-phenyl)-methanone

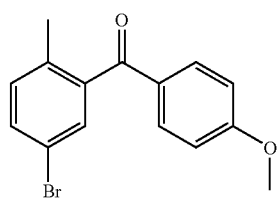

Mass spectrum (ESI$^+$): m/z=305/307 (Br) [M+H]$^+$

EXAMPLE II

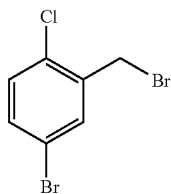

4-bromo-2-bromomethyl-1-chloro-benzene 4.0 g N-bromosuccinimide are slowly added to a solution of 5.0 g of 4-bromo-1-chloro-2-hydroxymethyl-benzene and 5.9 g triphenylphosphine in 50 mL of tetrahydrofuran chilled to 5° C. After 1 h stirring at ambient temperature the precipitate is filtered off, and the solvent is eliminated in vacuo. The residue is purified by chromatography on silica gel (cyclohexane/ethyl acetate 50:1).

Yield: 4.9 g (76% of theory)
Mass spectrum (EI): m/z=282/284/286/288 (2Br+Cl) [M]$^+$

EXAMPLE III

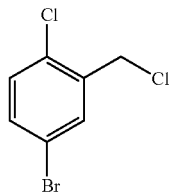

4-bromo-2-chloromethyl-1-chloro-benzene

A solution of 40.0 g 4-bromo-1-chloro-2-hydroxymethyl-benzene and 60 mL thionyl chloride in 150 mL dichloromethane are stirred at 45-50° C. for 5 h. Then the solvent and the excess reagent is removed in vacuo.

Yield: 43.2 g (100% of theory)
Mass spectrum (EI): m/z=238/240/242/244 (Br+2Cl$_2$) [M]$^+$

EXAMPLE IV

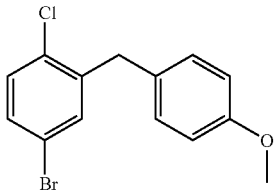

4-bromo-1-chloro-2-(4-methoxy-benzyl)-benzene

A solution of 86.2 g (5-bromo-2-chloro-phenyl)-(4-methoxy-phenyl)-methanone and 101.5 mL triethylsilane in 75 mL dichloromethane and 150 mL acetonitrile is cooled to 10° C. 50.8 mL of boron trifluoride etherate are added so that the temperature does not exceed 20° C. The solution is stirred for 14 h at ambient temperature, before another 9 mL triethylsilane and 4.4 mL boron trifluoride etherate are added. The solution is stirred for a further 3 h at 45 to 50° C. and then cooled to ambient temperature. A solution of 28 g potassium hydroxide in 70 mL of water is added, and the resultant mixture is stirred for 2 h. Then the organic phase is separated, and the aqueous phase is extracted three times with diisopropylether. The combined organic phases are washed twice with 2 M potassium hydroxide solution and once with brine and then dried over sodium sulfate. After the solvent is removed, the residue is washed with ethanol and dried at 60° C.

Yield: 50.0 g (61% of theory)
Mass spectrum (ESI$^+$): m/z=310/312/314 (Br+Cl) [M+H]$^+$ The following compound may be obtained analogously to Example IV:

(1) (5-bromo-2-methyl-phenyl)-(4-methoxy-phenyl)-methane

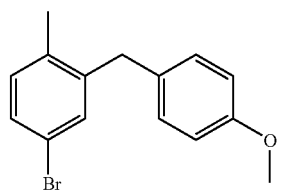

Mass spectrum (EI$^+$): m/z=290/292 (Br) [M]$^+$

EXAMPLE V

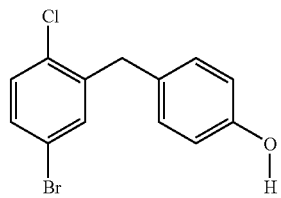

4-(5-bromo-2-chloro-benzyl)-phenol

A solution of 14.8 g 4-bromo-1-chloro-2-(4-methoxy-benzyl)-benzene in 150 mL dichloromethane is cooled in an ice bath. Then 50 mL of a 1 M solution of boron tribromide in dichloromethane are added, and the solution is stirred for 2 h at ambient temperature. The solution is then cooled in an ice bath again, and saturated potassium carbonate solution is added dropwise. At ambient temperature the mixture is adjusted with aqueous 1 M hydrochloric acid to a pH of about 1, the organic phase is separated, and the aqueous phase is extracted another three times with ethyl acetate. The combined organic phases are dried over sodium sulfate, and the solvent is removed completely.

Yield: 13.9 g (98% of theory)
Mass spectrum (ESI$^-$): m/z=295/297/299 (Br+Cl) [M−H]$^-$ The following compound may be obtained analogously to Example V:

(1) 4-(5-bromo-2-methyl-benzyl)-phenol

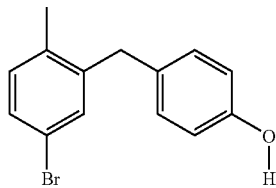

Mass spectrum (ESI[31]): m/z=275/277 (Br+Cl) [M−H]⁻

EXAMPLE VI

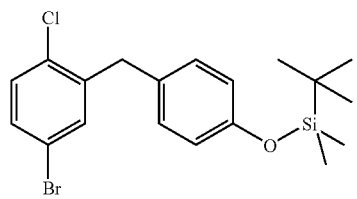

[4-(5-bromo-2-chloro-benzyl)-phenoxy]-tert-butyl-dimethyl-silane

A solution of 13.9 g 4-(5-bromo-2-chloro-benzyl)-phenol in 140 mL dichloromethane is cooled in an ice bath. Then 7.54 g tert-butyldimethylsilylchlorid in 20 mL dichloromethane are added followed by 9.8 mL triethylamine and 0.5 g 4-dimethylaminopyridine. The solution is stirred for 16 h at ambient temperature and then diluted with 100 mL dichloromethane. The organic phase is washed twice with aqueous 1 M hydrochloric acid and once with aqueous sodium hydrogen carbonate solution and then dried over sodium sulfate. After the solvent has been removed, the residue is filtered through silica gel (cyclohexane/ethyl acetate 100:1).

Yield: 16.8 g (87% of theory)
Mass spectrum (EI): m/z=410/412/414 (Br+Cl) [M]⁺

The following compound may be obtained analogously to Example VI:

(1) [4-(5-bromo-2-methyl-benzyl)-phenoxy]-tert-butyl-dimethyl-silan

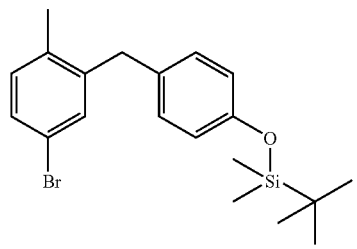

Mass spectrum (ESI⁺): m/z=391/393 (Br) [M+H]⁺

EXAMPLE VII

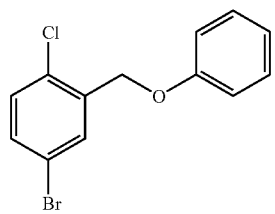

4-bromo-1-chloro-2-phenoxymethyl-benzene

To a mixture of 7.1 g phenol and 11.1 g potassium carbonate in 100 mL ethanol are added 19.5 g 4-bromo-2-bromomethyl-1-chloro-benzene. The mixture is stirred at ambient temperature over night. The ethanol is evaporated, and water is added to the residue. The resulting mixture is extracted with ethyl acetate, the combined extracts are dried over sodium sulfate, and the solvent is removed. The residue is purified by chromatography on silica gel (cyclohexane/ethyl acetate 70:30).

Yield: 16.8 g (82% of theory)
Mass spectrum (ESI⁺): m/z=296/298/300 (Br+Cl) [M]⁺

EXAMPLE VIII

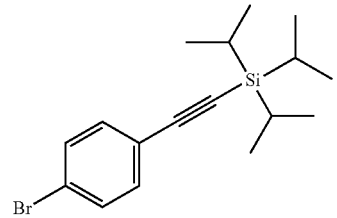

1-bromo-4-triisopropylsilylethynyl-benzene

Under argon 11.6 mL triisopropylsilylacetylen and 14.4 mL triethylamine followed by 0.2 g copper iodide and 0.73 g bis-(triphenylphosphine)-palladium dichloride are added to an oxygen-free solution of 15.0 g 1-bromo-4-iodo-benzene in 150 mL dry tetrahydrofuran. The solution is stirred for 16 h at ambient temperature and then filtered through Celite and evaporated down. The residue is chromatographed through silica gel (cyclohexane).

Yield: 17.4 g (100% of theory )
Mass spectrum (ESI⁺): m/z=336/338 (Br) [M]⁺

The following compounds may be obtained analogously to Example VIII:

(1) 4-(triisopropylsilyl-ethynyl)phenylboronic acid
4-iodo-phenylboronic acid is used as starting material.

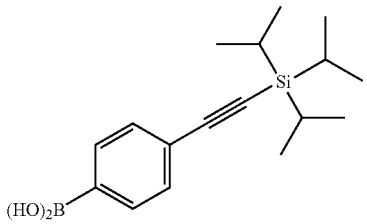

Mass spectrum (ESI⁻): m/z=347 [M+HCOO]⁻

(2) 4-(trimethylsilyl-ethynyl)phenylboronic acid 4-iodophenylboronic acid is used as starting material.

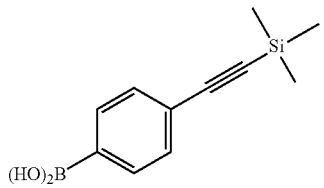

Mass spectrum (ESI⁻): m/z=263 [M+HCOO]⁻

EXAMPLE IX

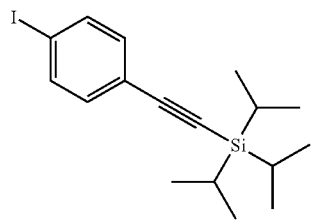

(4-iodo-phenylethynyl)-triisopropyl-silane

Under argon 18.0 g sodium iodide (dry), 0.6 g copper iodide and 0.8 g N,N'-dimethyl-cyclohexane-1,2-diamine are added to a solution of 20.0 g (4-bromo-phenylethynyl)-triisopropyl-silane in 100 mL dioxane. The solution is refluxed with stirring for 24 h and then cooled to ambient temperature. 1% ammonia solution (100 mL) is added, and the mixture is extracted with ethyl acetate. After drying over sodium sulfate, the solvent is removed and the residue is purified on silica gel (cyclohexane).

Yield: 21.0 g (92% of theory)
Mass spectrum (EI): m/z=384 [M]⁺

EXAMPLE X

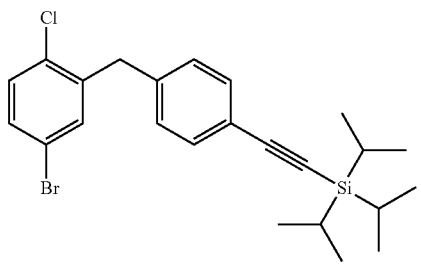

[4-(5-bromo-2-chloro-benzyl)-phenylethynyl]-triisopropyl-silane

Under argon 0.66 ml of a 2 M solution of isopropylmagnesium chloride in tetrahydrofuran are added dropwise to a solution of 0.50 g (4-iodo-phenylethynyl)-triisopropyl-silane in 2.2 mL dry tetrahydrofuran chilled to −25° C. The solution is stirred for 30 min at −25° C. and then combined with 0.26 mL of a 1 M solution of CuCN*2 LiCl in tetrahydrofuran (prepared by dissolving CuCN and LiCl in the ratio 1:2). Shortly afterwards, 0.35 g 4-bromo-2-bromomethyl-1-chloro-benzene are added and the reaction mixture is warmed up to −5° C. in the cooling bath. After 6 h stirring at −5° C., the solution is warmed to ambient temperature and stirred overnight. Then a mixture of saturated ammonium chloride solution and 25% ammonia solution (9:1) is added, and the resulting mixture is added to water. The organic phase is separated, the aqueous phase is extracted with ethyl acetate, the combined organic phases are dried over sodium sulfate, and the solvent is removed. The residue is purified through silica gel (cyclohexane).

Yield: 0.28 g (50% of theory)
Mass spectrum (EI): m/z=461/463/465 (Br+Cl) [M+H]⁺

The following compound may be obtained analogously to Example X:

(1) [4-(5-bromo-2-methyl-benzyl)-phenylethynyl]-triisopropyl-silane

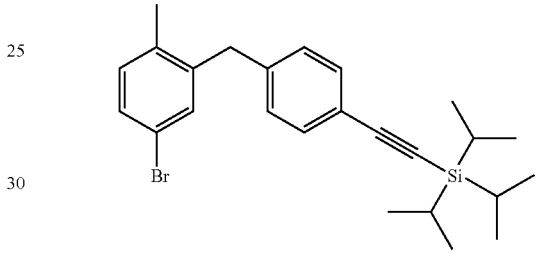

EXAMPLE XI

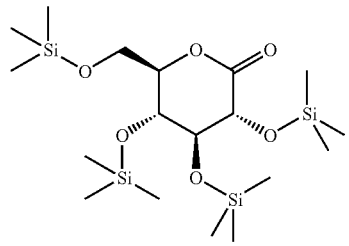

2,3,4,6-tetrakis-O-(trimethylsilyl)-D-glucopyranone

A solution of 20 g D-glucono-1,5-lactone and 98.5 mL N-methylmorpholine in 200 mL of tetrahydrofuran is cooled to −5° C. Then 85 ml trimethylsilyl chloride are added dropwise so that the temperature does not exceed 5° C. The solution is then stirred for 1 h at ambient temperature, 5 h at 35° C. and again for 14 h at ambient temperature. After the addition of 300 mL of toluene, the solution is cooled in an ice bath, and 500 mL of water are added so that the temperature does not exceed 10° C. The organic phase is then separated and washed with aqueous sodium dihydrogen phosphate solution, water, and brine. The solvent is removed in vacuo and the residue is azeotropically dried with toluene.

Yield: 52.5 g (approx. 90% pure)
Mass spectrum (ESI⁺): m/z=467 [M+H]⁺

EXAMPLE XII

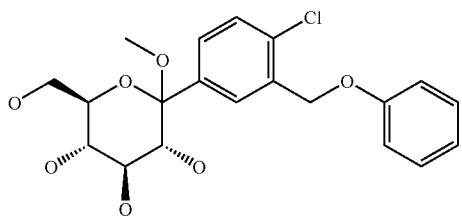

1-Chloro-4-(1-methoxy-D-glucopyranos-1-yl)-2-(phenoxymethyl)-benzene

A solution of 14.40 g 4-bromo-1-chloro-2-phenoxymethyl-benzene in 120 mL dry tetrahydrofuran is cooled to −78° C. under argon. 33.5 mL of a 1.7 M solution of n-butyl lithium in hexane are slowly added dropwise to the cooled solution. The solution is stirred for 45 min at −78° C. and then a −78° C.-cold solution of 25.10 g (ca. 90% pure) of 2,3,4,6-tetrakis-O- (trimethylsilyl)-D-glucopyranone in 80 mL tetrahydrofuran is added through a transfer needle. The resulting solution is stirred for 1 h at −78° C., and then 150 mL of a 1% solution of acetic acid in water is added. After warming to room temperature, the resultant reaction mixture is extracted with ethyl acetate, the combined organic extracts are washed with brine and dried over sodium sulfate. After removal of the solvent the residue is dissolved in 90 mL methanol and treated with 1 mL methanesulfonic acid. The solution is stirred at room temperature over night and then neutralized with triethylamine. The solvent is removed under reduced pressure and the residue is dissolved in 250 mL ethyl acetate. The organic solution is washed with water and brine and dried over sodium sulfate. After removal of the solvent, the crude product is submitted to reduction without further purification.

Yield: 17.20 g (crude product)

Mass spectrum (ESI$^+$): m/z=433/435 (Cl) [M+Na]$^+$

The following compound may be obtained analogously to Example XII:

(1) 1-chloro-4-(1-methoxy-D-glucopyranos-1-yl)-2-(4-triisopropylsilylethynyl-benzyl)-benzene

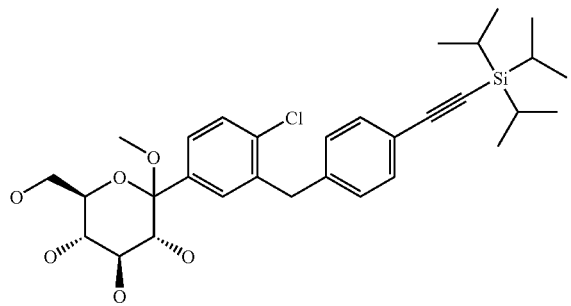

Mass spectrum (ESI$^+$): m/z=592/594 (Cl) [M+NH$_4$]$^+$

EXAMPLE XIII

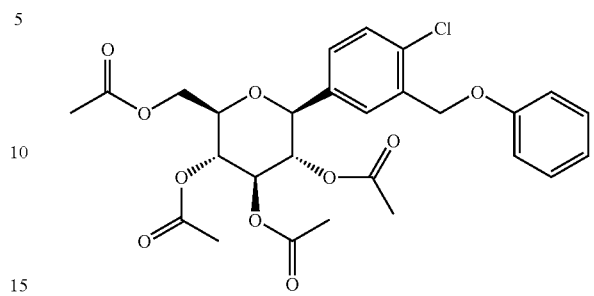

1-Chloro-4-(2,3,4,6-tetra-O-acteyl-D-glucopyranos-1-yl)-2-(phenoxymethyl)-benzene A solution of 17.20 g 1-chloro-4-(1-methoxy-D-glucopyranos-1-yl)-2-(phenoxymethyl)-benzene and 13.6 mL triethylsilane in 120 mL dichloromethane and 360 mL acetonitrile is cooled to −10° C. Then 8.4 mL boron trifluoride etherate are added dropwise so that the solution temperature remained below 0° C. The resultant solution is stirred for 0.5 h in an ice bath and then warmed to room temperature. Aqueous sodium hydrogen carbonate solution is added, and the resulting mixture is stirred for 0.5 h. The organic layer is separated and the aqueous layer is extracted with ethyl acetate. The combined organic layers are washed with brine and dried over sodium sulfate. The solvent is removed, and the residue is taken up in 200 mL dichloromethane. The solution is cooled in an ice-bath and 36 mL pyridine, 40 mL acetic anhydride and 0.5 g 4-dimethylaminopyridine are added. The solution is stirred for 1 h at ambient temperature and then diluted with 100 mL dichloromethane. The organic solution is washed twice with 1 M hydrochloric acid and dried over sodium sulfate. After the solvent is removed, the residue is recrystallized from ethanol to furnish the product as white crystals.

Yield: 7.30 g (32% of theory)

Mass spectrum (ESI$^+$): m/z=566/568 (Cl) [M+NH$_4$]$^+$

The following compounds may be obtained analogously to Example XIII:

(1) 1-chloro-4-(2,3,4,6-tetra-O-acetyl-β-D-glucopyranos-1-yl)-2-(4-triisopropylsilylethynyl-benzyl)-benzene

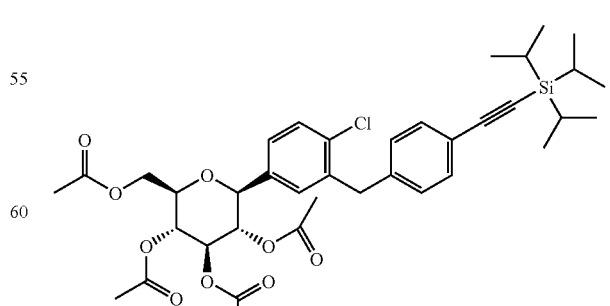

Mass spectrum (ESI$^+$): m/z=730/732 (Cl) [M+NH$_4$]$^+$ (2) 1-chloro-4-(2,3,4,6-tetra-O-acetyl-β-D-glucopyranos-1-yl)-2-(4-triisopropylsilylethynyl-benzyl)-benzene

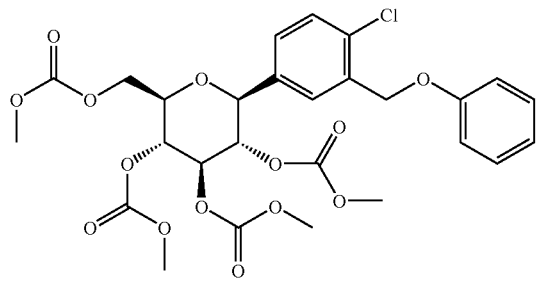

Mass spectrum (ESI⁺): m/z=630/632 (Cl) [M+NH₄]⁺

The reduced compound was treated with methyl chloroformate instead of acetic anhydride according to the procedure described above.

EXAMPLE XIV

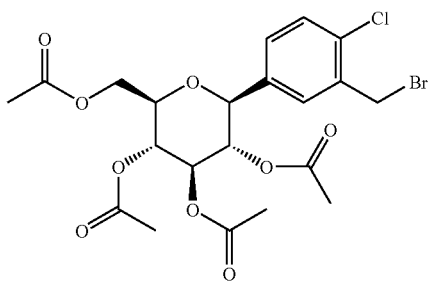

1-Chloro-4-(2,3,4,6-tetra-O-acteyl-D-glucopyranos-1-yl)-2-bromomethyl-benzene

To a solution of 6.04 g 1-chloro-4-(1-methoxy-D-glucopyranos-1-yl)-2-phenyloxymethyl-benzene in 200 mL acetic acid is added 200 mL of a solution of 33% hydrobromic acid in acetic acid. The solution is stirred for 2 h at ambient temperature and then cooled in an ice-bath. The reaction mixture is neutralized with chilled aqueous saturated potassium carbonate solution, and the resultant mixture is extracted with ethyl acetate. The combined organic extracts are dried over sodium sulfate, and the solvent is removed in vacuo. The residue is taken up in ethyl aceate/cyclohexane (1:3), and the precipitate is separated by filtration and dried at 50° C. to give the pure product.

Yield: 4.50 g (76% of theory)

Mass spectrum (ESI⁺): m/z=552/554/556 (Br+Cl) [M+NH₄]⁺

The following compound may be obtained analogously to Example XIV:

(1) 1-Chloro-4-(2,3,4,6-tetra-O-benzoyl-D-glucopyranos-1-yl)-2-bromomethyl-benzene

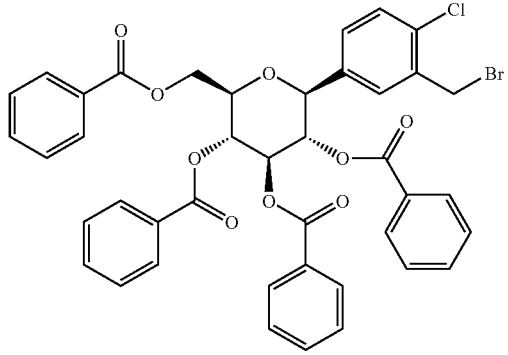

Mass spectrum (ESI⁺): m/z=800/802/804 (Br+Cl) [M+NH₄]⁺

EXAMPLE XV

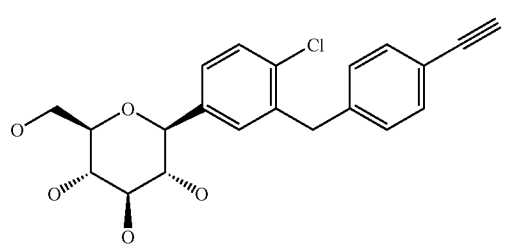

1-Chloro-4-(β-D-glucopyranos-1-yl)-2-(4-ethynyl-benzyl)-benzene

To a solution of 3.25 g 1-chloro-4-(2,3,4,6-tetra-O-acetyl-D-glucopyranos-1-yl)-2-bromomethyl-benzene, 1.46 g 4-trimethylsilylethynyl-phenylboronic acid and 2.10 potassium carbonate in 45 mL acetone and 15 mL water under argon is added 32 mg palladium dichloride. The reaction mixture is stirred for 10 h at ambient temperature and then diluted with brine. The resultant mixture is extracted with ethyl acetate, the combined extracts are dried over sodium sulfate, and the solvent is removed in vacuo. The residue is taken up in 40 mL methanol, and 8 mL of 4 M aqueous potassium hydroxide solution are added. The solution is stirred at ambient temperature for 1 h and then neutralized with 1 M hydrochloric acid. The methanol is evaporated, and the residue is diluted with brine and extracted with ethyl acetate. The organic extracts collected are dried over sodium sulfate, and the solvent is removed. The residue is chromatographed on silica gel (dichloromethane/methanol 1:0->6:1).

Yield: 1.37 g (58% of theory) Mass spectrum (ESI⁺): m/z=406/408 (Cl) [M+H]⁺

1-Chloro-4-(2,3,4,6-tetra-O-benzoyl-D-glucopyranos-1-yl)-2-bromomethyl-benzene can be employed for the reaction described above as well.

The following compounds may be obtained analogously to Example XV:

(1) [4-(5-bromo-2-chloro-benzyl)-phenylethynyl]-triisopropyl-silane 4-(triisopropylsilyl-ethynyl)phenylboronic acid and 5-bromo-2-chloro-benzyl bromide are the coupling partners to submit to the above-described reaction conditions

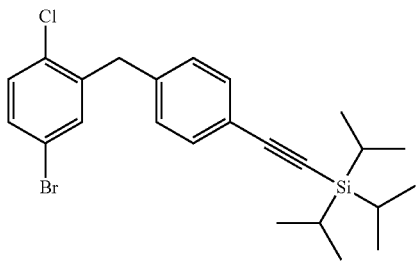

Mass spectrum (ESI⁺): m/z=461/463/465 (Br+Cl) [M+H]⁺

(2) [4-(5-bromo-2-methyl-benzyl)-phenylethynyl]-triisopropyl-silane 4-(triisopropylsilyl-ethynyl)phenylboronic acid and 5-bromo-2-methyl-benzyl bromide (known com pound) are the coupling partners to submit to the above-described reaction conditions

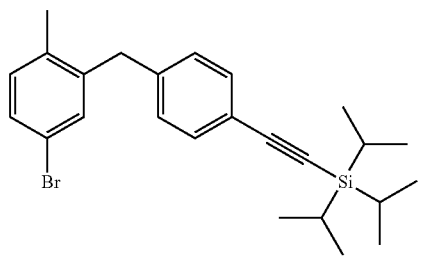

EXAMPLE XVI

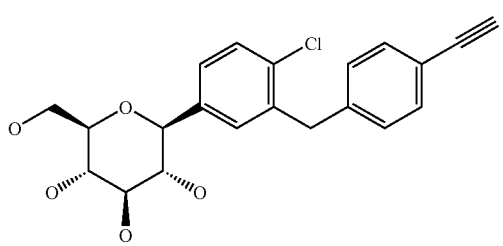

1-Chloro-4-(β-D-glucopyranos-1-yl)-2-(4-ethynyl-benzyl)-benzene 0.77 mL of a 1 M solution of tetrabutylammonium fluoride in tetrahydrofuran are added to a solution of 0.55 g 1-chloro-4-(2,3,4,6-tetra-O-acetyl-β-D-glucopyranos-1-yl)-2-(triisopropylsilylet hynyl-benzyl)-benzene in 2 mL tetrahydrofuran. The solution is stirred for 1 h at ambient temperature. Then 4 mL methanol and 0.85 mL 4 M potassium hydroxide solution are added and the resultant solution is stirred for a further hour at ambient temperature. The solution is neutralized with 1 M hydrochloric acid and then the methanol is evaporated off. The residue is combined with aqueous sodium chloride solution and extracted with ethyl acetate. The combined organic extracts are dried over sodium sulfate, and the solvent is removed. The residue is chromatographed on silica gel (dichloromethane/methanol 19:1→2:1).

Yield: 0.15 g (50% of theory)

Mass spectrum (ESI⁺): m/z=406/408 (Cl) [M+NH₄]⁺

The following compound may be obtained analogously to Example XVI:

(1) 4-(β-D-glucopyranos-1-yl)-3-(4-ethynyl-benzyl)-4-methyl-benzene

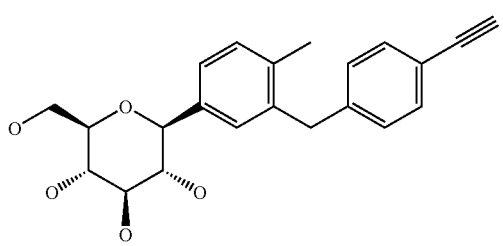

Mass spectrum (ESI⁺): m/z=386 [M+NH₄]⁺

EXAMPLE XVII

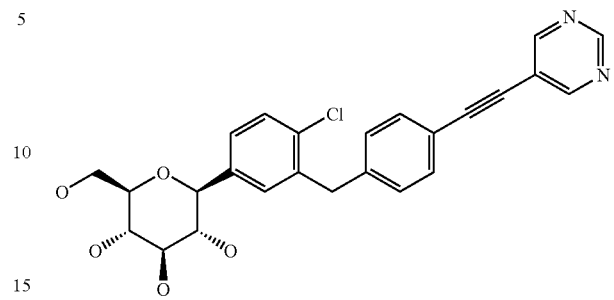

1-Chloro-4-(β-D-glucopyranos-1-yl)-2-[4-(pyrimidine-5-yl-ethynyl)-benzyl]-benzene 37 mg copper iodide, 67 mg bis-(triphenylphosphine)-palladium dichloride and 0.46 mL triethylamine are added to an oxygen-free solution of 0.35 g 1-chloro-4-(β-D-glucopyranos-1-yl)-2-(4-ethynyl-benzyl)-benzene and 0.2 g 5-bromopyrimidine in 1 mL dimethylformamide. The solution is stirred under argon atmosphere at 60° C. for 16 h. The reaction mixture is filtered through Celite and evaporated down. The residue is chromatographed on silica gel (dichloromethane/methanol 1:0→9:1).

Yield: 120 mg (29% of theory)

Mass spectrum (ESI⁺): m/z=467/469 (Cl) [M+H]⁺

The following compounds may be obtained analogously to Example XVII:

(1) 4-(β-D-glucopyranos-1-yl)-3-[4-(pyrimidine-5-yl-ethynyl)-benzyl]-4-methyl-benzene

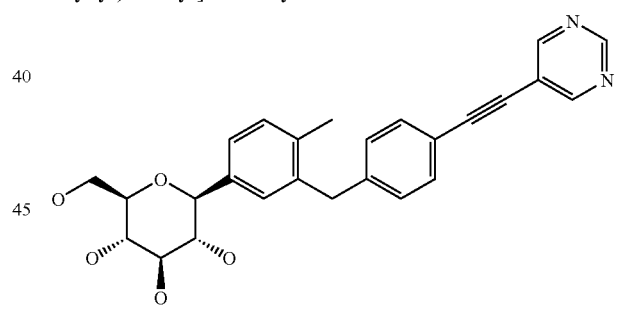

Mass spectrum (ESI⁺): m/z=447 [M+H]⁺

(2) 1-Chloro-4-(β-D-glucopyranos-1-yl)-2-[4-(6-methoxy-pyridine-3-yl)-ethynyl-benzyl]-benzene

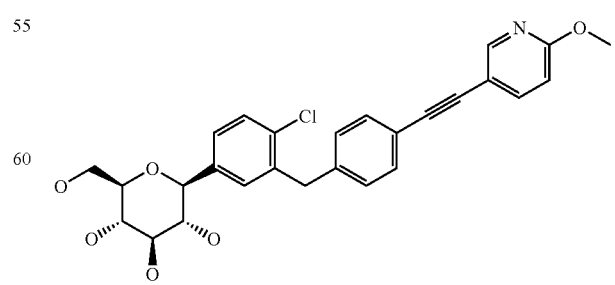

Mass spectrum (ESI⁺): m/z=496/498 (Cl) [M+H]⁺

(3) 1-Chloro-4-(β-D-glucopyranos-1-yl)-2-[4-(pyazine-2-yl-ethynyl)-benzyl]-benzene

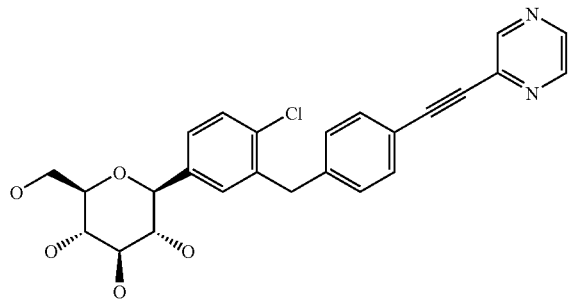

Mass spectrum (ESI+): m/z=467/469 (Cl) [M+H]+

(4) 1-Chloro-4-(β-D-glucopyranos-1-yl)-2-[4-(1 methyl-1H-pyrazol-4-yl)-ethynyl- benzyl]-benzene

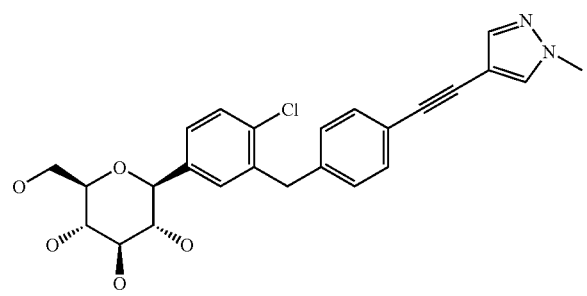

Mass spectrum (ESI+): m/z=469/471 (Cl) [M+H]+

(5) 1-Chloro-4-(β-D-glucopyranos-1-yl)-2-[4-(1H-pyrazol-4-yl-ethynyl)-benzyl]-benzene

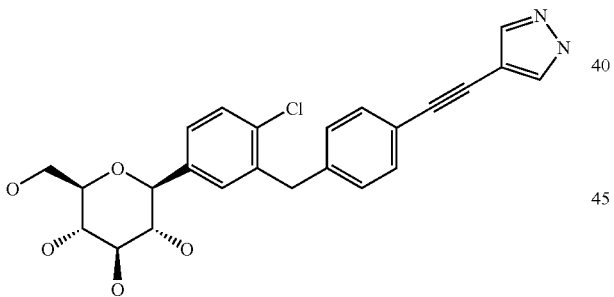

Mass spectrum (ESI+): m/z=455/457 (Cl) [M+H]+

(6) 1-Chloro-4-(β-D-glucopyranos-1-yl)-2-[4-(phenyl-ethynyl)-benzyl]-benzene

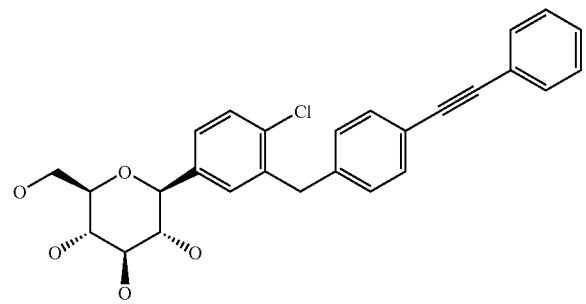

Mass spectrum (ESI+): m/z=482/484 (Cl) [M+NH4]+

(7) 1-Chloro-4-(β-D-glucopyranos-1-yl)-2-[4-(1-methylpyridine-2-one-5-yl)- ethynyl-benzyl]-benzene

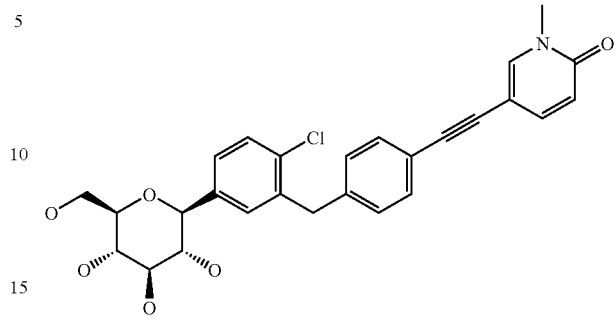

Mass spectrum (ESI+): m/z=496/498 (Cl) [M+H]+

The invention claimed is:
1. Process for preparing the compounds of general formula I,

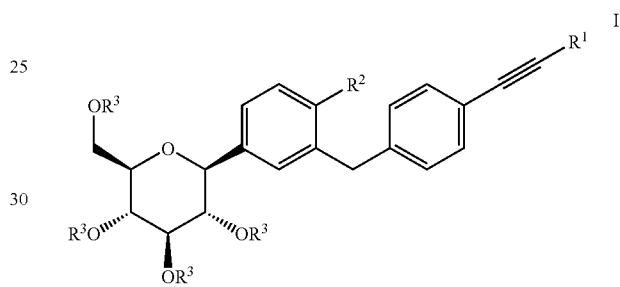

wherein
R$^1$ denotes hydrogen, or
  C$_{1-4}$-alkyl, C$_{3-7}$-cycloalkyl, tetrahydrofuranyl, or tetrahydropyranyl, which may be substituted with one to four substituents L2, or
  an aryl-group or a 5- or 6-membered monocyclic heteroaryl-group or a 8-, 9- or 10-membered bicyclic heteroaryl-group wherein said heteroaryl-groups have 1 to 4 heteroatoms independently selected from the group consisting of N, O and S; and wherein said heteroaryl-group may possess 1 or 2 carbonyl groups as part of the mono- or bicyclic aromatic ring-system; and
  wherein an N-atom of the heteroaryl ring-system may be oxidized to form the corresponding N-oxide; and
  wherein one or more methine groups in said aryl- and heteroaryl-group may be substituted independently of one another with a substituent L1; and
  wherein one or more imino-groups in said heteroaryl-group may be substituted independently of one another with a substituent R$^N$; and
R$^2$ denotes chlorine or methyl; and
R$^3$ denotes hydrogen;
R$^N$ independently of one another are selected from among C$_{1-3}$-alkyl; and
L1 independently of one another are selected from among fluorine, chlorine, bromine, C$_{1-3}$-alkyl, C$_{1-4}$-alkoxy and nitro;
L2 independently of one another are selected from among fluorine, chlorine, hydroxy, hydroxyl-C$_{1-4}$-alkyl, C$_{1-4}$-alkoxy, trifluoromethoxy, C$_{1-4}$-alkoxy-C$_{1-4}$-alkyl, cyano, C$_{1-4}$-alkyl, trifluoromethyl, amino, C$_{1-4}$-alkyl-carbonylamino, C$_{1-3}$-alkyl-amino and di(C$_{1-3}$-alkyl)-amino; and while by the aryl groups mentioned in the definition of the above groups are meant phenyl or naphthyl groups, which may be mono- or polysubstituted with L1;

characterised in that in a compound of general formula II

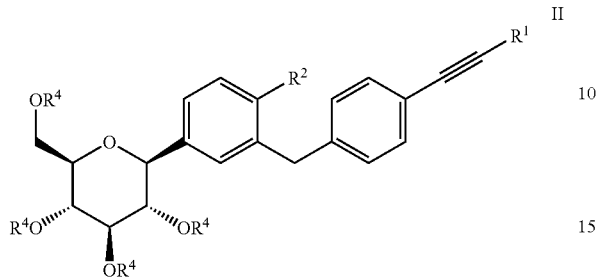

wherein $R^1$ and $R^2$ are defined as hereinbefore and $R^4$ independently of one another denote hydrogen, $C_{3-18}$-alkenyl, ($C_{1-18}$-alkyl)carbonyl, ($C_{1-18}$-alkyl)oxycarbonyl, ($C_{3-18}$-alkenyl)carbonyl, ($C_{3-18}$-alkenyl)oxycarbonyl, di-($C_{1-18}$-alkyl)aminocarbonyl, arylcarbonyl, aryl-($C_{1-3}$-alkyl)-carbonyl, aryl-$C_{1-3}$-alkyl, $C_{1-6}$-alkoxymethyl, aryl-$C_{1-3}$-alkoxy, $C_{1-4}$-alkylthioethyl, arylthioethyl, $C_{1-4}$-alkylsulfonylethyl, arylsulfonylethyl, $R^aR^bR^cSi$—, —$CR^aR^bOR^c$, wherein two adjacent groups $R^4$ may be linked with each other to form a bridging group $SiR^aR^b$, $CR^aR^b$ or $CR^aOR^b$—$CR^aOR^b$ and wherein each alkyl group may be substituted with up to three substituents selected from fluorine, chlorine, $C_{1-3}$-alkyl, $R^aR^bR^cSi$, $C_{1-4}$-alkoxy, with the proviso that at least one substituent $R^4$ is not hydrogen;

$R^a$, $R^b$, $R^c$ independently of one another denote $C_{1-4}$-alkyl, aryl or aryl-$C_{1-3}$-alkyl, while the alkyl may be mono- or polysubstituted by halogen;

L1 and L2 are defined as hereinbefore; and while by the aryl groups mentioned in the definition of the above groups are meant phenyl or naphthyl groups, which may be mono- or polysubstituted with L1;

the protective groups $R^4$ not being hydrogen are cleaved.

2. Process for preparing the compounds of general formula II',

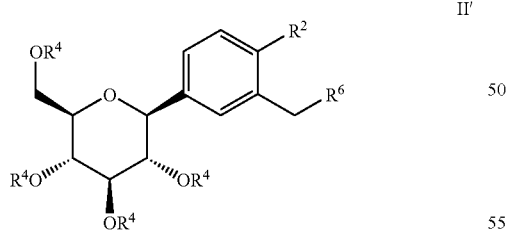

wherein $R^1$ denotes hydrogen, $C_{1-4}$-alkyl, $C_{3-7}$-cycloalkyl, tetrahydrofuranyl, or tetrahydropyranyl, which may be substituted with one to four substituents L2, an aryl-group or a 5- or 6-membered monocyclic heteroaryl-group or a 8-, 9- or 10-membered bicyclic heteroaryl-group wherein said heteroaryl-groups have 1 to 4 heteroatoms independently selected from the group consisting of N, O and S; and wherein said heteroaryl-group may possess 1 or 2 carbonyl groups as part of the mono- or bicyclic aromatic ring-system; and wherein an N-atom of the heteroaryl ring-system may be oxidized to form the corresponding N-oxide; and wherein one or more methine groups in said aryl- and heteroaryl-group may be substituted independently of one another with a substituent L1; and wherein one or more imino-groups in said heteroaryl-group may be substituted independently of one another with a substituent $R^N$; and $R^2$ denotes chlorine or methyl; and $R^4$ independently of one another denote hydrogen, $C_{3-18}$-alkenyl, ($C_{1-18}$-alkyl)-carbonyl, ($C_{1-18}$-alkyl)oxycarbonyl, ($C_{3-18}$-alkenyl)carbonyl, ($C_{3-18}$-alkenyl)oxycarbonyl, di-($C_{1-18}$-alkyl)aminocarbonyl, arylcarbonyl, aryl-($C_{1-3}$-alkyl)-carbonyl, aryl-$C_{1-3}$-alkyl, $C_{1-6}$-alkoxymethyl, aryl-$C_{1-3}$-alkoxy, $C_{1-4}$-alkylthioethyl, arylthioethyl, $C_{1-4}$-alkylsulfonylethyl, arylsulfonylethyl, $R^aR^bR^cSi$, $CR^aR^bOR^c$, wherein two adjacent groups $R^4$ may be linked with each other to form a bridging group $SiR^aR^b$, C=O, $CR^aR^b$ or $CR^aOR^b$—$CR^aOR^b$ and wherein each alkyl group may be substituted with up to three substituents selected from fluorine, chlorine, $C_{1-3}$-alkyl, $R^aR^bR^cSi$, $C_{1-4}$-alkoxy, $R^6$ denotes hydrogen, para-$R^7$-phenyl-, $C_{1-6}$-alkyloxy, aryloxy, —$OR^4$; and $R^7$ denotes —C≡C—$R^1$, Cl, Br, I, —$OSO_2R$, —CHO, —$SiAlk_3$, —O—$C_{1-6}$-alkyl, —$OR^4$, —C≡C—$Si(C_{1-4}$-alkyl)$_3$, —C≡C—Si(aryl)($C_{1-4}$-alkyl)$_2$, —C≡C—Si(biphenyl)($C_{1-4}$-alkyl)$_2$, or —C≡C—C(OH)($C_{1-4}$-alkyl)$_2$; and R denotes $C_{1-4}$-alkyl, $C_{3-4}$-alkenyl, $C_{1-4}$-alkoxy, $CF_3$, aryl or aryl-$C_{1-3}$-alkyl, wherein aryl-groups may be mono- or polysubstituted with L1;

$R^a$, $R^b$, $R^c$ independently of one another denote $C_{1-4}$-alkyl, aryl or aryl-$C_{1-3}$-alkyl, while the alkyl groups may be mono- or polysubstituted by halogen;

$R^N$ independently of one another are selected from among $C_{1-3}$-alkyl; and

L1 independently of one another are selected from among fluorine, chlorine, bromine, $C_{1-3}$-alkyl, $C_{1-4}$-alkoxy and nitro;

L2 independently of one another are selected from among fluorine, chlorine, hydroxy, hydroxyl-$C_{1-4}$-alkyl, $C_{1-4}$-alkoxy, trifluoromethoxy, $C_{1-4}$-alkoxy-$C_{1-4}$-alkyl, cyano, $C_{1-4}$-alkyl, trifluoromethyl, amino, $C_{1-4}$-alkylcarbonylamino, $C_{1-3}$-alkyl-amino and di($C_{1-3}$-alkyl)-amino; and while by the aryl groups mentioned in the definition of the above groups are meant phenyl or naphthyl groups, which may be mono- or polysubstituted with L1;

characterised in that a compound of general formula III'

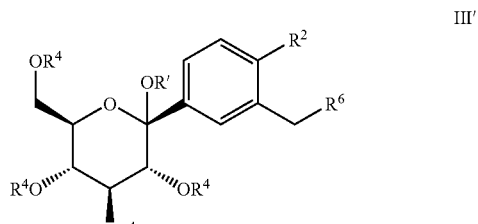

wherein $R^2$, $R^6$ and each $R^4$ are defined as hereinbefore and

R' denotes hydrogen, $C_{1-6}$-alkyl, $(C_{1-4}$-alkyl)carbonyl, $(C_{1-4}$-alkyl)oxycarbonyl, arylcarbonyl, aryl-$(C_{1-3}$-alkyl)-carbonyl; while the term "aryl" is defined as hereinbefore;

is reacted with a reducing agent.

3. Process for preparing the compounds of general formula III',

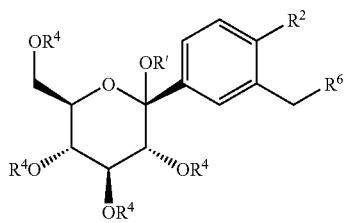

III' wherein $R^2$, R' and each $R^4$ are defined as in claim 2; and $R^6$ denotes hydrogen, para-$R^7$-phenyl-, $C_{1-6}$-alkyloxy, aryloxy, —$OR^4$; and $R^7$ denotes —C≡C—$R^1$, Cl, Br, I, —$OSO_2R$, —CHO, —$SiAlk_3$, —O—$C_{1-6}$-alkyl, —$OR^4$, —C≡C—Si$(C_{1-4}$-alkyl$)_3$, —C≡C—Si(aryl)$(C_{1-4}$-alkyl$)_2$, —C≡C—Si(biphenyl)$(C_{1-4}$-alkyl$)_2$, or —C≡C—C(OH)$(C_{1-4}$-alkyl$)_2$; and R denotes $C_{1-4}$-alkyl, $C_{3-4}$-alkenyl, $C_{1-4}$-alkoxy, $CF_3$, aryl or aryl-$C_{1-3}$-alkyl, wherein aryl-groups may be mono- or polysubstituted with L1;

wherein $R^1$, aryl and L1 are defined as in claim 2;

characterised in that an organometallic compound of the formula VI

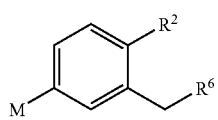

VI wherein $R^2$ and $R^6$ are defined as hereinbefore and M denotes Li or MgHal, wherein Hal denotes Cl, Br or I; and or a derivative thereof obtained by transmetallation;

which compound of the formula VI may be obtained by halogen-metal exchange or by the insertion of a metal in the carbon-halogen bond of a halogen-benzylbenzene compound of general formula V

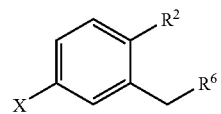

V wherein $R^2$ and $R^6$ are defined as hereinbefore and X denotes Cl, Br or I;

and optionally subsequent transmetallation, is added to a gluconolactone of general formula IV

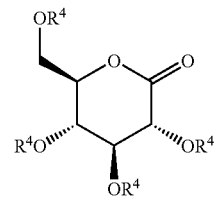

IV wherein $R^4$ is as hereinbefore defined, then the adduct obtained is reacted with water or an alcohol R'—OH, where R' denotes $C_{1-6}$-alkyl, in the presence of an acid and optionally the product obtained in the reaction with water wherein R' denotes H is converted in a subsequent reaction with an acylating agent into the product of formula III' wherein R' denotes $(C_{1-4}$-alkyl)carbonyl, $(C_{1-4}$-alkyl)oxycarbonyl, arylcarbonyl, or aryl-$(C_{1-3}$-alkyl)-carbonyl, wherein the term "aryl" is defined as hereinbefore.

4. Process according to claim 3 characterized in that the compound of formula III' is reacted with a reducing agent to yield a compound of the formula II'

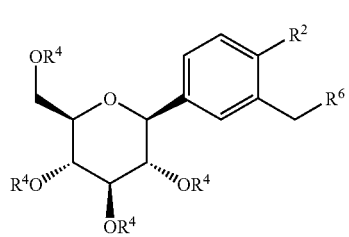

II' wherein $R^2$ is chlorine or methyl $R^4$ independently of one another denote hydrogen, C3-18-alkenyl, (C1 18-alkyl) carbonyl, (C1-18-alkyl)oxycarbonyl, (C3-18-alkenyl)carbonyl, (C3-18-alkenyl)oxycarbonyl, di-(C1-18-alkyl)aminocarbonyl, arylcarbonyl, aryl-(C1-3-alkyl) carbonyl, aryl-C1-3-alkyl, C1 6-alkoxymethyl, aryl-C1-3-alkoxy, C1-4-alkylthioethyl, arylthioethyl, C1-4-alkylsulfonylethyl, arylsulfonylethyl, RaRbRcSi, CRaRbORc, wherein two adjacent groups R4 may be linked with each other to form a bridging group SiRaRb, C=O, CRaRb or CRaORb—CRaORb and wherein each alkyl group may be substituted with up to three substituents selected from fluorine, chlorine, C1 3-alkyl, RaRbRcSi, C1-4-alkoxy, $R^6$ denotes hydrogen, para-R7-phenyl-, C1-6-alkyloxy, aryloxy, —OR4;

$R^7$ denotes —C≡C—$R^1$, Cl, Br, I, —$OSO_2R$, —CHO, —$SiAlk_3$, —O—$C_{1-6}$-alkyl, —$OR^4$, —C≡C—Si$(C_{1-4}$-alkyl$)_3$, —C≡C—Si(aryl)$(C_{1-4}$-alkyl$)_2$, —C≡C—Si(biphenyl)$(C_{1-4}$-alkyl$)_2$, or —C≡C—C(OH)$(C_{1-4}$-alkyl$)_2$.

5. Process for preparing the compounds of general formula X,

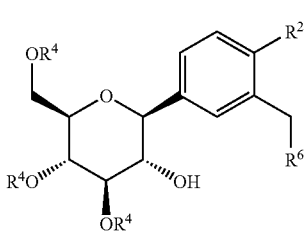

wherein $R^2$ and each $R^4$ are defined as in claim 2; and $R^6$ is defined as in claim 3;
characterised in that a protected D-glucal of the formula VII

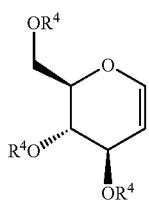

wherein $R^4$ is defined as hereinbefore;
is metallated to yield a metallated D-glucal of the formula VIII

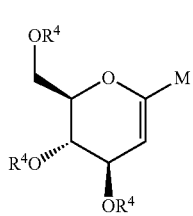

wherein $R^4$ is defined as hereinbefore and M denotes lithium or a magnesium moiety;
which is optionally transmetallated to yield a metallated D-glucal of the formula VIII, wherein M denotes a magnesium, zinc, indium, boron, tin, silicon or chromium moiety; and
the metallated or trans-metallated D-glucal of the formula VIII is reacted with an aglycon of the formula V

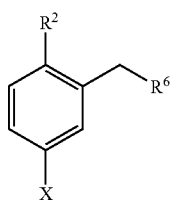

wherein $R^2$ and $R^6$ are defined as hereinbefore and X denotes a replaceable group;
in the presence of a transition metal catalyst to yield a glucal derivative of the formula IX

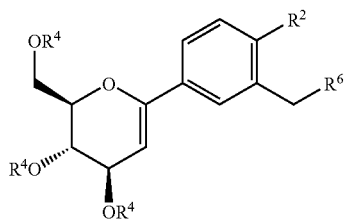

wherein $R^2$, $R^6$ and each $R^4$ are defined as hereinbefore; and
the glucal derivative of the formula IX is converted to the product of the formula X by the addition of water to the double bond of the glucal moiety, in particular by hydroboration of the double bond and subsequent cleavage of the carbon-boron bond or by epoxidation or dihydroxylation of the double bond and subsequent reduction of the resultant anomeric carbon-oxygen bond.

6. Process for preparing the compounds of general formula X

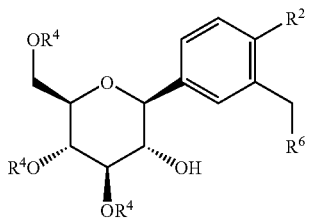

wherein
$R^2$ is chlorine or methyl
$R^4$ independently of one another denote hydrogen, C3-18-alkenyl, (C1 18-alkyl) -carbonyl, (C1-18-alkyl)oxycarbonyl, (C3-18-alkenyl)carbonyl, (C3-18-alkenyl)oxycarbonyl, di-(C1-18-alkyl)aminocarbonyl, arylcarbonyl, aryl-(C1-3-alkyl) carbonyl, aryl-C1-3-alkyl, C1 6-alkoxymethyl, aryl-C1-3-alkoxy, C1-4-alkylthioethyl, arylthioethyl, C1-4-alkylsulfonylethyl, arylsulfonylethyl, RaRbRcSi, CRaRbORc, wherein two adjacent groups R4 may be linked with each other to form a bridging group SiRaRb, C=O, CRaRb or CRaORb—CRaORb and wherein each alkyl group may be substituted with up to three substituents selected from fluorine, chlorine, C1 3-alkyl, RaRbRcSi, C1-4-alkoxy,
$R^6$ denotes hydrogen, para-R7-phenyl-, C1-6-alkyloxy, aryloxy, —OR4;
$R^7$ denotes —C≡C—$R^1$, Cl, Br, I, —OSO$_2$R, —CHO, —SiAlk$_3$, —O—C$_{1-6}$-alkyl, —OR$^4$, —C≡C—Si(C$_{1-4}$-alkyl)$_3$, —C≡C—Si(aryl)(C$_{1-4}$-alkyl)$_2$, —C≡C—Si(biphenyl)(C$_{1-4}$-alkyl)$_2$, or —C≡C—C(OH)(C$_{1-4}$-alkyl)$_2$; and characterised in that a protected D-glucal of the formula VII

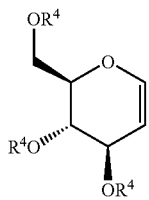

wherein $R^4$ is defined as hereinbefore;
is epoxidated to yield the corresponding glucaloxide of the formula XI

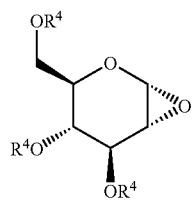

wherein $R^4$ is defined as hereinbefore; and
the glucaloxide of the formula XI is reacted with an aglycon of the formula VI

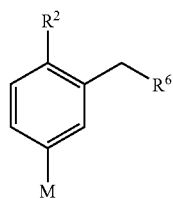

wherein $R^2$ and $R^6$ is defined as hereinbefore and M denotes a lithium, magnesium, zinc, indium, aluminum or boron moiety;
to yield the product of the formula X.

7. Process for preparing the compounds of general formula II',

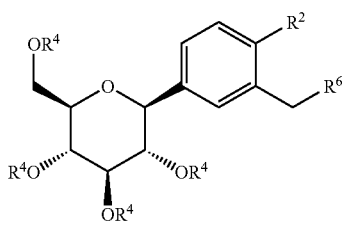

wherein
$R^2$
R2 is chlorine or methyl
R4 independently of one another denote hydrogen, C3-18-alkenyl, (C1 18-alkyl) carbonyl, (C1-18-alkyl)oxycarbonyl, (C3-18-alkenyl)carbonyl, (C3-18-alkenyl)oxycarbonyl, di-(C1-18-alkyl)aminocarbonyl, arylcarbonyl, aryl-(C1-3-alkyl)-carbonyl, aryl-C1-3-alkyl, C1 6-alkoxymethyl, aryl-C1-3-alkoxy, C1-4-alkylthioethyl, arylthioethyl, C1-4-alkylsulfonylethyl, arylsulfonylethyl, RaRbRcSi, CRaRbORc, wherein two adjacent groups R4 may be linked with each other to form a bridging group SiRaRb, C=O, CRaRb or CraORb—CRaORb and wherein each alkyl group may be substituted with up to three substituents selected from fluorine, chlorine, C1 3-alkyl, RaRbRcSi, C1-4-alkoxy, $R^6$ denotes hydrogen, para-$R^7$-phenyl-, C1-6-alkyloxy, aryloxy, —OR4;

$R^7$ denotes —C≡C—$R^1$, Cl, Br, I, —OSO$_2$R, —CHO, —SiAlk$_3$, —O—C$_{1-6}$-alkyl, —OR$^4$, —C≡C—Si(C$_{1-4}$-alkyl)$_3$, —C≡C—Si(aryl)(C$_{1-4}$-alkyl)$_2$, —C≡C—Si(biphenyl)(C$_{1-4}$-alkyl)$_2$, or —C≡C—C(OH)(C$_{1-4}$-alkyl)$_2$;

characterised in that a glucose derivative of the formula XII

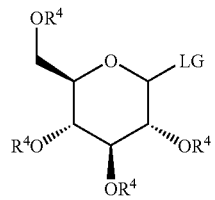

wherein $R^4$ is defined as hereinbefore and LG denotes F, Cl, Br, C$_{1-3}$-alkylcarbonyloxy, C$_{1-3}$-alkyloxycarbonyloxy, C$_{1-3}$-alkyloxy or trichloroacetimidate;
is reacted with a metallated aglycon of the formula VI

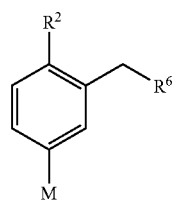

wherein $R^2$ is defined as hereinbefore; and $R^6$ is defined as in claim 3; and M denotes a lithium, magnesium, zinc, indium or boron moiety;
to yield the product of the formula II'.

8. Process according to claim 5 characterized in that in the product of the formula X the hydroxyl group in 2-position of the pyranosyl-ring is protected by a group $R^4$ not being hydrogen to yield a compound of the formula II'

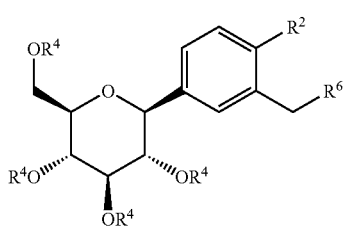

wherein $R^2$, $R^6$ and each $R^4$ are defined as hereinbefore.

9. Process according to claim 3 wherein the group $R^6$ denotes a group of the subformula

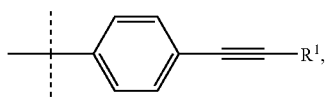

wherein $R^1$ is hydrogen or
C1-4-alkyl, C3-7-cycloalkyl, tetrahydrofuranyl, or tetrahydropyranyl, which may be substituted with one to four substituents L2, or
an aryl-group or a 5- or 6-membered monocyclic heteroaryl-group or a 8-, 9- or 10-membered bicyclic heteroaryl-group wherein said heteroaryl-groups have 1 to 4 heteroatoms independently selected from the group consisting of N, O and S; and wherein said heteroaryl-group may possess 1 or 2 carbonyl groups as part of the mono- or bicyclic aromatic ring-system; and
wherein an N-atom of the heteroaryl ring-system may be oxidized to form the corresponding N-oxide; and
wherein one or more methine groups in said aryl- and heteroaryl-group may be substituted independently of one another with a substituent L1; and
wherein one or more imino-groups in said heteroaryl-group may be substituted independently of one another with a substituent RN.

10. Process for preparing compounds of the formula XXVI'

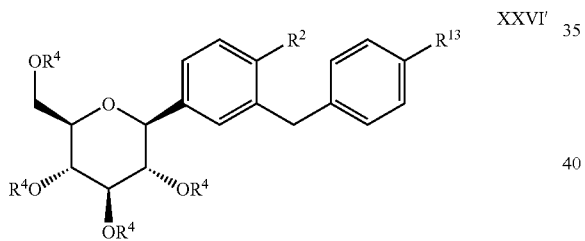

wherein
$R^2$ denotes chlorine or methyl; and
$R^4$ independently of one another denote hydrogen, $C_{3-18}$-alkenyl, $(C_{1-18}$-alkyl)-carbonyl, $(C_{1-18}$-alkyl)oxycarbonyl, $(C_{3-18}$-alkenyl)carbonyl, $(C_{3-18}$-alkenyl)oxycarbonyl, di-$(C_{1-18}$-alkyl)aminocarbonyl, arylcarbonyl, aryl-$(C_{1-3}$-alkyl)-carbonyl, aryl-$C_{1-3}$-alkyl, $C_{1-6}$-alkoxymethyl, aryl-$C_{1-3}$-alkoxy, $C_{1-4}$-alkylthioethyl, arylthioethyl, $C_{1-4}$-alkylsulfonylethyl, arylsulfonylethyl, $R^aR^bR^cSi$, $CR^aR^bOR^c$, wherein two adjacent groups $R^4$ may be linked with each other to form a bridging group $SiR^aR^b$, C=O, $CR^aR^b$ or $CR^aOR^b$—$CR^aOR^b$ and wherein each alkyl group may be substituted with up to three substituents selected from fluorine, chlorine, $C_{1-3}$-alkyl, $R^aR^bR^cSi$, $C_{1-4}$-alkoxy,
$R^{13}$ denotes —CHO, —C≡C—$R^1$, OH, $C_{1-6}$-alkyloxy, —Si$(C_{1-6}$-alkyl$)_3$, —C≡C—Si$(C_{1-4}$-alkyl$)_3$, —C≡C—Si(aryl)$(C_{1-4}$-alkyl$)_2$, —C≡C—Si(biphenyl)$(C_{1-4}$-alkyl$)_2$, —C≡C—C(OH)$(C_{1-4}$-alkyl$)_2$, iodine, bromine, chlorine, or $C_{1-6}$-alkylsulfonyloxy; wherein $R^1$ is defined as in claim 1;
characterized in that in a compound of the formula X

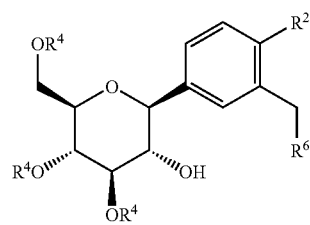

wherein $R^2$ and each $R^4$ are defined hereinbefore; and $R^6$ denotes hydrogen, OH, $C_{1-6}$-alkyloxy or aryloxy
or in a compound of the formula II'

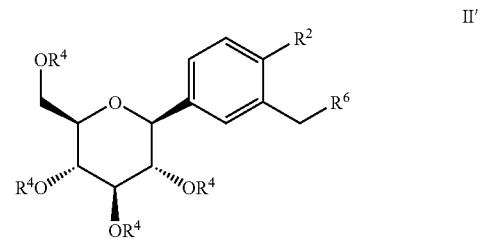

wherein $R^2$, $R^6$ and each $R^4$ are defined as hereinbefore; the group $R^6$ is transformed into a group $Z^4$ to yield a compound of the formula XXXIX

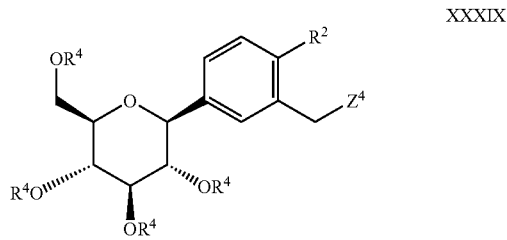

wherein $R^2$ and each $R^4$ are defined as hereinbefore; and $Z^4$ denotes chlorine, bromine, iodine, $C_{1-6}$-alkyloxy, aryloxy, $C_{1-6}$-alkylcarbonyl-oxy, $C_{1-6}$-alkyloxycarbonyloxy, $C_{1-6}$-alkylsulfonyloxy, —OPO(O—$C_{1-6}$-alkyl$)_2$, or aryloxy;
and the compound of the formula XXXIX is reacted with a metalated benzene of the formula XXIII

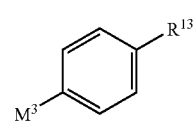

wherein $R^{13}$ is defined as hereinbefore; and
$M^3$ denotes a lithium-, boron-, magnesium-, silicon-, tin-, cerium-, indium-, zinc-, or chromium-moiety; to yield a compound of the formula XXVI'.

11. Process according to claim 10 characterized in that in the compound of the formula XXVI' wherein the group $R^{13}$ which does not denote —C≡C—$R^1$ is transformed into a group —C≡C—R$^1$, wherein R$^1$ is hydrogen, or C1-4-alkyl, C3-7-cycloalkyl, tetrahydrofuranyl, or tetrahydropyranyl, which may be substituted with one to four substituents L2, or an aryl-group or a 5- or 6-membered monocyclic heteroaryl-group or a 8-, 9- or 10-membered bicyclic heteroaryl-group wherein said heteroaryl-groups have 1 to 4 heteroatoms independently selected from the group consisting of N, O and S; and wherein said heteroaryl-group may possess 1 or 2 carbonyl groups as part of the mono- or bicyclic aromatic ring-system; and wherein an N-atom of the heteroaryl ring-system may be oxidized to form the corresponding N-oxide; and wherein one or more methine groups in said aryl- and heteroaryl-group may be substituted independently of one another with a substituent L1; and wherein one or more imino-groups in said heteroaryl-group may be substituted independently of one another with a substituent RN.

12. Process according to claim 10 characterized in that the group R$^{13}$ denotes —C≡C—R$^1$.

13. Process according to claim 10 wherein product of the formula XXVI' protective groups R$^4$ not being hydrogen are cleaved.

14. Process according to claim 1 characterized in that one or more of the groups R$^4$ independently of each other denote hydrogen, (C$_{1-6}$-alkyl)carbonyl, (C$_{1-6}$-alkyl)oxycarbonyl, (C$_{3-6}$-alkenyl)oxycarbonyl, arylcarbonyl, aryl-methyl, C$_{1-6}$-alkoxymethyl, R$^a$R$^b$R$^c$Si, CR$^a$R$^b$OR$^c$, wherein two adjacent groups R$^4$ may be linked with each other to form a bridging group SiR$^a$R$^b$, C=O, CR$^a$R$^b$ or CR$^a$OR$^b$—CR$^a$OR$^b$ and wherein each alkyl group may be substituted with up to three substituents selected from fluorine, chlorine, C$_{1-3}$-alkyl, R$^a$R$^b$R$^c$Si and C$_{1-4}$-alkoxy; wherein R$^a$, R$^b$, R$^c$ and aryl are defined as in claim 1.

15. Process according to claim 1 characterized in that the group R$^1$ denotes hydrogen or C$_{1-4}$-alkyl, cyclopropyl, cyclobutyl, cyclopentyl, cyclohexyl, tetrahydrofuranyl or tetrahydropyranyl, which may be substituted with one or two substituents L2.

16. Compound of general formula IX

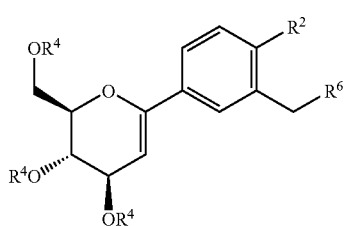

IX wherein:
R$^2$ denotes chlorine or methyl;
R$^4$ independently of one another denote hydrogen, C3-18-alkenyl, (C1-18-alkyl)-carbonyl, (C1-18-alkyl)oxycarbonyl, (C3-18-alkenyl)carbonyl, (C3-18-alkenyl)oxycarbonyl, di-(C1-18-alkyl)aminocarbonyl, arylcarbonyl, aryl-(C1-3-alkyl)-carbonyl, aryl-C1-3-alkyl, C1-6-alkoxymethyl, aryl-C1-3-alkoxy, C1-4-alkylthioethyl, arylthioethyl, C1-4-alkylsulfonylethyl, arylsulfonylethyl, RaRbRcSi, CRaRbORc, wherein two adjacent R$^4$ groups may be linked with each other to form a bridging group SiRaRb, C=O, CRaRb or CRaORb—CRaORb and wherein each alkyl group may be substituted with up to three substituents selected from fluorine, chlorine, C1-3-alkyl, RaRbRcSi, and C1-4-alkoxy;

R$^6$ denotes hydrogen, para-R$^7$-phenyl-, C1-6-alkyloxy, aryloxy, or OR$^4$;

R$^7$ denotes —C≡C—R$^1$, Cl, Br, I, —OSO$_2$R, —CHO, —SiAlk$_3$, —O—C$_{1-6}$-alkyl, —OR$^4$, —C≡C—Si(C$_{1-4}$-alkyl)$_3$, —C≡C—Si(aryl)(C$_{1-4}$-alkyl)$_2$, —C≡C—Si(biphenyl)(C$_{1-4}$-alky)$_2$, or —C≡C—C(OH)(C$_{1-4}$-alkyl)$_2$;

R$^1$ denotes hydrogen, C$_{1-4}$-alkyl, C$_{3-7}$-cycloalkyl, tetrahydrofuranyl, or tetrahydropyranyl, which may be substituted with one to four substituents L2, an aryl-group or a 5- or 6-membered monocyclic heteroaryl-group or a 8-, 9- or 10-membered bicyclic heteroaryl-group wherein said heteroaryl-groups have 1 to 4 heteroatoms independently selected from the group consisting of N, O and S;

and wherein said heteroaryl-group may possess 1 or 2 carbonyl groups as part of the mono- or bicyclic aromatic ring-system; and, wherein an N-atom of the heteroaryl ring-system may be oxidized to form the corresponding N-oxide; and, wherein one or more methine groups in said aryl- and heteroaryl-group may be substituted independently of one another with a substituent L1; and, wherein one or more imino-groups in said heteroaryl-group may be substituted independently of one another with a substituent R$^N$; and, R$^N$ independently of one another are selected from among C$_{1-3}$ alkyl; and, R denotes C$_{1-4}$-alkyl, C$_{3-4}$-alkenyl, C$_{1-4}$-alkoxy, CF$_3$, aryl or aryl-C$_{1-3}$-alkyl, wherein aryl-groups may be mono- or polysubstituted with L1;

L1 independently of one another are selected from among fluorine, chlorine, bromine, C$_{1-3}$-alkyl, C$_{1-4}$-alkoxy, and nitro;

L2 independently of one another are selected from among fluorine, chlorine, hydroxy, hydroxyl-C$_{1-4}$-alkyl, C$_{1-4}$-alkoxy, trifluoromethoxy, C$_{1-4}$-alkoxy-C$_{1-4}$-alkyl, cyano, C$_{1-4}$-alkyl, trifluoromethyl, amino, C$_{1-4}$-alkyl-carbonylamino, C$_{1-3}$-alkyl-amino and di(C$_{1-3}$-alkyl)-amino;

while the aryl groups mentioned in the definition of the above groups are meant phenyl or naphthyl groups, which may be mono- or polysubstituted with L1; and, Ra, Rb, and Rc independently of one another denote C1-4-alkyl, aryl, or aryl-C1-3-alkyl, while alkyl may be mono- or polysubstituted by halogen.

* * * * *